US009757107B2

(12) United States Patent
McNamara et al.

(10) Patent No.: US 9,757,107 B2
(45) Date of Patent: Sep. 12, 2017

(54) METHODS AND DEVICES FOR INTRA-ATRIAL SHUNTS HAVING ADJUSTABLE SIZES

(71) Applicant: CORVIA MEDICAL, INC., Tewksbury, MA (US)

(72) Inventors: Edward I. McNamara, Chelmsford, MA (US); Michael W. Sutherland, Pelham, NH (US); Matthew J. Finch, Medford, MA (US); Stephen J. Forcucci, Winchester, MA (US); John Mitzel, Chester, NH (US); David S. Celermajer, Vaucluse (AU); Hiroatsu Sugimoto, Cambridge, MA (US)

(73) Assignee: Corvia Medical, Inc., Tewksbury, MA (US)

( * ) Notice: Subject to any disclaimer, the term of this patent is extended or adjusted under 35 U.S.C. 154(b) by 0 days.

(21) Appl. No.: 14/612,022

(22) Filed: Feb. 2, 2015

(65) Prior Publication Data

US 2015/0148731 A1    May 28, 2015

Related U.S. Application Data

(63) Continuation-in-part of application No. 13/726,472, filed on Dec. 24, 2012, now Pat. No. 9,642,993, and
(Continued)

(51) Int. Cl.
*A61B 17/00* (2006.01)
*A61F 2/91* (2013.01)
(Continued)

(52) U.S. Cl.
CPC ...... *A61B 17/0057* (2013.01); *A61B 2017/00247* (2013.01); *A61B 2017/00575* (2013.01);
(Continued)

(58) Field of Classification Search
CPC ...... A61B 17/0057; A61B 2017/00247; A61B 2017/00575; A61B 2017/00584;
(Continued)

(56) References Cited

U.S. PATENT DOCUMENTS 3,874,388 A    4/1975 King et al.
4,018,228 A    4/1977 Goosen
(Continued)

FOREIGN PATENT DOCUMENTS

CN    1218379 A    6/1999
CN    1556719 A    12/2004
(Continued)

OTHER PUBLICATIONS

Forcucci et al.; U.S. Appl. No. 14/807,544 entitled "Devices and methods for treating heart failure," filed Jul. 23, 2015.
(Continued)

*Primary Examiner* — Tatyana Zalukaeva
*Assistant Examiner* — Benjamin Klein
(74) *Attorney, Agent, or Firm* — Shay Glenn LLP

(57) ABSTRACT

Devices and methods for treating heart disease by normalizing elevated blood pressure in the left and right atria of a heart of a mammal are disclosed. Devices may include an adjustable hydraulic diameter shunt portion which can be manually adjusted in vivo. Methods are provided for adjusting the flow rate of the devices in vivo.

7 Claims, 47 Drawing Sheets

Related U.S. Application Data a continuation-in-part of application No. 12/848,084, filed on Jul. 30, 2010, and a continuation of application No. 12/719,843, filed on Mar. 8, 2010, now Pat. No. 8,157,860.

(60) Provisional application No. 61/579,426, filed on Dec. 22, 2011, provisional application No. 61/659,520, filed on Jun. 14, 2012, provisional application No. 61/240,085, filed on Sep. 4, 2009.

(51) Int. Cl.
  *A61F 2/915* (2013.01)
  *A61F 2/07* (2013.01)

(52) U.S. Cl.
  CPC .............. *A61B 2017/00584* (2013.01); *A61B 2017/00592* (2013.01); *A61B 2017/00606* (2013.01); *A61B 2017/00623* (2013.01); *A61F 2/91* (2013.01); *A61F 2/915* (2013.01); *A61F 2002/075* (2013.01)

(58) Field of Classification Search
  CPC . A61B 2017/00592; A61B 2017/00623; A61F 2/91; A61F 2/915; A61F 2002/075
  See application file for complete search history.

(56) References Cited

U.S. PATENT DOCUMENTS

| | | |
|---|---|---|
| 4,373,216 A | 2/1983 | Klawitter |
| 4,491,986 A | 1/1985 | Gabbay |
| 4,705,507 A | 11/1987 | Boyles |
| 5,100,423 A | 3/1992 | Fearnot |
| 5,108,420 A | 4/1992 | Marks |
| 5,171,233 A | 12/1992 | Amplatz et al. |
| 5,284,488 A | 2/1994 | Sideris |
| 5,332,402 A | 7/1994 | Teitelbaum |
| 5,334,217 A | 8/1994 | Das |
| 5,413,599 A | 5/1995 | Imachi et al. |
| 5,429,144 A | 7/1995 | Wilk |
| 5,433,727 A | 7/1995 | Sideris |
| 5,464,449 A | 11/1995 | Ryan et al. |
| 5,478,353 A | 12/1995 | Yoon |
| 5,556,386 A | 9/1996 | Todd |
| 5,556,408 A | 9/1996 | Farhat |
| 5,693,090 A | 12/1997 | Unsworth et al. |
| 5,702,412 A | 12/1997 | Popov et al. |
| 5,725,552 A | 3/1998 | Kotula et al. |
| 5,824,071 A | 10/1998 | Nelson et al. |
| 5,846,261 A | 12/1998 | Kotula et al. |
| 5,876,436 A | 3/1999 | Vanney et al. |
| 5,893,369 A | 4/1999 | Lemole |
| 5,944,738 A | 8/1999 | Amplatz et al. |
| 5,964,754 A | 10/1999 | Osypka |
| 6,050,936 A | 4/2000 | Schweich et al. |
| 6,059,827 A | 5/2000 | Fenton |
| 6,068,635 A | 5/2000 | Gianotti |
| 6,120,534 A | 9/2000 | Ruiz |
| 6,123,682 A | 9/2000 | Knudson et al. |
| 6,123,715 A | 9/2000 | Amplatz |
| 6,152,937 A | 11/2000 | Peterson et al. |
| 6,156,055 A | 12/2000 | Ravenscroft |
| 6,168,622 B1 | 1/2001 | Mazzocchi |
| 6,190,353 B1 | 2/2001 | Makower et al. |
| 6,193,734 B1 | 2/2001 | Bolduc et al. |
| 6,210,338 B1 | 4/2001 | Afremov et al. |
| 6,241,678 B1 | 6/2001 | Afremov et al. |
| 6,258,119 B1 | 7/2001 | Hussein et al. |
| 6,286,512 B1 | 9/2001 | Loeb et al. |
| 6,334,864 B1 | 1/2002 | Amplatz et al. |
| 6,350,277 B1 | 2/2002 | Kocur |
| 6,355,052 B1 | 3/2002 | Neuss et al. |
| 6,355,056 B1 | 3/2002 | Pinheiro |
| 6,357,735 B2 | 3/2002 | Haverinen |
| 6,383,195 B1 | 5/2002 | Richard |
| 6,395,017 B1 | 5/2002 | Dwyer et al. |
| 6,402,777 B1 | 6/2002 | Globerman et al. |
| 6,409,716 B1 | 6/2002 | Sahatjian et al. |
| 6,440,152 B1 | 8/2002 | Gainor et al. |
| 6,454,795 B1 | 9/2002 | Chuter |
| 6,458,153 B1 | 10/2002 | Bailey et al. |
| 6,468,301 B1 | 10/2002 | Amplatz et al. |
| 6,468,303 B1 | 10/2002 | Amplatz et al. |
| 6,527,746 B1 | 3/2003 | Oslund et al. |
| 6,572,652 B2 | 6/2003 | Shaknovich |
| 6,579,311 B1 | 6/2003 | Makower |
| 6,599,308 B2 | 7/2003 | Amplatz |
| 6,626,936 B2 | 9/2003 | Stinson |
| 6,638,257 B2 | 10/2003 | Amplatz |
| 6,645,143 B2 | 11/2003 | Vantassel et al. |
| 6,666,885 B2 | 12/2003 | Moe |
| 6,712,836 B1 | 3/2004 | Berg et al. |
| 6,719,768 B1 | 4/2004 | Cole et al. |
| 6,837,901 B2 | 1/2005 | Rabkin et al. |
| 6,866,679 B2 | 3/2005 | Kusleika |
| 6,911,037 B2 | 6/2005 | Gainor et al. |
| 6,913,614 B2 | 7/2005 | Marino et al. |
| 6,932,837 B2 | 8/2005 | Amplatz et al. |
| 6,936,058 B2 | 8/2005 | Forde et al. |
| 6,979,343 B2 | 12/2005 | Russo et al. |
| 7,033,372 B1 | 4/2006 | Cahalan |
| 7,037,329 B2 | 5/2006 | Martin |
| 7,044,134 B2 | 5/2006 | Khairkhahan et al. |
| 7,097,653 B2 | 8/2006 | Freudenthal et al. |
| 7,105,024 B2 | 9/2006 | Richelsoph |
| 7,226,466 B2 | 6/2007 | Opolski |
| 7,317,951 B2 | 1/2008 | Schneider et al. |
| 7,338,514 B2 | 3/2008 | Wahr et al. |
| 7,350,995 B1 | 4/2008 | Rhodes |
| 7,419,498 B2 | 9/2008 | Opolski et al. |
| 7,445,630 B2 | 11/2008 | Lashinski et al. |
| 7,473,266 B2 | 1/2009 | Glaser |
| 7,485,141 B2 | 2/2009 | Majercak et al. |
| 7,530,995 B2 | 5/2009 | Quijano et al. |
| 7,611,534 B2 | 11/2009 | Kapadia et al. |
| 7,625,392 B2 | 12/2009 | Coleman et al. |
| 7,658,747 B2 | 2/2010 | Forde et al. |
| 7,678,123 B2 | 3/2010 | Chanduszko |
| 7,691,144 B2 | 4/2010 | Chang et al. |
| 7,699,297 B2 | 4/2010 | Cicenas et al. |
| 7,704,268 B2 | 4/2010 | Chanduszko |
| 7,722,629 B2 | 5/2010 | Chambers |
| 7,842,026 B2 | 11/2010 | Cahill et al. |
| 7,871,419 B2 | 1/2011 | Devellian et al. |
| 7,905,901 B2 | 3/2011 | Corcoran et al. |
| 7,967,769 B2 | 6/2011 | Faul et al. |
| 7,976,564 B2 | 7/2011 | Blaeser et al. |
| 8,010,186 B1 | 8/2011 | Ryu |
| 8,021,359 B2 | 9/2011 | Auth et al. |
| 8,034,061 B2 | 10/2011 | Amplatz et al. |
| 8,043,360 B2 | 10/2011 | McNamara et al. |
| 8,048,147 B2 | 11/2011 | Adams |
| 8,052,750 B2 | 11/2011 | Tuval et al. |
| 8,157,860 B2 | 4/2012 | McNamara et al. |
| 8,163,004 B2 | 4/2012 | Amplatz et al. |
| 8,172,896 B2 | 5/2012 | McNamara et al. |
| 8,252,042 B2 | 8/2012 | McNamara et al. |
| 8,303,623 B2 | 11/2012 | Melzer et al. |
| 8,313,505 B2 | 11/2012 | Amplatz et al. |
| 8,361,138 B2 | 1/2013 | Adams |
| 8,366,088 B2 | 2/2013 | Allen et al. |
| 8,398,670 B2 | 3/2013 | Amplatz et al. |
| 8,460,372 B2 | 6/2013 | McNamara et al. |
| 8,696,611 B2 | 4/2014 | Nitzan et al. |
| 8,740,962 B2 | 6/2014 | Finch et al. |
| 8,745,845 B2 | 6/2014 | Finch et al. |
| 8,747,453 B2 | 6/2014 | Amplatz et al. |
| 8,752,258 B2 | 6/2014 | Finch et al. |
| 8,777,974 B2 | 7/2014 | Amplatz et al. |
| 8,778,008 B2 | 7/2014 | Amplatz et al. |
| 8,864,822 B2 | 10/2014 | Spence et al. |
| 8,882,697 B2 | 11/2014 | Celermajer et al. |
| 8,951,223 B2 | 2/2015 | McNamara et al. |

(56) References Cited

U.S. PATENT DOCUMENTS

| | | |
|---|---|---|
| 8,979,923 B2 | 3/2015 | Spence et al. |
| 9,005,155 B2 | 4/2015 | Sugimoto |
| 2001/0027287 A1 | 10/2001 | Shmulewitz et al. |
| 2001/0029368 A1 | 10/2001 | Berube |
| 2001/0053932 A1 | 12/2001 | Phelps et al. |
| 2002/0077698 A1 | 6/2002 | Peredo |
| 2002/0082525 A1 | 6/2002 | Oslund et al. |
| 2002/0082613 A1 | 6/2002 | Hathaway et al. |
| 2002/0095172 A1 | 7/2002 | Mazzocchi et al. |
| 2002/0120277 A1 | 8/2002 | Hauschild et al. |
| 2002/0143289 A1 | 10/2002 | Ellis et al. |
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1 | 11/2002 | Keren et al. |
| 2002/0177894 A1 | 11/2002 | Acosta et al. |
| 2002/0183826 A1 | 12/2002 | Dorn et al. |
| 2003/0093072 A1 | 5/2003 | Friedman |
| 2003/0125798 A1 | 7/2003 | Martin |
| 2004/0044351 A1 | 3/2004 | Searle |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0102797 A1 | 5/2004 | Golden et al. |
| 2004/0111095 A1 | 6/2004 | Gordon et al. |
| 2004/0133236 A1 | 7/2004 | Chanduszko |
| 2004/0143261 A1 | 7/2004 | Hartley et al. |
| 2004/0143262 A1 | 7/2004 | Visram et al. |
| 2004/0143292 A1 | 7/2004 | Marino et al. |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | McCarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |
| 2005/0015953 A1 | 1/2005 | Keidar |
| 2005/0049692 A1 | 3/2005 | Numamoto et al. |
| 2005/0049697 A1 | 3/2005 | Sievers |
| 2005/0065507 A1 | 3/2005 | Hartley et al. |
| 2005/0065548 A1 | 3/2005 | Marino et al. |
| 2005/0070934 A1 | 3/2005 | Tanaka et al. |
| 2005/0075655 A1 | 4/2005 | Bumbalough et al. |
| 2005/0080400 A1 | 4/2005 | Corcoran et al. |
| 2005/0080430 A1 | 4/2005 | Wright et al. |
| 2005/0096735 A1 | 5/2005 | Hojeibane et al. |
| 2005/0113868 A1 | 5/2005 | Devellian et al. |
| 2005/0131503 A1 | 6/2005 | Solem |
| 2005/0137609 A1 | 6/2005 | Guiraudon |
| 2005/0137686 A1 | 6/2005 | Salahieh et al. |
| 2005/0148925 A1 | 7/2005 | Rottenberg et al. |
| 2005/0159738 A1 | 7/2005 | Visram et al. |
| 2005/0165344 A1 | 7/2005 | Dobak |
| 2005/0187616 A1 | 8/2005 | Realyvasquez |
| 2005/0240205 A1 | 10/2005 | Berg et al. |
| 2005/0251063 A1 | 11/2005 | Basude |
| 2005/0251187 A1 | 11/2005 | Beane et al. |
| 2005/0267524 A1 | 12/2005 | Chanduszko |
| 2005/0273075 A1 | 12/2005 | Krulevitch et al. |
| 2005/0273124 A1 | 12/2005 | Chanduszko |
| 2005/0288722 A1 | 12/2005 | Eigler et al. |
| 2006/0004323 A1 | 1/2006 | Chang et al. |
| 2006/0009800 A1 | 1/2006 | Christianson et al. |
| 2006/0009832 A1 | 1/2006 | Fisher |
| 2006/0041183 A1 | 2/2006 | Massen et al. |
| 2006/0085060 A1 | 4/2006 | Campbell |
| 2006/0095066 A1 | 5/2006 | Chang et al. |
| 2006/0122646 A1 | 6/2006 | Corcoran et al. |
| 2006/0122647 A1 | 6/2006 | Callaghan et al. |
| 2006/0135990 A1 | 6/2006 | Johnson |
| 2006/0136043 A1 | 6/2006 | Cully et al. |
| 2006/0155305 A1 | 7/2006 | Freudenthal et al. |
| 2006/0184088 A1 | 8/2006 | Van Bibber et al. |
| 2006/0210605 A1 | 9/2006 | Chang et al. |
| 2006/0241745 A1 | 10/2006 | Solem |
| 2006/0247680 A1 | 11/2006 | Amplatz et al. |
| 2006/0253184 A1 | 11/2006 | Amplatz |
| 2006/0259121 A1 | 11/2006 | Osypka |
| 2006/0276882 A1 | 12/2006 | Case et al. |
| 2007/0005127 A1 | 1/2007 | Boekstegers et al. |
| 2007/0021739 A1 | 1/2007 | Weber |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0129755 A1 | 6/2007 | Abbott et al. |
| 2007/0168018 A1 | 7/2007 | Amplatz et al. |
| 2007/0185513 A1 | 8/2007 | Woolfson et al. |
| 2007/0197952 A1 | 8/2007 | Stiger |
| 2007/0198060 A1 | 8/2007 | Devellian et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039881 A1 | 2/2008 | Greenberg |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0109069 A1 | 5/2008 | Coleman et al. |
| 2008/0119891 A1 | 5/2008 | Miles et al. |
| 2008/0125861 A1 | 5/2008 | Webler et al. |
| 2008/0154250 A1 | 6/2008 | Makower et al. |
| 2008/0154302 A1 | 6/2008 | Opolski et al. |
| 2008/0154351 A1 | 6/2008 | Leewood et al. |
| 2008/0154355 A1 | 6/2008 | Benichou et al. |
| 2008/0161901 A1 | 7/2008 | Heuser et al. |
| 2008/0172123 A1 | 7/2008 | Yadin |
| 2008/0177381 A1 | 7/2008 | Navia et al. |
| 2008/0183279 A1 | 7/2008 | Bailey et al. |
| 2008/0188888 A1 | 8/2008 | Adams et al. |
| 2008/0215008 A1 | 9/2008 | Nance et al. |
| 2008/0221582 A1 | 9/2008 | Gia et al. |
| 2008/0228264 A1 | 9/2008 | Li et al. |
| 2008/0249397 A1 | 10/2008 | Kapadia |
| 2008/0249612 A1 | 10/2008 | Osborne et al. |
| 2008/0262592 A1 | 10/2008 | Jordan et al. |
| 2008/0269662 A1 | 10/2008 | Vassiliades et al. |
| 2008/0312679 A1 | 12/2008 | Hardert et al. |
| 2009/0018570 A1 | 1/2009 | Righini et al. |
| 2009/0030495 A1 | 1/2009 | Koch |
| 2009/0054805 A1 | 2/2009 | Boyle |
| 2009/0054984 A1 | 2/2009 | Shortkroff et al. |
| 2009/0062841 A1 | 3/2009 | Amplatz et al. |
| 2009/0076541 A1 | 3/2009 | Chin et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal |
| 2009/0112251 A1 | 4/2009 | Qian et al. |
| 2009/0171386 A1 | 7/2009 | Amplatz et al. |
| 2009/0177269 A1 | 7/2009 | Kalmann et al. |
| 2009/0187214 A1 | 7/2009 | Amplatz et al. |
| 2009/0209855 A1 | 8/2009 | Drilling et al. |
| 2009/0209999 A1 | 8/2009 | Afremov |
| 2009/0234443 A1 | 9/2009 | Ottma et al. |
| 2009/0264991 A1 | 10/2009 | Paul et al. |
| 2009/0270840 A1 | 10/2009 | Miles et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030259 A1 | 2/2010 | Pavcnik et al. |
| 2010/0030321 A1 | 2/2010 | Mach |

(56) References Cited

U.S. PATENT DOCUMENTS

| | | |
|---|---|---|
| 2010/0049307 A1 | 2/2010 | Ren |
| 2010/0051886 A1 | 3/2010 | Cooke et al. |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0114140 A1 | 5/2010 | Chanduszko |
| 2010/0121370 A1 | 5/2010 | Kariniemi |
| 2010/0131053 A1 | 5/2010 | Agnew |
| 2010/0211046 A1 | 8/2010 | Adams et al. |
| 2010/0249490 A1 | 9/2010 | Farnan |
| 2010/0249491 A1 | 9/2010 | Farnan et al. |
| 2010/0256753 A1* | 10/2010 | McNamara ........ A61B 17/0057 623/2.17 |
| 2010/0268316 A1 | 10/2010 | Brenneman et al. |
| 2010/0274351 A1 | 10/2010 | Rolando et al. |
| 2010/0298755 A1 | 11/2010 | McNamara et al. |
| 2010/0305685 A1 | 12/2010 | Millwee et al. |
| 2010/0324588 A1 | 12/2010 | Miles et al. |
| 2011/0004296 A1 | 1/2011 | Lutter et al. |
| 2011/0022079 A1 | 1/2011 | Miles et al. |
| 2011/0071623 A1 | 3/2011 | Finch et al. |
| 2011/0071624 A1 | 3/2011 | Finch et al. |
| 2011/0087261 A1 | 4/2011 | Wittkampf et al. |
| 2011/0093062 A1 | 4/2011 | Cartledge et al. |
| 2011/0106149 A1 | 5/2011 | Ryan et al. |
| 2011/0130784 A1 | 6/2011 | Kusleika |
| 2011/0184439 A1 | 7/2011 | Anderson et al. |
| 2011/0190874 A1 | 8/2011 | Celermajer et al. |
| 2011/0213364 A1 | 9/2011 | Davis et al. |
| 2011/0218479 A1 | 9/2011 | Rottenberg et al. |
| 2011/0257723 A1 | 10/2011 | McNamara |
| 2011/0270239 A1 | 11/2011 | Werneth |
| 2011/0295183 A1 | 12/2011 | Finch et al. |
| 2011/0319806 A1 | 12/2011 | Wardle |
| 2011/0319989 A1 | 12/2011 | Lane et al. |
| 2012/0022427 A1 | 1/2012 | Kapadia |
| 2012/0130301 A1 | 5/2012 | McNamara et al. |
| 2012/0165928 A1 | 6/2012 | Nitzan et al. |
| 2012/0265296 A1 | 10/2012 | McNamara et al. |
| 2012/0289882 A1 | 11/2012 | McNamara et al. |
| 2012/0290062 A1 | 11/2012 | McNamara et al. |
| 2012/0290077 A1 | 11/2012 | Aklog et al. |
| 2013/0030521 A1 | 1/2013 | Nitzan et al. |
| 2013/0041359 A1 | 2/2013 | Asselin et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0231737 A1 | 9/2013 | McNamara et al. |
| 2013/0267885 A1 | 10/2013 | Celermajer et al. |
| 2013/0281988 A1 | 10/2013 | Magnin et al. |
| 2014/0012181 A1 | 1/2014 | Sugimoto et al. |
| 2014/0012368 A1 | 1/2014 | Sugimoto et al. |
| 2014/0194971 A1 | 7/2014 | McNamara |
| 2014/0257167 A1 | 9/2014 | Celermajer |
| 2014/0277045 A1 | 9/2014 | Fazio et al. |
| 2014/0277054 A1 | 9/2014 | McNamara et al. |
| 2015/0039084 A1 | 2/2015 | Levi et al. |
| 2015/0119796 A1 | 4/2015 | Finch |
| 2016/0051800 A1 | 2/2016 | Vassiliades et al. |

FOREIGN PATENT DOCUMENTS

| | | |
|---|---|---|
| CN | 1582136 A | 2/2005 |
| CN | 1780589 A | 5/2006 |
| CN | 101035481 A | 9/2007 |
| CN | 101035488 A | 9/2007 |
| CN | 101292889 A | 10/2008 |
| CN | 101426431 A | 5/2009 |
| CN | 101579267 A | 11/2009 |
| EP | 1264582 A2 | 2/2002 |
| EP | 1470785 A1 | 10/2004 |
| EP | 1849440 A1 | 10/2007 |
| JP | 58-27935 U | 6/1983 |
| JP | 2003530143 | 10/2003 |
| WO | WO95/27448 A1 | 10/1995 |
| WO | WO98/08456 A1 | 3/1998 |
| WO | WO98/42403 A1 | 10/1998 |
| WO | WO2004/019811 A2 | 3/2004 |
| WO | WO2005/048881 A1 | 6/2005 |
| WO | WO2005/048883 A1 | 6/2005 |
| WO | WO2006/127765 A1 | 11/2006 |
| WO | WO2007/083288 A2 | 7/2007 |
| WO | WO2008/058940 A1 | 5/2008 |
| WO | WO2010/111666 A1 | 9/2010 |
| WO | WO2010/129511 A2 | 11/2010 |

OTHER PUBLICATIONS

Finch; U.S. Appl. No. 14/645,416 entitled "Devices and methods for treating heart failure," filed Mar. 11, 2015.

McNamara et al.; U.S. Appl. No. 14/878,710 entitled "Methods, systems, and devices for resizable intra-atrial shunts," filed Oct. 8, 2015.

Sugimoto et al.; U.S. Appl. No. 14/986,409 entitled "Devices and methods for retrievable intra-atrial implants," filed Dec. 31, 2015.

Celermajer et al.; U.S. Appl. No. 14/498,903 entitled "Apparatus and methods to create and maintain an intra-atrial pressure relief opening," filed Sep. 26, 2014.

Ad et al.; A one way valved atrial septal patch: A new surgical technique and its clinical application; The Journal of Thoracic and Cardiovascular Surgery; 111; pp. 841-848; Apr. 1996.

Althoff et al.; Long-term follow up of a fenestrated amplatzer atrial septal occluder in pulmonary arterial hypertension; Chest; 133(1); pp. 183-185; Jan. 2008.

Atz et al.; Preoperative management of pulmonary venous hypertension in hypoplastic left heart syndrome with restrictive atrial septal defect; the American Journal of Cardiology; 83; pp. 1224-1228; Apr. 15, 1999.

Bailey, Steven R.; Nanotechnology in prosthetic heart valves (presentation); 31 pgs.; 2005 (year of pub. sufficiently earlier than effective US filed and any foreign priority date).

Bolling, Steven; Direct flow medical—My valve is better (presentation); 21 pgs.; Apr. 23, 2009.

Cheatham, John P.; Intervention in the critically ill neonate and infant with hypoplastic left heart syndrome and intact atrial septum; Journal of Interventional Cardiology; 14(3); pp. 357-366; Jun. 2001.

Coselli, Joseph S.; No! Valve replacement: Patient prosthetic mismatch rarely occurs (presentation); 75 pgs.; Apr. 25, 2009.

Design News; Low power piezo motion; retrieved from the internet (http://www.designnews.com/document.asp?doc_id=229053 &dfpPParams=ht_13,aid_229053&dfpLayout=article); 3 pgs.; May 14, 2010.

Gaudiani et al.; A philosophical approach to mirral valve repair (presentation); 28 pgs.; Apr. 24, 2009.

Hijazi, Zayad M.; Valve implantation (presentation); 36 pgs.; May 10, 2007.

Larios et al.; The use of an artificial foraminal valve prosthesis in the closure of interatrial and interventricular septal defects; Chest; 36(6); pp. 631-641; Dec. 1959.

Leon, Martin B.; Transcatheter aortic valve therapy: Summary thoughts (presentation); 19 pgs.; Jun. 24, 2009.

Ling et al.; Implantable magnetic relaxation sensors measure cumulative exposure to cardiac biomarkers; Nat Biotechnol; 29(3); pp. 273-277; Mar. 2011.

McMahon, Jim; Piezo motors and actuators: Streamlining medical device performance; Designfax; Mar. 23, 2010; 5 pgs.; retrieved from the internet on Jul. 19, 2012 (http://www.designfax.net/enews/20100323/feature-1.asp).

Merchant et al.; Advances in arrhythmia and electrophysiology; implantable sensors for heart failure; Cir Arrhythm Electrophysiol; 3; pp. 657-667; Dec. 2010.

Moses, Jeffrey W.; The good, the bad and the ugly of transcatheter AVR (presentation); 28 pgs.; Jul. 10, 2009.

O'Loughlin et al.; Insertion of a fenestrated amplatzer atrial sestosotomy device for severe pulmonary hypertension; Heart Lung Circ.; 15(4); pp. 275-277; Aug. 2006.

(56) References Cited

OTHER PUBLICATIONS

Park et al.; Blade atrial septostomy: Collaborative study; Circulation; 66(2); pp. 258-266; Aug. 1982.

Pedra et al.; Stent implantation to create interatrial communications in patients with complex congenital heart disease; Catheterization and Cardiovascular Interventions; 47; pp. 310-313; Jan. 27, 1999.

Perry et al.; Creation and maintenance of an adequate interatrial communication in left atrioventricular valve atresia or stenosis; The American Journal of Cardiology; 58; pp. 622-626; Sep. 15, 1986.

Philips et al.; Ventriculofemoroatrial shunt: A viable alternative for the treatment of hydrocephalus; J. Neurosurg.; 86; pp. 1063-1066; Jun. 1997.

Physik Instrumente; Piezo for Motion Control in Medical Design and Drug Research (product information); Physik Instrumente (PI) GmbH & Co. KG; 22 pgs.; ©Nov. 21, 2010.

Roven et al.; Effect of compromising right ventricular function in left ventricular failure by means of interatrial and other shunts; Am J Cardiol.; 24(2); pp. 209-219; Aug. 1969.

RPI Newswire; Implantable, wireless sensors share secrets of healing tissues; RPI Newswire; 1 pg.; Feb. 21, 2012; retrieved from the internet on Jul. 18, 2012 (http://news.rpi.edu/update.do).

Sambhi et al.; Pathologic Physiology of Lutembacher Syndrome; Am J Cardiol.; 2(6); pp. 681-686; Dec. 1958.

Sommer et al.; Transcatheter creation of atrial septal defect and fontan fenestration with "butterfly" stent technique; Journal of the American college of Cardiology; 33(2); Suppl. A; 3 pgs.; Feb. 1999.

Stone, Gregg W.; Transcatheter devices for mirral valve repair, surveying the landscape (presentation); 48 pgs.; Jul. 10, 2009.

Stormer et al.; Comparative study of in vitro flow characteristics between a human aortic valve and a designed aortic valve and six corresponding types of prosthetic heart valves; Eur Surg Res; 8(2); pp. 117-131; 1976 (year of pub. sufficiently earlier than effective US filed and any foreign priority date).

Trafton, Anne; Detecting whether a heart attack has occurred; MIT News; 3 pgs.; Feb. 14, 2011; retrieved from the internet Sep. 20, 2014 (http://newsoffice.mit.edu/2011/cardiac-implant-0214).

Watterson et al.; Very small pulmonary arteries: Central end-to-side shunt; Ann. Thorac. Surg.; 52(5); pp. 1132-1137; Nov. 1991.

Webber, Ralph; Piezo Motor Based Medical Devices; Medical Design Technology; 5 pgs.; Apr. 2, 2009; retrieved from the internet on Jul. 19, 2012 (http://mdtmag.com/articles/2009/04/piezo-motor-based-medical-devices).

Forcucci et al.; U.S. Appl. No. 15/346,711 entitled "Retrievable devices for treating heart failure," filed Nov. 8, 2016.

\* cited by examiner

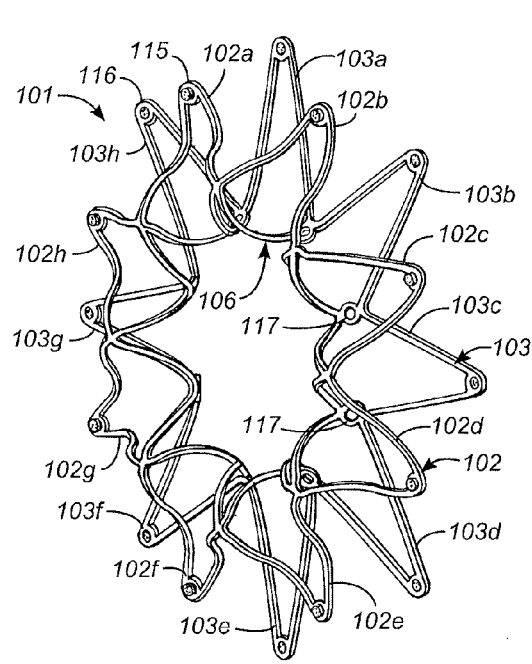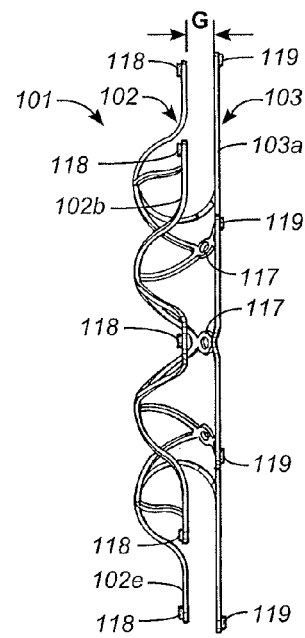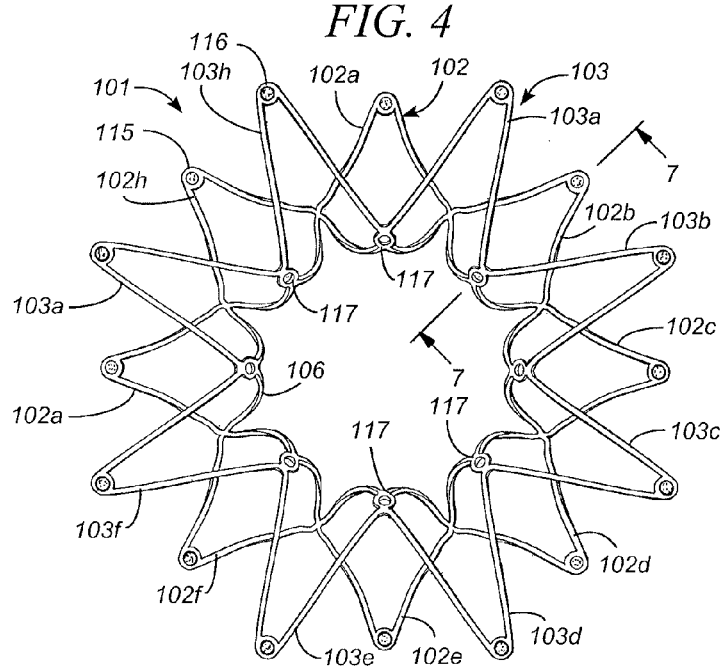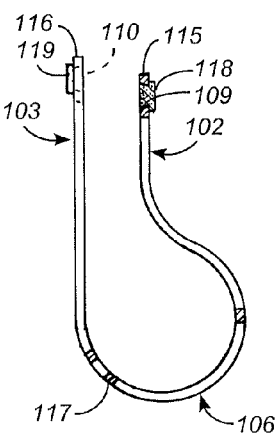
FIG. 4
FIG. 5
FIG. 6
FIG. 7

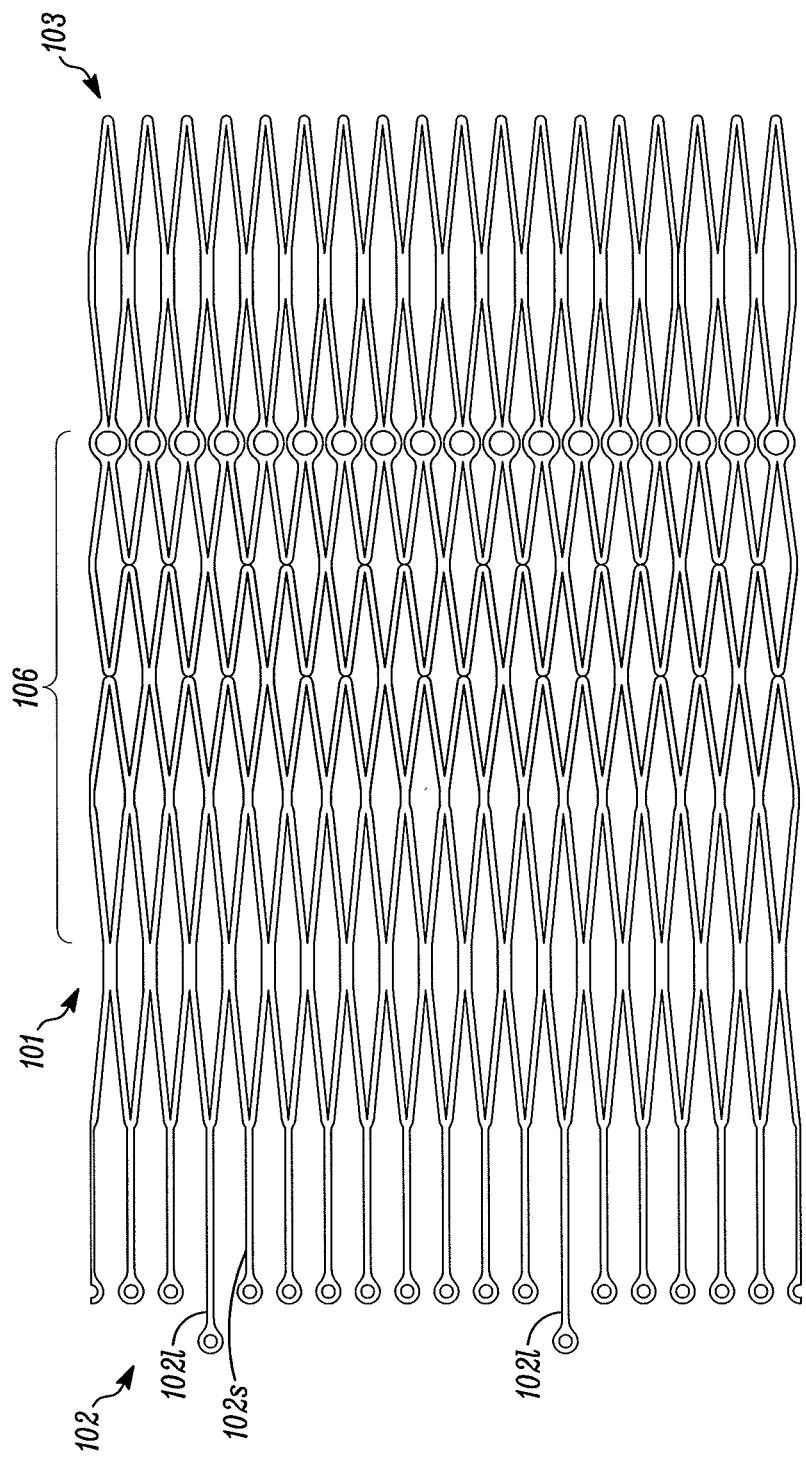

METHODS AND DEVICES FOR INTRA-ATRIAL SHUNTS HAVING ADJUSTABLE SIZES

CROSS REFERENCE TO RELATED APPLICATIONS

This application is a continuation-in-part of U.S. application Ser. No. 13/726,472, filed Dec. 24, 2012, which claims the benefit of U.S. Provisional Application No. 61/579,426, filed Dec. 22, 2011, and U.S. Provisional Application No. 61/659,520, filed Jun. 14, 2012. This application is also a continuation-in-part of U.S. application Ser. No. 12/848,084, filed Jul. 30, 2010, which claims the benefit of U.S. Provisional Application No. 61/240,085, filed Sep. 4, 2009, and is a continuation of U.S. application Ser. No. 12/719,843, filed Mar. 8, 2010, now U.S. Pat. No. 8,157,860. Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to devices and methods for treating heart failure. In particular, the invention relates to interatrial pressure vents, shunts and the like, which reduce elevated pressure on one side of the heart thus mitigating the symptoms that result, as well as placement devices, systems, and methods therefore.

BACKGROUND

Heart failure is a common and potentially lethal condition affecting humans, with sub-optimal clinical outcomes often resulting in symptoms, morbidity and/or mortality, despite maximal medical treatment. In particular, "diastolic heart failure" refers to the clinical syndrome of heart failure occurring in the context of preserved left ventricular systolic function (ejection fraction) and in the absence of major valvular disease. This condition is characterized by a stiff left ventricle with decreased compliance and impaired relaxation, which leads to increased end-diastolic pressure. Approximately one third of patients with heart failure have diastolic heart failure and there are very few, if any, proven effective treatments.

Symptoms of diastolic heart failure are due, at least in a large part, to an elevation in pressure in the left atrium. In addition to diastolic heart failure, a number of other medical conditions, including systolic dysfunction of the left ventricle and valve disease, can lead to elevated pressures in the left atrium. Increased left atrial pressure often causes acute or chronic breathlessness amongst other problems. In addition, a variety of heart conditions can lead to "right heart failure", which can result in enlargement of the liver (hepatomegaly), fluid accumulation in the abdomen (ascites) and/or swelling of the lower limbs.

Frequently, patients with diastolic heart failure experience breathlessness due, in part, to elevated pulmonary venous pressure. These patients often feel worse when supine than when sitting or standing, implying that small changes in pulmonary venous pressure have a pronounced effect on symptoms.

In the past, strategies have been described for the relief of high pressure in the right atrium, such as the creation of hole(s) in the native or surgically created septum between the left and right atria. These have been designed for the rare conditions of pulmonary hypertension or cavopulmonary connections for certain complex congenital heart diseases.

Accordingly, there exists a need for devices and methods to treat heart failure particularly diastolic and/or systolic failure of the left ventricle and its consequences.

Furthermore, there also still exists a need for devices to relieve high pressure in the left atrium and which will prevent or minimize the chance of the passage of thrombi, especially from the right atrium to the left atrium, and the resulting risk of systemic emboli.

SUMMARY OF THE DISCLOSURE

It is, therefore, a goal of this invention to effect a reduction in pulmonary venous pressure to ease symptoms of diastolic heart failure. It is a further goal of this invention to create a controlled vent between the left atrium and right atrium to allow a sufficient amount of blood to pass from the left atrium to the right atrium but minimize blood flow from the right atrium to the left atrium.

It is a further goal of this invention to create a controlled vent that will respond to pressure differences between the left and right atrium.

It is a further goal of this invention to provide an interatrial pressure venting device that prevents thrombi from entering the left atrium.

The present invention solves these and other needs by providing a venting device, which in some embodiments comprises a controlled opening or an extended tubular opening, between the left atrium and right atrium that allows an amount of blood to vent from the left heart to the right heart, thereby reducing left atrial pressure and the symptoms associated with diastolic heart failure.

Several unique intracardiac pressure vents, placement catheters, methods of placement and methods of treating heart failure are presented. The intracardiac pressure vents presented allow sufficient flow from the left atrium to the right atrium to relieve elevated left atrial pressure and resulting patient symptoms but also limit the amount of flow from the right atrium to the left atrium to minimize the potential for thrombi or other embolic material from entering the arterial circulation.

In addition, the intracardiac pressure vents presented solve the problem of controlling flow in one direction but minimizing flow in another direction with very low changes in pressure across the device.

Also, the intracardiac pressure vents presented solve the problem of reducing calcium deposition, protein deposition and thrombi formation in a low pressure environment.

Furthermore, the intracardiac pressure vents presented solve the problem of damage to the interatrial septum as well as the rest of the left atrium from excessive pressure against the wall which can cause injury to the tissue and possibly adverse reaction by the patient or compromised function to the interatrial pressure vent.

In addition, atrial arrhythmias are frequently seen in patients with heart failure and may, in part, be caused by chronically elevated left atrial pressure. Therefore, relief of elevated left atrial pressure may lead to reduction of atrial fibrillation.

The present invention provides interatrial pressure vents, placement catheters, methods for placing a device in the interatrial septum within the heart of a patient and methods for treatment of the symptoms of heart failure, particularly diastolic heart failure.

In embodiments, the interatrial pressure vent comprises a body assembly and a flow control element; the body assembly comprises a flexible, substantially open mesh adapted for use in a patient. The flow control element attaches to at least one point of the body assembly and the flow control element provides greater resistance to flow in one direction than it does in another direction.

In embodiments, the interatrial pressure vent comprises a body assembly and a flow control element; the body assembly comprises a flexible, substantially open mesh adapted for use in a patient. The flow control element attaches to at least one point of the body assembly and is at least partially open to flow when there is no pressure differential across the flow control element.

In embodiments, the interatrial pressure vent comprises a body assembly and a flow control element; the body assembly comprises a core segment and at least one flange segment; the flange segment is integral with, or attached to at least one point adjacent to, an end of the core segment; the flange segment extends radially outward from the center longitudinal axis of the core segment. The flow control element attaches to at least one point along the core segment and the flow control element provides greater resistance to flow in one direction than in the opposite direction.

In embodiments, the interatrial pressure vent comprises a body assembly and a flow control element; the body assembly comprises a substantially cylindrical core segment and at least one flange segment; the flange segment is integral with, or attached at least to one point adjacent to, an end of the core segment; the flange segment extending radially outward from the center longitudinal axis of the core segment. The flow control element attaches to at least one point along the core segment and the flow control element provides greater resistance to flow in one direction than another direction.

In embodiments, the interatrial pressure vent comprises a body assembly and a flow control element. The body assembly comprises a substantially cylindrical core segment and at least one flange segment integral with, or attached to at least one end of, the core segment; the flange segment extending radially outward from the axis of the core segment. The flow control element attaches to at least one point along the core segment and the flow control element is at least partially open to flow when there is no pressure differential across the flow control element.

In embodiments, the interatrial pressure vent comprises a body assembly and a flow control element. The body assembly comprises a substantially cylindrical core segment and at least one flange segment integral with, or attached to at least one end of, the core segment and extending away from the axis of the core segment. The flow control element attaches to at least one point along the flange assembly and provides greater resistance to flow in one direction than the other direction.

In embodiments, the interatrial pressure vent comprises a body assembly and a flow control element. The body assembly comprises a substantially cylindrical core segment and at least one flange segment integral with, or attached to at least one end of, the core segment and extending away from the axis of the core segment. The flow control element attaches to at least one point along the flange assembly and is at least partially open to flow when there is no pressure differential across the flow control element.

In embodiments, the interatrial pressure vent comprises a body assembly and a flow control element. The body assembly comprises a substantially cylindrical core segment and at least one flange segment integral with, or attached to at least one end of, the core segment and extending away from the axis of the core segment. The flow control element extends at least partly onto the flange assembly and creates a sealable contact to the atrial septum and provides greater resistance to flow in one direction than the other direction.

In embodiments, the interatrial pressure vent comprises a body assembly and a flow control element. The body assembly comprises a substantially cylindrical core segment and at least one flange segment integral with, or attached to, at least one end of the core segment and extends away from the axis of the core segment. The flow control element attaches to the flange assembly and creates a sealable connection to the atrial septum and is at least partially open to flow when there is no pressure differential across the flow control element.

In embodiments, the interatrial pressure vent comprises a body assembly with a first end and a second end and a flow control element; the body assembly comprises a core segment including at least one flange segment integral with, or attached to, at least one point adjacent to the first end of the core segment and at least one other flange segment integral with, or attached to, at least one point adjacent to the second end of the core segment; the flange segments extending radially outward from the center longitudinal axis of the core segment and the flange segments oriented so they do not oppose each other when deployed. The flow control element attaches to at least one point along the core segment and the flow control element provides greater resistance to flow in one direction than it does in another direction.

In embodiments, the interatrial pressure vent comprises a body assembly with a first end and a second end and a flow control element; the body assembly comprises a core segment including at least one flange segment integral with, or attached to, at least one point adjacent to the first end of the core segment and at least one other flange segment integral with, or attached to, at least one point adjacent to the second end of the core segment; the flange segments extending radially outward from the center longitudinal axis of the core segment and the flange segments oriented so they do not oppose each other when deployed. The flow control element attaches to at least one point along the core segment and the flow control element is at least partially open to flow when there is no pressure differential across the flow control element.

In embodiments, the interatrial pressure vent comprises a body assembly with a first end and a second end and a flow control element comprised of at least one leaflet; the body assembly comprises a substantially cylindrical core segment and a number of flange segments integral with, or attached to, at least one point on each side of the body segment and extending radially outward from the center longitudinal axis of the core segment; the number of flange segments on either side of the core segment being a whole multiple of the number of leaflets.

In embodiments, the interatrial pressure vent comprises a body assembly with a first end and a second end and a flow control element comprised of at least one leaflet; the body assembly comprises a substantially cylindrical core segment and a number of flange segments integral with, or attached to, at least one point on each side of the body segment and extending radially outward from the center longitudinal axis of the core segment; the number of flange segments being a whole multiple of the number of leaflets. The flow control element attaches to at least one point of the body assembly and the flow control element provides greater resistance to flow in one direction than another direction.

In embodiments, the interatrial pressure vent comprises a body assembly with a first end and a second end and a flow control element comprised of at least one leaflet; the body assembly comprises a substantially cylindrical core segment and a number of flange segments integral with, or attached to, at least one point on each side of the body segment and extending radially outward from the center longitudinal axis of the core segment; the number of flange segments being some multiple of the number of leaflets. The flow control element attaches to at least one point of the body assembly and is at least partially open to flow when there is no pressure differential across the flow control element.

In embodiments, an implant system comprises an interatrial pressure vent and placement catheter for treating heart failure. The implant system is comprised of a body assembly and a flow control element. The body assembly is comprised of a substantially cylindrical core segment and at least one flange segment integral with, or attached to, at least one end of the core segment and extending radially away from the core segment.

The flow control element is attached to at least one point along the core segment and provides greater resistance to flow in one direction than the other direction. The placement catheter is comprised of an inner shaft and an outer shaft. The inner shaft comprises an elongate tube and a handle component. The inner shaft also contains at least one lumen that extends along at least part of the length of the inner shaft. The outer shaft comprises an elongate hollow tube or sheath and a different handle component that slideably interfaces with the first handle component.

In embodiments, an implant system comprises and interatrial pressure vent and placement catheter for treating heart failure. The implant system is comprised of a body assembly and a flow control element. The body assembly is comprised of a substantially cylindrical core segment and at least one flange segment integral with, or attached to, at least one end of the body assembly and extending radially away from the body segment. The flow control element is attached to at least one point along a flange and provides greater resistance to flow in one direction than the other direction. The placement catheter is comprised of an inner shaft and an outer shaft. The inner shaft comprises an elongate tube and a handle component. The inner shaft also contains at least one lumen that extends along at least part of the length of the inner shaft. The outer shaft comprises an elongate hollow tube (or sheath) and a different handle component that slideably interfaces with the first handle component.

In embodiments, an implant system comprises and interatrial pressure vent and placement catheter for treating heart failure. The implant system is comprised of a body assembly and a flow control element. The body assembly is comprised of a substantially cylindrical core segment and at least one flange segment integral with, or attached to, at least one end of the body assembly and extending radially away from the body segment. The flow control element is attached to at least one point along a flange and provides greater resistance to flow in one direction than the other direction. The placement catheter is comprised of an inner shaft and an outer shaft. The inner shaft comprises an elongate tube with at least one flange or circumferential groove formed in the outer diameter and a handle component. The inner shaft also contains at least one lumen that extends along at least part of the length of the inner shaft. The outer shaft comprises an elongate hollow tube (or sheath) and a different handle component that slideably interfaces with the first handle component.

In other embodiments, the invention comprises a device for treating a heart condition in a patient comprising a body element having a core segment defining a passage, a first annular flange comprising a plurality of flange segments, and a second annular flange comprising a plurality of flange segments. In embodiments, at least a portion of one of the flange segments is either more or less flexible than the remaining portion of the flange segment or other portions of the body element, including but not limited to the cylindrical core segment.

In other embodiments, the device comprises a third or intermediate annular flange for better adherence to the septal wall.

In other embodiments, the device comprises a flow control element configured to aim the flow of blood in a desired direction.

In other embodiments, the invention is configured to be more easily retrieved during deployment. Such embodiments can include among other elements a at least one extended flange segment in one of the annular flanges that is able to be retained within a placement catheter when the other portions of the device are deployed.

In embodiments, the method of placing the interatrial pressure vent into position may comprise a sequence of steps to locate and gain access to a vascular channel leading to the heart, placing an introducer catheter via this channel into one of the atriums of the heart, locating the interatrial septum between the left and right atriums, creating an opening in the interatrial septum, advancing a placement catheter containing an interatrial pressure vent into one of the atriums and then through the opening created in the interatrial septum between the right and left atriums, and then controllably deploying the interatrial pressure vent so it is securably connected to the interatrial septum.

Deployment of the interatrial pressure vent preferably occurs in a series of steps comprising first advancing the placement catheter through the septal opening, second deploying a first flange, third retracting the placement catheter to position the first flange against the septal wall, and fourth deploying a second flange on the other side of the septal wall from the first flange.

In embodiments where the device disclosed herein is implanted into the atrial septum, the introducer catheter may be placed through the inferior vena cava via a femoral vein to the right atrium.

Other pathways are available including placing the introducer catheter through the superior vena cava via a jugular vein; through the aorta, via a femoral artery, past the aortic valve and into the left atrium; through the aorta, via a brachial artery, past the aortic valve and into the left atrium; through the superior vena cava via a basilica vein; through the superior vena cava via a cephalic vein; intraoperatively, through an opening created in the right atrium either for this reason or during a procedure performed for some other purpose; intraoperatively through an opening created in the left atrium either for this reason or during a procedure performed for some other reason; or via a guidewire that is positioned through the interatrial septum and located in the pulmonary artery.

Regarding the placement catheter, in some embodiments the placement catheter is designed to function as the introducer catheter and the placement catheter, eliminating the need for a catheter exchange. While in other embodiments, the introducer catheter, the placement catheter, or both are constructed to be exchanged over only part of their length to avoid the necessity of handling a guidewire that is at least twice as long as the catheter. Still in other embodiments, the introducer catheter or the placement catheter, or both has a pre-shaped curve to enable orientation of the placement catheter substantially orthogonal to the septal wall. The catheter may be curved between 30° and 45° away from the catheter axis at a point between 5 and 15 centimeters away from the distal end of the placement catheter.

In embodiments of the invention where the inventive device is to be placed in the atrial septum, an opening in the septum can be performed using the introducer catheter in a separate procedure from the interatrial pressure vent placement procedure. Access through the opening can be maintained via a wireguide positioned in the right atrium or the pulmonary artery. The opening can be formed using the placement catheter via a distal tip segment that is part of the placement catheter.

The opening may be predilated using a balloon or other dilating device either as part of the procedure described or as a separate procedure.

In another aspect, the opening is formed and dilated as part of a single, unified procedure with the interatrial pressure vent placement procedure. This may be accomplished by integrating a balloon or other dilating component as part of the placement catheter and dilating the opening as part of placing the interatrial pressure vent. For example, this could be accomplished using a balloon that can be folded to achieve a small loaded profile and will have a suitable pressure capacity and suitable durability to dilate the septum opening and the interatrial pressure vent together.

The opening that is formed in the interatrial septum may be formed by pushing a catheter tip through the septum at the location of septum primum. Because this septum is normally very thin, the distal tip may be pushed directly through without significant force.

In an alternate method, the opening in the interatrial septum can be formed with a cutting tool that is advanced through the introducer catheter or the placement catheter. The tool preferably comprises a blade and a shaft. The blade contains at least two surfaces and one edge. The edge is sharpened and formed at an angle so that the blade slices as it is advanced into and through the septum.

In yet another method, the opening in the interatrial septum can be formed with a cutting tool that is advanced through the introducer catheter or the placement catheter. The tool preferably comprises a blade and a shaft. The blade contains at least two surfaces and two separate edges that are sharpened at an angle so that the blade slices as it is advanced into and through the septum and the septum is cut generally in an x shaped opening.

In yet another method, the opening in the interatrial septum can be formed with a punching tool that is advanced through the introducer catheter or the placement catheter. The punching tool preferably comprises a cutting assembly and a shaft. The cutting assembly preferably comprises a hollow, conical shape with a sharpened edge along the base circumference. The cutting assembly is connected at least to one point on the shaft and is generally oriented so the apex of the cone is pointed away from the shaft.

In one method, the cutting assembly can be operated by advancing the conical assembly through the interatrial septum and then pulling it back to form an opening that is generally circular.

In another method, the cutting assembly can be operated by advancing the conical assembly through the interatrial septum and then rotating it as it is pulled pack to create a circular cutting action against the interatrial septum.

In another embodiment, the cutting tool can be formed of at least one cutting member and one shaft. The cutting member is connected at least to one point along the shaft and the other end of the cutting member is adjustably positioned so it can lay alongside the shaft or at some angle away from the shaft. To place the cutting tool, the cutting member is placed alongside the shaft and then advanced through the septum. Then the cutting member would be adjusted to a second position, radially further away from the shaft than the first position, and the shaft would be positioned so the cutting member exerts lateral stress against the septum. The cutting member could be designed to slice the septum in this manner. In another method, the cutting tool could be rotated once the shaft and cutting member were repositioned so the slicing motion would cut a generally circular hole through the septum.

In embodiments, the cutting member is round wire.

In another embodiment, the cutting member can be connected to one output of a power supply, capable of supplying a suitable signal to the cutting member, the other output of which is connected to a ground plate placed against the patient's skin. An appropriate electric potential can be placed between the cutting member and ground plate to cause a concentrated current density near the wire to aid in cutting through the septum tissue.

In another embodiment, the cutting member is a section of tubing sliced lengthwise and appropriately formed to create a cutting edge. During placement, the cutting member is controllably positioned to lie against the shaft as the shaft is advanced through the placement catheter and through the opening created in the interatrial septum. Once positioned, the placement catheter is retracted and the shaft is positioned within the septum. Once positioned in this manner, the cutting member can be controllably adjusted to a second position, radially further away from the shaft than the first position, and the shaft positioned so the cutting member exerts lateral stress against the septum.

In yet another method, an opening is created in the interatrial septum which is smaller than the diameter of the outer surface of the body of the interatrial pressure vent according to the present invention such that, when the interatrial pressure vent is initially deployed within the interatrial septum, there is some compression from the septum against the body of the interatrial pressure vent.

Referring now to the placement catheter used to position and controllably place the interatrial pressure vent; in one aspect, the placement catheter consists of an inner member and an outer member.

In embodiments, the outer member is comprised of a tubing member and a first handle component, the outer shaft is less than about 16 F in diameter and formed of a material suitably smooth and resilient in order to restrain the stowed interatrial pressure vent and allow smooth stowing and deployment, such as PTFE, FEP, Tefzel, PVDF, HDPE or other suitable materials.

In embodiments, the inner member is comprised of at least one tubing member with an inner lumen through at least part of the tubing member, and a second handle component attached to the proximal end, with the second handle component slideably attached to the first handle component.

In embodiments, the handle components are interconnected via an inclined, helical lever to enable advancement of the inner member relative to the outer member by rotating the outer shaft handle while holding the inner shaft handle.

In embodiments, the handle components comprise a locking mechanism that prevents the handle component from moving in relationship to each other beyond a certain predetermined length.

In embodiments, the handle components contain at least two locking mechanisms that prevents the handle component from moving in relationship to each other beyond two different predetermined length.

In embodiments, the inner member contains a stiffening element adjacent to the distal area.

In embodiments, a system for treating heart failure in a patient consists of an interatrial pressure vent and placement device. The interatrial pressure vent comprises a body section and a flow control element. The body section comprises a core section and at least one flange segment. The flange segment comprises a midsection adjacent to the body and an end section that has a greater wall thickness than the midsection. The placement device comprises an inner shaft and an outer shaft. The inner shaft comprises an outside diameter and an internal lumen extending at least partly toward the proximal end from the distal end. The outer shaft contains an outside diameter and an inside diameter. The inner shaft contains a necked portion or circumferential groove along at least part of its length of smaller diameter than at least a portion of the inner member distal to the necked portion; the space formed between the outside of the necked portion and the inside of the outer shaft being sufficient to contain a folded or otherwise compressed interatrial pressure vent of the present invention and the space formed between the outside of the non-necked portion and the inside of the outer shaft being insufficient to contain the interatrial pressure vent.

In embodiments, a system for treating heart failure in a patient consists of an interatrial pressure vent and placement device. The interatrial pressure vent comprises a body section and a flow control element. The body section comprises a core section and at least one flange segment. The flange segment comprises a midsection adjacent to the body and an end section located radially further away than the midsection and with a larger dimension in the radial direction than the midsection. The placement device comprises an inner shaft and an outer shaft. The inner shaft contains an outside diameter and an internal lumen extending at least partly toward the proximal end from the distal end. The outer shaft contains an outside diameter and an inside diameter. The inner shaft contains a first necked portion or circumferential groove comprising a length and a diameter; the diameter of the first necked portion of the inner shaft being smaller than at least a portion of the inner member distal to the necked portion and the inner shaft also containing a second necked portion, proximal to the first necked portion and of a length sufficient for containing end section of the flange segment and a diameter smaller than the first necked portion; the space formed between the outside of the first necked portion and the inside of the outer shaft being sufficient to contain the folded or otherwise compressed interatrial pressure vent of the present invention except for the end section of the flange segment; the space formed between the outside of the non-necked portion and the inside of the outer shaft being insufficient to contain the interatrial pressure vent and the space formed between the outside of the second necked portion and the inside of the outer shaft being sufficient to contain the end section of the flange segment.

In another aspect, the inner member comprises a first necked portion along at least part of its length of smaller diameter than at least a portion of the inner member distal to the first necked portion and second necked portion, along a second part of its length proximal to the first necked portion and smaller than the first necked portion. The space between the outside of the necked portion and the inside of the outer sheath.

Referring now to the body assembly of the interatrial pressure vent, in one aspect, the body comprises a core segment and at least one flange segment.

In embodiments, the body assembly comprises a core segment; a first flange comprising at least one flange segment at one end of the core segment; and a second flange comprising at least one flange segment at the opposite end from the first flange of the core segment.

In embodiments, the body assembly comprises a core segment, comprising a self expanding mesh; a first flange, at one end of the core segment; and a second flange at the opposite end of the core segment from the first flange.

In embodiments, the body assembly is comprised of a core segment, comprising a balloon expandable mesh; a first flange at one end of the core segment; and a second flange at the opposite end of the core segment from the first flange.

In embodiments, the body assembly is comprised of a core segment; a first flange at one end of the core segment; and a second flange at the opposite end of the core segment from the first flange; each flange oriented to extend substantially radially outward relative to the center axis the flange segment.

In embodiments, the body assembly is comprised of a core segment; a first flange at one end of the core segment; and a second flange at the opposite end of the core segment from the first flange; each flange oriented to extend substantially radially outward from the core segment; and at least one flange extending beyond 90° relative to the center axis of the core segment.

In embodiments, the body assembly is comprised of a core segment; a first flange at one end of the core segment; and a second flange at the opposite end from the first flange of the core segment; each flange oriented to extend substantially radially outward from the core segment; the first flange formed with a smaller radius of curvature than the second flange.

In embodiments the interatrial pressure vent comprises a flow control element biased to allow flow from one atrium of a patient to the other atrium of the patient with lower resistance than in the reverse direction.

In embodiments the interatrial pressure vent comprises a flow control element biased that remains at least partially open when there is no pressure differential across the vent.

In embodiments, the interatrial pressure vent comprises an integral filter to prevent embolic particles larger than about 2 mm from passing beyond the filter in the direction of flow.

In other embodiments, the interatrial pressure vent comprises a tubular flow element which extends a distance beyond the core segment so as to prevent embolic particles from entering the left atrium.

In embodiments, the interatrial pressure vent comprises at least one movable flap that responds to pressure changes between the right and left atrium.

In embodiments, the body assembly may be constructed from preformed wire braid. The wire braid may be formed from nitinol with a martensite/austenite transition temperature is below 37° C. so it remains in its superelastic, austenitic phase during use. The transition temperature is below about 25+/−5° C. The wire should have a diameter of at least about 0.0035 (about 2 lbs of breaking strength at 200 ksi tensile). The wire should have a very smooth surface to reduce thrombogenicity or irritation response from the tissue. The surface finish may be 63 uin RA or better. This surface may be obtained either by mechanical polishing, by electropolishing or a combination. In embodiments, the surface may be cleaned with detergents, acids and/or solvents to remove residual oils or contamination and then controllably passivated to insure minimal corrosion.

In embodiments, the body assembly may be formed from grade 1 titanium. In embodiments, the body may be formed of grade 6 titanium. In embodiments, the body may be formed of grade 9 titanium. In embodiments, the body may be formed of 316L stainless steel. In embodiments, the body may be formed of 416L stainless steel. In embodiments, the body may be formed of nitinol or Elgiloy. In embodiments, the body is formed of platinum iridium. In embodiments, the body may be formed of a cobalt chromium alloy. In embodiments, the body may be formed of MP35N. In embodiments, the body may be formed of Vitalium (TRADEMARK). In embodiments, the body may be formed of Ticonium (TRADEMARK). In embodiments, the body may be formed of Stellite (TRADEMARK). In embodiments, the body may be formed of tantalum. In embodiments, the body may be formed of platinum. Materials disclosed with reference to the body or any component of the device disclosed herein are not meant to be limiting. The skilled artisan will appreciate that other suitable materials may be used for the body or any other component of the device.

In embodiments, the body assembly is preferably formed from a length of cylindrical tubing that is precut with slots at specific locations and then formed in a series of processes to produce a shape suited for the purpose of containing a flow control element within the interatrial septum.

As an example, a first process might be to stretch the cylinder to expand its internal diameter to a uniform target dimension. This can be done with a balloon or a standard tubing expander consisting of a segmented sleeve and tapered conical inserts that increase the diameter of the sleeve when the cones are advanced toward the center. In order that the shape of the stretched tubing be preserved, the cylinder should be annealed while held into this stretched shape by heating it beyond 300° to 600° for at least about 20 minutes to allow the internal stresses to be relieved. A second process might be to form one flange end shape using a similar process as the first process but using a tool shape specially designed for the first flange shape. A third process might be to form the second flange end shape using a similar process as the first process but using a tool specially designed for the third flange shape. These shapes must be annealed using a similar process as the first shape, either in separate steps or altogether.

In embodiments, the internal diameter of the finished interatrial pressure vent is larger than about 5 mm to enable adequate venting of the left atrium and minimize damage to blood components from excessive shear stress, but enabling the interatrial pressure vent to stow in a placement catheter of smaller than about 14 F.

In embodiments, the flow control element opening is at least about 50 sq. mm.

In embodiments, the flow control element opening is 50 sq.mm.+−10 sq. mm.

In another embodiment, the cylindrical section is formed with an inside diameter of between 3 and 15 mm.

The internal diameter of the body segment is preferably a constant dimension along the center, longitudinal axis of the interatrial pressure vent and is long enough to isolate the flow control element from deflection or damage as a result of contact with other structural elements of the heart.

In embodiments, the body segment is formed into a substantially toroidal shape, the inner diameter tapering down and then up again from one side of the implant to the other.

In embodiments, the length of the body section may be about 4 mm.

In embodiments, the length of the body section may be between about 3 mm and about 40 mm.

In yet other embodiments, the flange segment may comprise at least a single loop which is oriented to the cylindrical shape by at least about 90° relative to the central axis of the cylinder and projected outward to a distance away from the center axis of greater than the opening in the atrial septum but at least about 3 mm further than the diameter of the inner cylinder.

In embodiments, the flange segment is formed of multiple struts that extend radially outward, with respect to the center aspect of the cylinder.

In embodiments, the flange struts each comprise a substantially triangular shape that is wider adjacent to the body section than at the outer edge of the strut.

In embodiments, the flange struts comprise a substantially triangular shape that is wider adjacent to the body section than at the outer edge of the strut and contains an integral hole at the outer edge for containing a radiopaque marker.

In embodiments, the flange struts comprise a substantially triangular shape that is wider adjacent to the body section than at the outer edge of the strut and whose outer edge is rounded to reduce trauma against the tissue it contacts.

In embodiments, the flange struts are formed from a single beam of material that project outward from the center longitudinal axis of the body section.

In embodiments, the flange segment is formed of spiral shaped flange struts that are coplanar and substantially orthogonal to the central axis of the cylinder.

In embodiments, the flange segment is formed of at least one looping member that attaches to at least one portion of the body section.

In embodiments, the flange is preferably formed to automatically recover substantially to its preformed shape following partial deployment of the interatrial pressure vent from the placement catheter. In this manner, the interatrial pressure vent will resist being pulled back through the septal opening.

In embodiments, the flow control element device may be a tissue valve, a synthetic valve or a combination. The flow control element can be formed from animal or human tissue, such as bovine pericardial tissue. The procedures for obtaining these tissues and preparing them for use as implanted valve components are well known to those skilled in the art. The flow control element could be a trileaflet valve, or also a bileaflet valve, or also a simple flap valve. The flow control element could also be a ball and socket valve, a duckbill valve, a butterfly valve, or any other valve component known to those skilled in the art.

In embodiments, the flow control element can be biased by adding a separate component that is attached to at least one point along the body or flange segment and contacts against at least one point of the flow control element surface at least at some point during its duty cycle. The component can be preformed to controllably affect the flow control element behavior. For example, in one embodiment, the flange segment can be a looped wire formed from nitinol and connected to the body section and cantilevered against the surface of the flow control element facing the left atrium and formed so that the surface of the flow control element is biased to be slightly open when the pressure is equal in the left atrium and right atrium. Biasing can also be accomplished by varying the stiffness of the material of the valve or components thereof.

In embodiments, a flange segment could be formed out of a helical winding of nitinol, with a core wire to connect one end of the flange segment to the other end.

In embodiments, the flow control element can be pre-shaped to resist moving against pressure in one direction.

In embodiments, the flow control element could be biased to remain open at a predetermined pressure, or at a neutral pressure.

In embodiments, the interatrial pressure vent consists of a body section and a flow control element; the body section comprising a cylindrical core segment and two flanged end sections; the flow control element being sealably secured to at least three points along the body section; the flanged end sections each comprising at least one flange segment that extends radially outward from the body section; the flow control element comprising at least one movable element that allows fluid passage in one direction with lower resistance than another direction.

In embodiments, the body section is elliptical in shape, or cylindriod and designed to offset asymmetric stress created by a linear septal opening.

In embodiments, the formed metal flange segments consist of at least two flange segments, with at least one on each side of the septum.

In embodiments, the flange segments are positioned so they do not pinch the septum between them, thereby reducing possible pressure necrosis.

In embodiments, the flange segments are shaped so the wall thickness perpendicular to the septum is less than the wall thickness parallel to the septum, thereby increasing flexibility without decreasing strength.

In embodiments, the flange segments are formed so the radius of curvature at the end is greater than about 0.03 inches.

In embodiments, there is a radiopaque marker, preferably tantalum or platinum alloy, formed around, or integral with, the flange segment end to increase radiopacity and increase the area of contact between the flange segment and septum.

In embodiments, the flange on the left atrium side of the septum is bent at a shorter radius of curvature than the right atrium side.

In embodiments, the flange on one side of the interatrial septum is formed to return to greater than a 90° angle relative to the axis of the center cylinder.

In embodiments, holes are preformed at a location along the cylindrical section for suture sites for securing the valving device.

In general, the present invention includes treating heart disease by reducing both left atrial and pulmonary venous pressure. To this end, devices and methods are disclosed herein which may include the creation of a pressure relief shunt in the atrial septum or the placing of a device having a changeable hydraulic diameter into an already existing aperture in the atrial septum. Furthermore, devices and methods are disclosed herein which allow for adjusting the pressure relief shunt in response to the natural progression of the patient during the course of treatment. Additionally, devices and methods are disclosed which provide a treatment which may be adjusted to or which automatically adjusts to the changing conditions in the body as a result of the creation of the pressure relief shunt or the presence of the extant atrial septal aperture. Furthermore, devices and methods are disclosed herein which mitigate the risk of acute worsening of heart failure following the creation of a pressure relief shunt or of an extant atrial septal aperture by allowing for gradual increase in the hydraulic diameter of an implanted device after implantation. Devices and methods are disclosed herein which significantly mitigate the risk of later development of pulmonary hypertrophy by implanting a device which gradually decreases hydraulic diameter in size over time or in response to the natural hemodynamic changes in the heart.

In some embodiments of the present invention, an implantable shunting device is provided. The inventive device includes a pair of anchors, each comprising a plurality of segments, that are adapted to hold the device in place within a membrane wall, e.g. the atrial septum, and a shunting section adapted to permit fluid flow across the membrane wall first at first rate and then at a second rate at a later selectable time.

In some embodiments, the implantable shunting device is adapted to be manually adjusted to change the rate of fluid flow therethrough. For example, the inventive device may include an element which causes the hydraulic diameter of the shunting section to be manually alterable. Such elements may include a coil which may be incrementally wound, stretched, and/or compressed to selectively alter its hydraulic diameter. Such elements may include a tube that can be plastically deformed to alter its hydraulic diameter.

In some embodiments, the implantable shunting device is adapted to automatically change the rate of fluid flow therethrough. For example, the inventive device may have a first configuration which allows a predetermined flow rate to communicate from a high pressure region to a low pressure region across a membrane wall and be adapted to transform over a predetermined period of time into one or more other configurations in order to allow a different flow rate or different flow rates to communicate from the high pressure region to the low pressure region. The transformations may be gradual or may occur in discrete steps or may be a combination of gradual change with abrupt changes. The flow rate changes may be positive or negative or may alternate between the two.

In some embodiments, the implantable shunting device is to permit manual adjustment of the fluid flow rate through the device. For example, in some embodiments, the inventive device includes a hollow tubular body and a number of septal anchoring members, which anchor the inventive device to the atrial septum. The tubular body may be configured with an originally-deployed diameter (a first diameter) which may be expected to provide an efficacious treatment for an average patient. Alternatively, the first diameter of the tubular body may initially be undersized such that an effective treatment may be achieved in some subset of patients while the risk of acute worsening of heart failure following the implantation of the shunt is substantially decreased among all patients. The inventive device is further configured to be manually expanded or contracted by an adjustment device to second, third, fourth, . . . , etc. diameters (also referred to herein as "subsequent diameters"). The inventive device may include interlocking features which maintain the internal diameter that is set by the adjustment device. Alternatively, the tubular body of the inventive device may be made from an elastically deformable, heat setting, pressure-sensitive, or otherwise malleable material such that the diameter of the device remains stable after being set by the adjustment device.

In some embodiments, the inventive device includes an elongate tubular body, an internal member having an orifice, and a number of anchoring members for anchoring the tubular body to the atrial septum. The tubular body further includes an internal fastening feature which releasably clasps the internal orifice-containing shunt member. The internal orifice-containing member has an internal diameter which is configured to allow a therapeutic amount of blood to flow through the shunt. The internal member may be released from the fastening feature of the tubular body with a special retrieval tool and may then be repositioned or replaced with another internal shunt member. The replacement internal shunt member may feature a substantially larger or substantially smaller internal diameter, thus causing the device to have a different subsequent diameter than the first diameter. This replacement of the internal member may therefore be used to adjust the amount of blood flow through the shunt in order to respond to hemodynamic changes in the heart.

In some embodiments, the inventive device including a tubular body and a number of anchoring members is disclosed, where the tubular body may be configured such that its first diameter initially allows only a small volume of blood to shunt from the left atrium to the right atrium. The tubular body may then be designed to gradually expand over the course of days, weeks, or months, to subsequent diameters that allow a larger volume of blood to pass through the shunt. The shunt may be configured so that the internal portion or orifice will expand to a predetermined final subsequent diameter in order to allow a therapeutic amount of blood flow through the shunt. In such embodiments, the orifice of the inventive device may be configured to expand slowly so that the risk of acute worsening of heart failure that may be caused by a sudden hemodynamic change is substantially reduced.

In some embodiments, the inventive device includes a tubular body and a number of anchoring members and is configured to open to an internal diameter that allows sufficient blood to flow through the shunt in order to reduce the left atrial and pulmonary venous pressure. The tubular body may be configured such that over time the internal diameter of the shunt gradually contracts. The internal diameter of the inventive device may be designed to shrink to a predetermined final diameter. The predetermined final diameter may be sized to allow some clinically relevant blood flow through the shunt while simultaneously eliminating the risk of developing hypertrophic pulmonary arteries. Alternatively, the inventive device may be configured such that given enough time the internal diameter becomes completely occluded and blood flow through the shunt is prevented.

In some embodiments, the inventive device featuring a tubular body and a number of anchoring members may be configured to, at first, gradually open the first internal diameter of the shunt and then much later gradually close the subsequent internal diameter of the shunt. The gradual shrinking or expanding of the inventive device is used to control the amount of blood through the shunt in anticipation of the hemodynamic changes that occur over time due to the progression of heart failure and due to the creation of a pressure relief shunt. In still other embodiments the gradual opening or closing of the inventive device may include prolonged periods of static blood flow. For example, the inventive device may be implanted with a small diameter, then over time expand to a second larger diameter and remain there for some period of time. The delay may allow for additional testing or observation by health care personal. After the static delay period the inventive device may be allowed to further expand to a still larger third diameter.

In some embodiments of the present invention, the inventive device including a tubular body and a number of anchoring members may be implanted into an atrial septum. The tubular body of the inventive device includes an anchoring or clasping feature which can be used by a physician to close the inventive device if desired.

In some embodiment, an adjustable intra-atrial shunt includes a retainer having a plurality of struts and a plurality of apices joining the struts to form a generally cylindrical body having a left retaining flange and a right retaining flange, the tubular body adapted to fit within a wall of an atrial septum, the left retaining flange adapted to fit within a left atrium of a heart and the right retaining flange adapted to fit within a right atrium of a heart. The adjustable intra-atrial shunt also includes a removable and/or removable/replaceable insert for placement within the retainer, the insert comprising a generally tubular body having a longitudinal opening to allow a flow of blood from an area of high pressure of the heart to an area of low pressure of the heart and a retrieval loop for removal of the insert from the retainer and the atrial septum, wherein the removable/replaceable insert and the opening allow a first rate of blood flow from an area of high pressure of the heart to an area of low pressure of the heart, and wherein the adjustable intra-atrial shunt is adapted to allow a second rate of blood flow from an area of high pressure of the heart to an area of low pressure of the heart by replacing the removable/replaceable insert with a second removable/replaceable insert having an opening of a different size.

In some embodiments, an adjustable, intra-atrial shunt includes a retainer having a plurality of struts and a plurality of apices joining the struts to form a generally cylindrical body having a left retaining flange and a right retaining flange, the tubular body adapted to fit within a wall of an atrial septum, the left retaining flange adapted to fit within a left atrium of a heart and the right retaining flange adapted to fit within a right atrium of a heart of a patient. This embodiment also includes a removable/replaceable insert for placement within the retainer, the insert comprising a plurality of flaps mounted on a generally cylindrical body having at least one opening to allow a flow of blood from an area of high pressure of the heart to an area of low pressure of the heart, wherein the removable/replaceable insert and the at least one opening allow a first rate of blood flow from an area of high pressure of the heart to an area of low pressure of the heart when first implanted into a patient, and wherein the removable/replaceable insert is adapted to allow a second rate of blood flow from an area of high pressure of the heart to an area of low pressure of the heart after portions of the insert absorb into the patient.

In some embodiments, an adjustable, intra-atrial shunt includes a retainer having a plurality of struts and a plurality of apices joining the struts to form a generally cylindrical body having a left retaining flange and a right retaining flange, the tubular body adapted to fit within a wall of an atrial septum, the left retaining flange adapted to fit within a left atrium of a heart and the right retaining flange adapted to fit within a right atrium of a heart of a patient. This embodiment also includes a removable/replaceable insert for placement with the retainer, the insert comprising at least one flap mounted on a body having at least one opening to allow a flow of blood from an area of high pressure of the heart to an area of low pressure of the heart, wherein the insert and the at least one opening allow a first rate of blood flow from an area of high pressure of the heart to an area of low pressure of the heart when first implanted into a patient, and wherein the insert is adapted to allow a second rate of blood flow from an area of high pressure of the heart to an area of low pressure of the heart after at least one portion of the insert absorbs into the patient.

In some embodiments, methods for treating diastolic heart failure are disclosed. The methods include implanting an inventive device into the atrial septum in order to decrease the left atrial and pulmonary venous pressure. The methods further include measuring the patient's hemodynamic status and heart failure indicators. Finally, the method includes adjusting the amount of blood flow through the inventive device in order to more effectively treat the heart disease. In some embodiments the methods for treating heart failure may include closing the inventive device, expanding the inventive device, collapsing the inventive device, or exchanging either the entire shunt or some components of the inventive device in order to increase the efficacy of the procedure.

The above summary of the invention is not meant to be exhaustive. Other variations and embodiments will become apparent from the description and/or accompanying figures disclosed herein and below. The embodiments described above employ elements of each other and are meant to be combined with each other. For example, embodiments of flow control element may be used with differing configurations of the body element, flange, or segment thereof. While certain combinations are disclosed, the invention is not so limited.

BRIEF DESCRIPTION OF THE DRAWINGS

The present invention will become more fully apparent from the following description and appended claims, taken in conjunction with the accompanying figures. Understanding that these figures merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying figures in which:

FIG. 4 is perspective view of the body assembly of the interatrial pressure vent by itself;

FIG. 5 is a right side view of the body assembly of FIG. 4;

FIG. 6 is a distal end view of the body assembly of FIG. 4;

FIG. 7 is an enlarged fragmentary cross-sectional view taken along line 7-7 of FIG. 6;

FIGS. 7A through 7C are a side elevational views of embodiments of the device in the stowed position;

DETAILED DESCRIPTION

Figure 1:
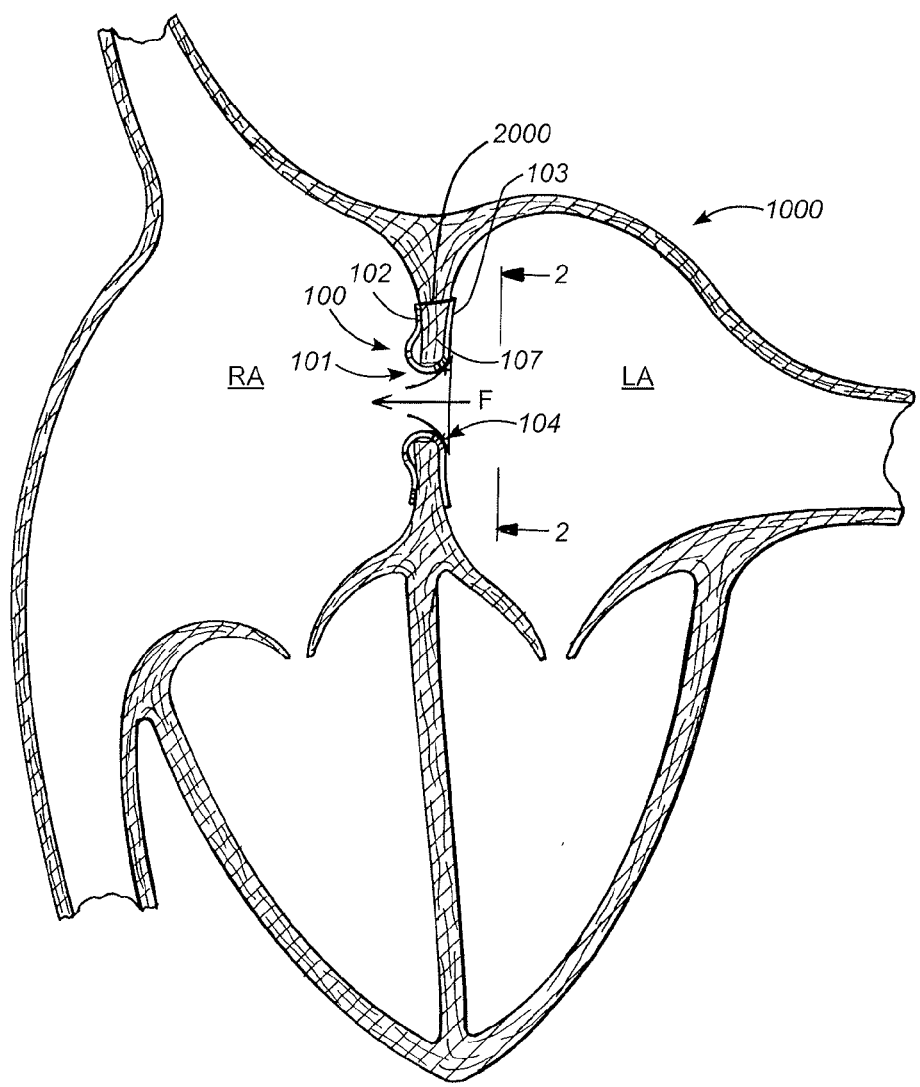
FIG. 1 is a schematic cross-sectional view of a patient's heart with an interatrial pressure vent of the present invention in situ.

Certain specific details are set forth in the following description and Figures to provide an understanding of various embodiments of the invention. Those of ordinary skill in the relevant art will understand that they can practice other embodiments of the invention without one or more of the details described below. Finally, while various processes are described with reference to steps and sequences in the following disclosure the steps and sequences of steps should not be taken as required to practice all embodiments of invention.

Unless otherwise defined, explicitly or implicitly by usage herein, all technical and scientific terms used herein have the same meaning as those which are commonly understood by one of ordinary skill in the art to which this present invention pertains. Methods and materials similar or equivalent to those described herein may be used in the practice or testing of the present invention. In case of conflict between a common meaning and a definition presented in this document, latter definition will control. The materials, methods, and examples presented herein are illustrative only and not intended to be limiting.

Certain specific details are set forth in the following description and Figs. to provide an understanding of various embodiments. Those of ordinary skill in the relevant art will understand that they can practice other embodiments without one or more of the details described below. Further, while various processes are described herein with reference to steps and sequences, the steps and sequences of steps are not be understood as being required to practice all embodiments of the present invention.

Unless expressly stated otherwise, the term "embodiment" as used herein refers to an embodiment of the present invention.

Unless a different point of reference is clear from the context in which they are used, the point of reference for the terms "proximal" and "distal" is to be understood as being the position of a practitioner who would be implanting, is implanting, or had implanted a device into a patient's atrial septum from the right atrium side of a patient's heart. An example of a context when a different point of reference is implied is when the description involves radial distances away from the longitudinal axis or center of a device, in which case the point of reference is the longitudinal axis or center so that "proximal" refers to locations which are nearer to the longitudinal axis or center and "distal" to locations which are more distant from the longitudinal axis or center.

As used herein, the terms "subject" and "patient" refer to any animal, such as a mammal like livestock, pets, and preferably a human. Specific examples of "subjects" and "patients" include, but are not limited to, individuals requiring medical assistance, and in particular, requiring treatment for symptoms of heart failure.

As used herein, the term "pressure differential" means the difference in pressure between two points or selected spaces; for example between one side of a flow control element and another side of the flow control element.

As used herein, the term "embolic particle" means any solid, semi-solid, or undissolved material, that can be carried by the blood and cause disruption to blood flow when impacted in small blood vessels, including thrombi.

As used herein, the terms "radially outward" and "radially away" means any direction which is not parallel with the central axis. For example, considering a cylinder, a radial outward member could be a piece of wire or a loop of wire that is attached or otherwise operatively coupled to the cylinder that is oriented at some angle greater than 0 relative to the center longitudinal axis of the cylinder.

As used herein, the term "axial thickness" means the thickness along an axis parallel to the center longitudinal axis of a shape or component.

As used herein, the term "axial direction" means direction parallel to the center longitudinal axis of a shape or component.

As used herein, a "sealable connection" is an area where components and/or objects meet wherein the connection defines provides for an insubstantial leakage of fluid or blood through the subject area.

As used herein, the term "lumen" means a canal, duct, generally tubular space or cavity in the body of a subject, including veins, arteries, blood vessels, capillaries, intestines, and the like.

As used herein, the term "sealably secured" or "sealably connected" means stably interfaced in a manner that is substantially resistant to movement and provides resistance to the flow of fluid through or around the interface.

As used herein, the term "whole multiple" means the product contains no decimal.

As used herein, the term "sealably secured" or "sealably connected" means stably interfaced in a manner that is substantially resistant to movement and provides resistance to the flow of fluid through or around the interface.

As used herein the terms "bio-resorbable" and "bio-absorbable" refer to the property of a material that allows it to be dissolved or absorbed in a living body.

As used herein, the term "hydraulic diameter" means the overall flow rate capacity of a conduit taking into consideration the number and configuration of the inlets and outlets of the conduit.

As used herein, the terms "gradual" and "gradually" mean that something occurs over the course of time, either in a stepwise fashion or a continuous fashion. For example, the hydraulic diameter of an inventive device may gradually change in a step-wise fashion from an initial value to a later different value when an absorbable suture that initially restrains a geometrical change in the device breaks during its absorption and is no longer able to restrain the geometrical change. As another example, the hydraulic diameter of an inventive device may gradually change in a continuous fashion when an absorbable diaphragm having an initial orifice is continuously absorbed over time so that the diameter of the orifice continuously increases in diameter.

It is to be understood that whenever relational numbers are used herein, e.g., "first," "second," etc., they are used for convenience of description and so they are to be interpreted with regard to the particular embodiment or claim in which they are presented, rather than as applying globally throughout this document to all embodiments or all claims. Thus, for example, in one embodiment it may be more convenient to use the term "first flange" to describe a flange that would be located in the right atrium when the device of that embodiment is implanted in an atrial septum, whereas it might be more convenient to use the term "first flange" in another embodiment to refer to refer to a flange that would be located in the left atrium when the implantable device of that embodiment is implanted.

It is to be understood that all flow rates are compared at identical the pressure differentials and fluid characteristics. Thus, whenever a device or a portion of a device is said to be adjustable from a first flow rate to a second flow rate, it is to be understood that the hemodynamic conditions under which those flow rates occur are identical to one another.

The present invention provides structures that enable several unique intracardiac and intraluminal valve devices and placement catheters therefor. In some embodiments directed toward the intra-cardiac setting, these valve devices are intended to allow sufficient flow from the left atrium to the right atrium to relieve elevated left atrial pressure and resulting patient symptoms but also prevent the amount of flow from the right atrium to the left atrium to minimize the potential for thrombi or other embolic material from entering the arterial circulation.

However, it should be appreciated that the invention is applicable for use in other parts of the anatomy or for other indications. For instance, a device such as that described in this disclosure could be placed between the coronary sinus and the left atrium for the same indication. Also, a pressure vent such as is described in this disclosure could be placed between the azygous vein and the pulmonary vein for the same indication.

It is also to be appreciated that although liners or internal sheaths to assist in directly fluid flow through the inventive device are described below with regard to only some of the embodiments, the other described embodiments may be adapted to include the use of liners or internal sheaths.

Referring now to FIG. 1, one embodiment of invention is shown where the invention is used as an interatrial pressure vent. FIG. 1 depicts the heart of a human subject. "LA" refers to the left atrium, and "RA" refers to the right atrium. The interatrial septum is depicted as 107. Interatrial pressure vent 100 includes a body element 101 and flow control element 104, embodiments of which will be described in further detail below. The body element 101 comprises flanges 102 and 103. In this and other embodiments described herein, flanges 102 and 103 may be annular flanges, which define a gap 2000 into which the septum 107 fits. In embodiments, after insertion, the interatrial pressure vent is securely situated in an opening created in the interatrial septum. Arrow F in FIG. 1 shows the direction of flow. It can be thus seen that a build up of pressure in the LA can be vented, by way of the inventive device, to the RA.

Figure 2:
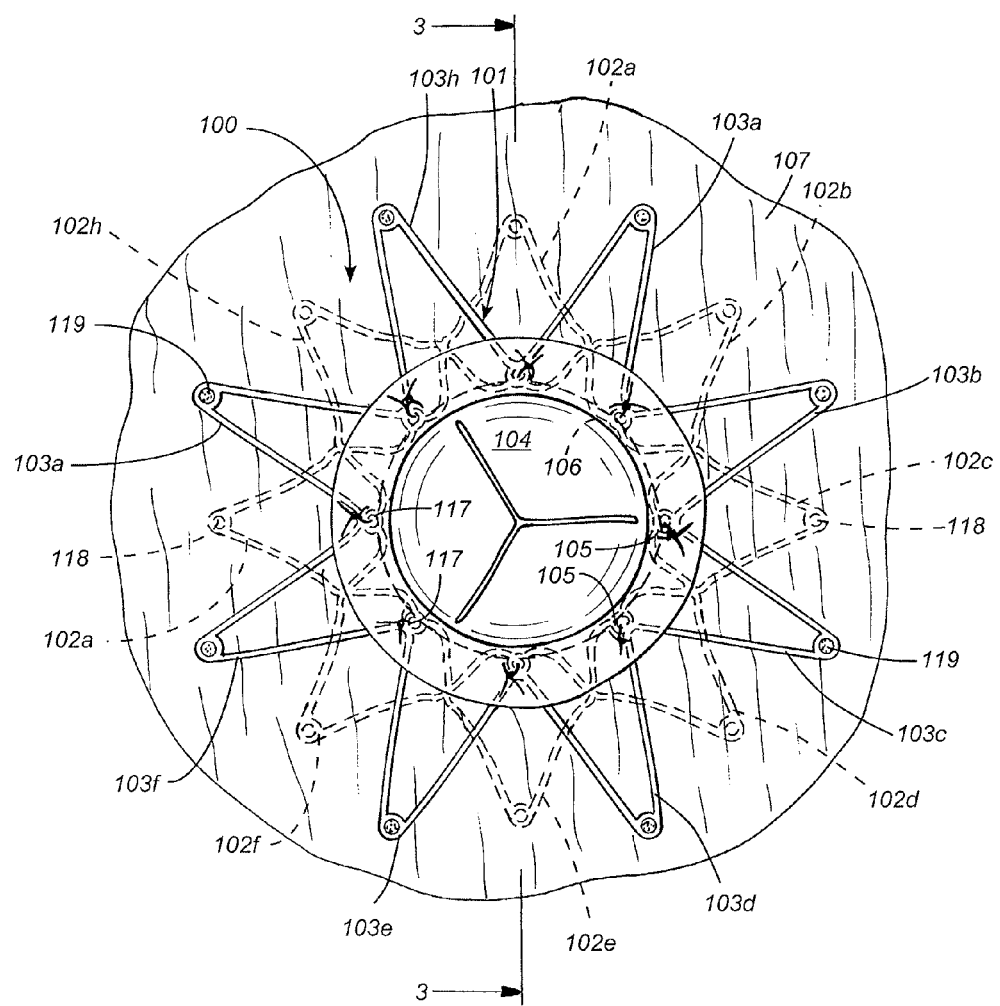
FIG. 2 is an end view of the interatrial pressure vent of FIG. 1 in situ as seen along line 2-2 of FIG. 1.

Referring now to FIG. 2, an embodiment of the interatrial pressure vent of the present invention is illustrated. Interatrial pressure vent 100 includes body element 101 comprising a substantially open mesh and including a substantially cylindrical core segment (shown end on) 106 and substantially annular flanges 102 and 103. Flanges 102 and 103 may be comprised of any number of flange segments (or "flange elements" or "flange members") 102*a*-102*h* and 103*a*-103*h*, that are attached adjacent to the end of the core segment and extend radially outward from longitudinal axis of the core segment and flow control element 104. "Flange segments" may also be referred to as "legs" herein. The flanges 102 and 103 (and thus the segments which comprise them 102*a*-*h* and 103*a*-*h*) in this and all embodiments disclosed herein, may also be integral with the core segment. That is, they need not be necessarily "attached" thereto but may be fabricated from the same material that defines the core segment (including in the manners described above and herein) and thus may be contiguous therewith. The flow control element may be attached to the body element, for example at locations 105. The flange segments in this and any embodiment of any annular flange may be formed of two individual strut elements or also can be formed of a single element. The flange segments may be generally rectangular in cross section, circular in cross section, oval in cross section or some other geometric shape.

Figure 2A:
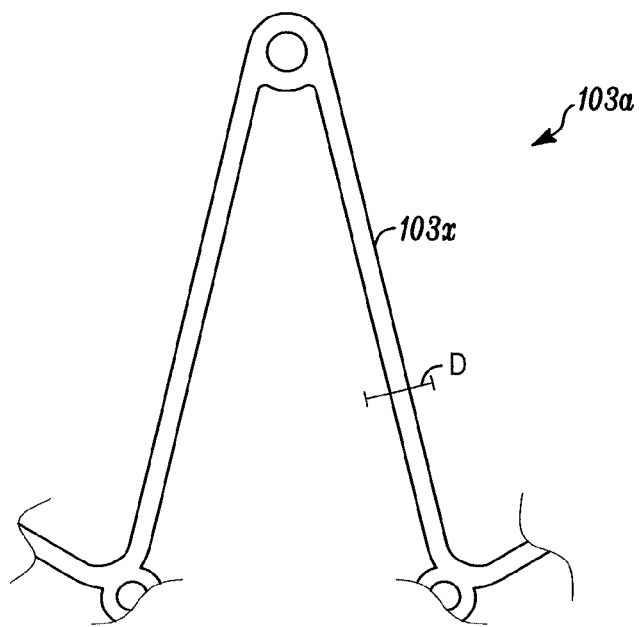
FIG. 2A is an end-on close up view of a flange segment of an embodiment of the present invention.
Figure 2B:
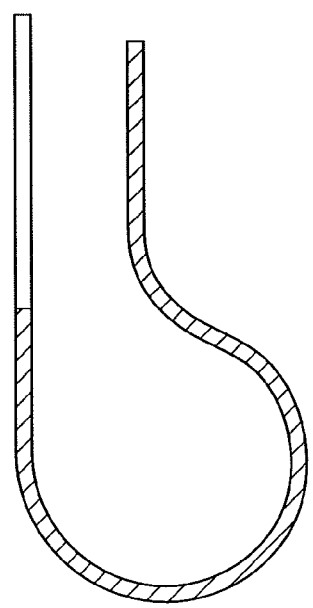
FIG. 2B is an enlarged side cross-sectional view of an embodiment of the invention to illustrate variations in flexibility in a flange.

In embodiments, the flange segments are designed to be more flexible than the core segment. In such embodiments, the increased flexibility may be achieved in several ways. In embodiments, a dimension of the surface of the strut elements that make up the flange segments is altered relative to the corresponding dimension of the struts (or elements, or members) that make up the core segments. FIG. 2A illustrate such embodiments. FIG. 2A shows an example flange segment 103a viewed end on. As shown, the end-facing dimension of strut element of 103x has a width D. By decreasing the width D in relation to the width of the outward-facing dimension of the struts that comprise the core segment, an increased flexibility of the flanges in relation to the core segment or other flange members (or portions thereof) can be achieved. FIG. 2B shows an enlarged fragmentary cross-sectional of an embodiment of the device substantially shown in FIG. 6. The view is taken along line 7-7 of FIG. 6. In this figure, the cross hatched area shows the area of increased flexibility. It can be seen that one area of the flange segment is thus more flexible than another area. In embodiments where the strut elements are circular, then in a similar fashion, the diameter of the strut element could be made to have a diameters less than the diameter of the strut (or similar elements) comprising the mesh-like configuration of the core segment. In embodiments where the flange element is made from a different section of material and is attached to the core segment, the segment material could be chosen to have a greater flexibility than the core segment (or remaining portion of the flange segment or flange itself as the case may be). The choice of materials based on their flexibility will be apparent to those skilled in the art. In the ways described above, the flange segments can achieve greater flexibility than the core segment (or the remaining portion of the flange segment or the flange itself as the case may be) thereby reducing probability of damage to the tissue of the septum while allowing the core segment to maintain a strong outward force against the septal opening and thus decrease the probability that the device could become dislodged.

In embodiments having an open-mesh configuration for the body element 101, the body element can be formed from a number of materials suitable for use in a patient, such as titanium, nitinol, stainless steel, Elgiloy, mp34n, Vitalium, Mobilium, Ticonium, Platinore, Stellite, tantalum, platinum, or other resilient material. Alternatively, in such embodiments, the body element 101 can be formed from a polymer such as PTFE, UHMPE, HDPE, polypropylene, polysulfone, or other biocompatible plastic. The surface finish of the body element may be smooth with no edges or sharp discontinuities. In other embodiments, the surface finish is textured to induce tissue response and tissue in growth for improved stabilization. In embodiments, the open mesh of body element 101 can be fabricated from a resorbable polymer such as polylactic acid, polyglycolic acid, polycaprolactone, a combination of two or more of these or a variety of other resorbable polymers that are well known to those skilled in the art.

In embodiments, the structure of the body element may be uniform and monolithic.

In other embodiments, the body element (mesh or monolithic) comprises porous materials to encourage tissue ingrowth or to act as a reservoir for containing one or more compounds that will be released over time after implant to address numerous issues associated with the product performance. These compounds can be used to diminish calcification, protein deposition, thrombus formation, or a combination of some or all of these conditions. The compound can also be used to stimulate an irritation response to induce tissue ingrowth. In embodiments, the compound can be an anti-inflammatory agent to discourage tissue proliferation adjacent to the device. Numerous agents are available for all of such uses and are familiar to those who are skilled in the art.

In embodiments, the material that comprises the body may be multilayered comprising a coating of resorbable polymer or semipermeable polymer that may comprise various compounds that may be released, and in some embodiments in a controlled manner over time, after implant to address numerous issues associated with product performance.

The mesh can be formed from wire that is pre-bent into the desired shape and then bonded together to connect the component elements either by welding them or adhesively bonding them. They could be welded using a resistance welding technique or an arc welding technique, preferably while in an inert gas environment and with cooling control to control the grain structure in and around the weld site. These joints can be conditioned after the welding procedure to reduce grain size using coining or upset forging to optimize fatigue performance.

In other embodiments, the mesh can be formed from a hollow tube that has been slotted using, for example, a machining laser or water drill or other method and then expanded to form the open structure. If a sufficiently elastic and resilient material, such as nitinol, is used, the structure can be preformed into the finished shape and then elastically deformed and stowed during delivery so the shape will be elastically recovered after deployment. The surface of the finished assembly must be carefully prepared to insure is passivated and free of surface imperfections that could be nidus for thrombus formation.

In embodiments, the flow control element 104 is a tissue valve such as a tricuspid valve, a bicuspid valve or a single flap valve formed from pericardial tissue from a bovine, porcine, ovine or other animal. Any number of cusps may be used. The flow control element is formed using a number of processing steps and auxiliary materials such as are well known in the art.

The flow control element 104 can also be a ball valve, a duckbill valve, a leaflet valve, a flap valve, a disc in cage type valve, a ball in cage type valve or other type of valve formed from a polymer or polymers or a combination of polymers, ceramics and metals such as dacron, teflon, polyurethane, PET or other suitable polymer; titanium, stainless steel, nitinol, MP35N, elgiloy, or other suitable metal; zirconia, silicone nitride, or other suitable ceramic. Valves or portions thereof may comprise different stiffness/flexibly properties with respect to other valves or portions thereof in the flow control element.

The flow control element 104 preferably extends to a point along the flange assembly 103 to enable creation of a sealable connection to the septum wall after placement. This is more particularly shown in FIG. 3 where it can be seen that in embodiments, the flow control element extends beyond the length of the core segment and is folded and attached to the core segment so as to create a lip that extends in a direction center of the opening in the vent. When the device is abutted against the septal wall, this lip forms said sealable connection and thus can reduce the likelihood that blood can flow through the septal opening via pathways between the outer surface (septal-facing surface) of the interatrial pressure venting device and the septal opening. The flow control element 104 is attached to the body element 101. This can be accomplished by using a suture material, such as silk, nylon, polypropylene, polyester, polybutylester or other materials such as are well known to those skilled in the art. In embodiments, flow control element 104 can be attached to body element 101 using adhesive bonding agents such as cyanoacrylate, polymethylmethacrylate, or other materials such as are well known to those skilled in the art. In other embodiments, flow control element 104 can be attached to body element 101 via staples, rivets, rings, clamps or other similar methods as are well known to those skilled in the art.

As mentioned above, flow control element can be made of material selected for its flexibility/stiffness. In embodiments where a loose valve is desired that resonates more closely with the cycle of the heart, a however stiffness material may be chosen. In embodiments where it is desired to open the valve when the pressure differential reaches a selected value, the material of the flow control element can be selected and/or processed in a manner to open at the desired differential. The leaflets or sections of the flow control element itself may also comprise areas of variable stiffness, and or may be more flexible or less flexible than other leaflets or components of the flow control element.

Figure 3:
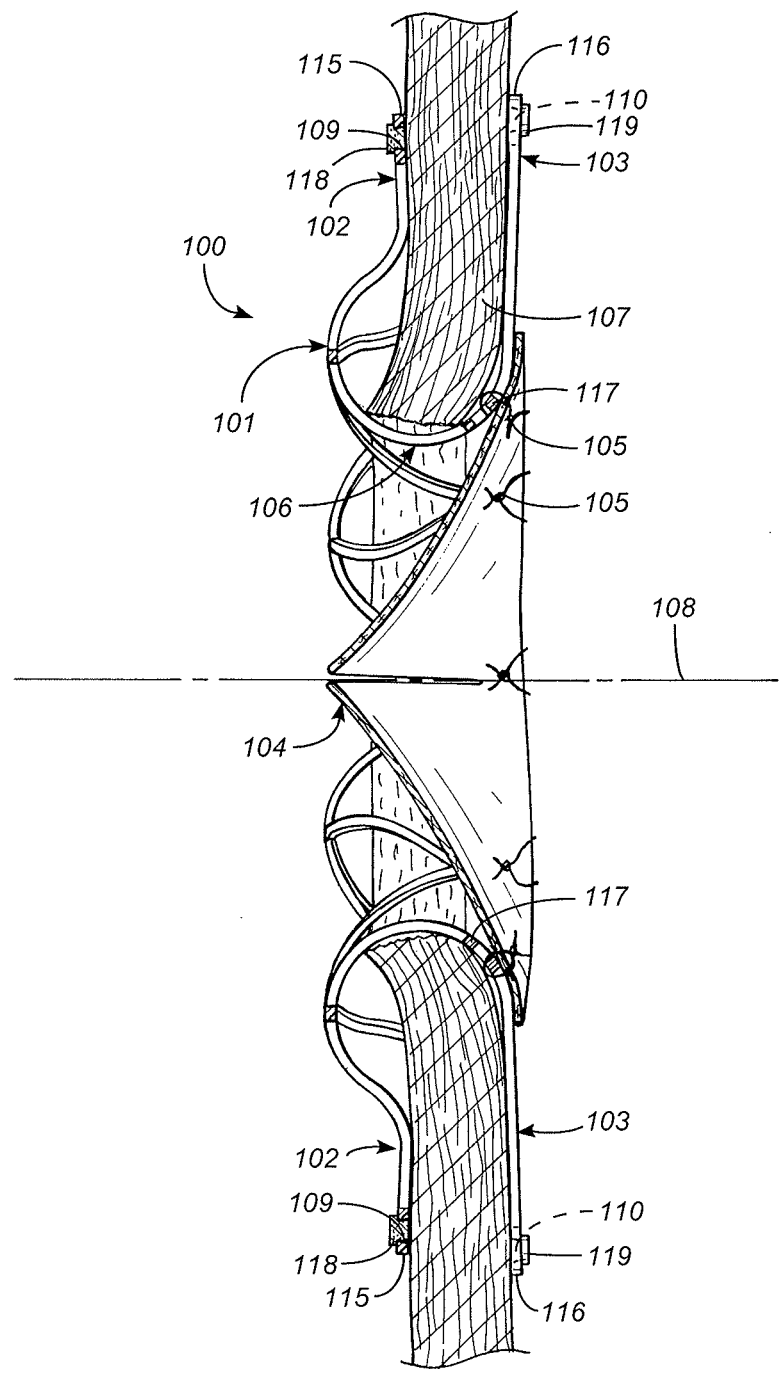
FIG. 3 is a cross-sectional side view taken along line 3-3 of FIG. 2.

FIG. 3 shows the device implanted in the atrial septum of the heart of a patient. As can be seen from the figure, the core segment 106 can be formed contiguously with flanges 102 and 103 and thus flange segments 102a-102h and 103a-103h respectively. In the embodiment shown, flow control element 104 is contained within the core segment 106 so it does not extend beyond the face of the body element 101, thereby insulating it from contact from other body structures or peripheral tissue. In embodiments, the core segment 106 can be extended to protrude beyond the interatrial septum 107 and the flange assembly 102 and/or 103 on at least one side of the interatrial septum 107 and can be formed with a shape that extends to create a lip in the manner described above. In embodiments, the ends of the flange assemblies 102, 103 are formed to lie at a parallel angle to and against the septal wall along at least a part of its length to increase the area of contact and thereby decrease the stress concentration against the septal wall.

Referring now to FIG. 4, an embodiment of the body element of the present invention is shown. This perspective view of the body element 101 shows how, in embodiments, the ends of flange segments 102a-102h, 103a-103h are rounded at their distal ends 115 and 116 to reduce stress concentrations against the interatrial septum after placement. This rounded shape can easily be formed as part of the integral shape of the flange segment. In other embodiments, the thickness of the segment in this area may be decreased to decrease the stress further against the interatrial septum, which is similar to embodiments described above. Also similar to embodiments described above, if the segment is round, the diameter can be decreased in order to increase flexibility. Also, as described above a different material of higher flexibility could be used for the end portions of the segments.

Figure 7B:
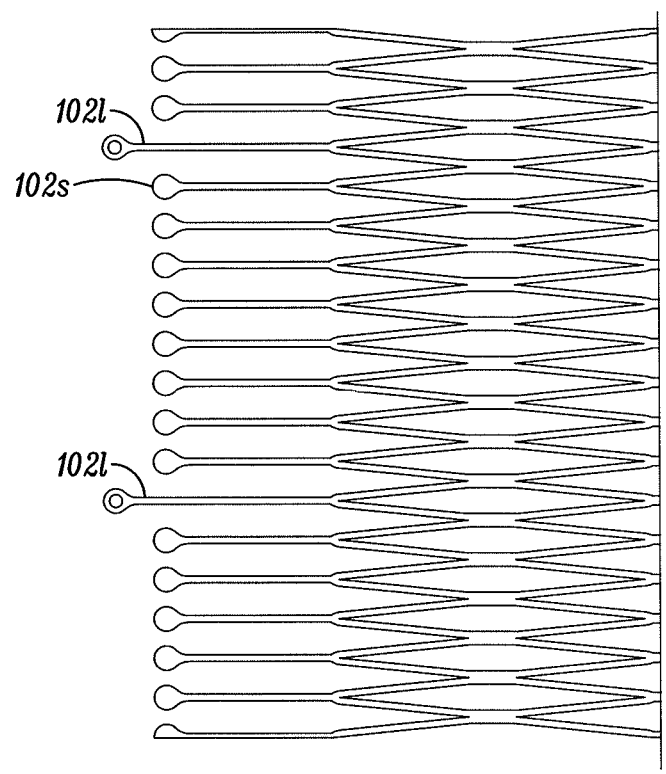
Figure 7C:
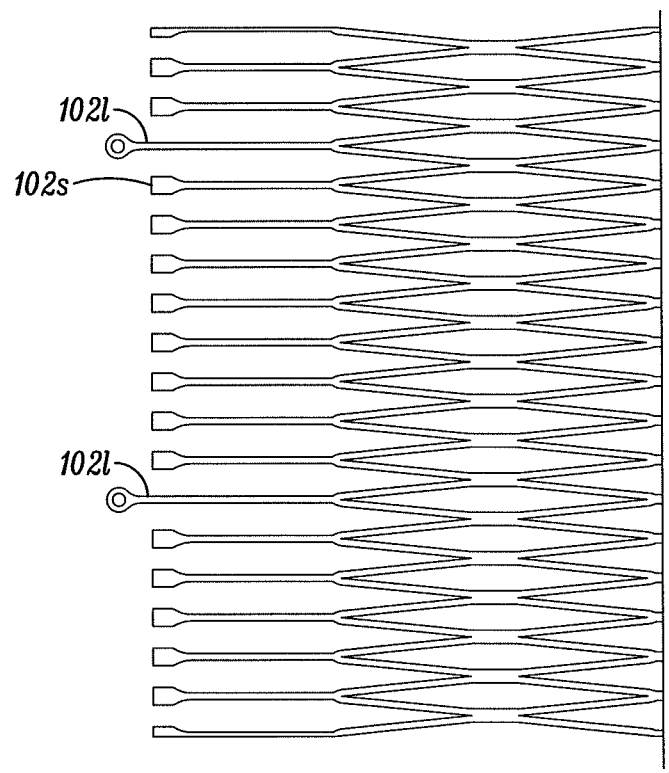

While rounded shapes at the ends of the flange segments reduce stress on the septum, other variations on this theme are contemplated. FIGS. 7A through 7C illustrate embodiments where the shape of the end portions of the flange segments has configurations to achieve less stress against the septal wall—among other goals. FIG. 7A is a side elevational view of embodiment of the pressure venting device in its stowed configuration. Core segment 106 of body element 101 is shown and, in this embodiment, is integral with flanges 103 and 102. The individual flange segments are not labeled; however, it is easily seen that flange 103 comprises segments substantial similar to those described above. There is no eyelet or opening at the end of the segment in the embodiment shown. Flange 102 shows an embodiment where the flange segment is not comprised of a triangular or multi-strut arrangement as described above but rather a single-member segment. Any flange of the present invention may be constructed with single-member segment. An example single member is referred to as 103s. In this example, at the end of each single-member flange segment (102s) for example, there is an eyelet. FIG. 7B shows an embodiment similar to that shown in FIG. 7A where the end of the segments 102s are not eyelets but rather pads. FIG. 7C shows another embodiment where the ends of the segments 102 are paddle shaped. Other smooth-edged shapes could be used, and it should be understood that such shapes and configurations apply to all manner of flange segment ends, not only single-member segments. This would include the ends of flange segments shown and described herein, for example with reference to FIGS. 2 through 7.

FIGS. 7A-C also show embodiments having at least one flange segment being longer than the other flange segments. Again, while represented as single-member flange segments they need not be and as such a configuration with at least one longer segment may apply to any flange-segment configuration disclosed herein. The benefits and purpose of having at least one longer flange segment will be described more fully below.

In embodiments, the outer ends of the flange segments 102a-102h, 103a-103h are formed with integral marker holes or slots 109 and 110 (shown in FIGS. 3 and 7 for example) in which markers 118 and 119 can be positioned so the device may more easily be visualized using radiographic imaging equipment such as with x-ray, magnetic resonance, ultrasound or other imaging techniques. Markers as disclosed herein may be applied to the ends of any segments, not just those with holes or eyelets therein. A radiopaque marker 118 and 119 can be swaged, riveted, or otherwise placed and secured in the hole and thereby dimensioned to be flush with the end of the segment. Markers may also be simply attached or to end of a segment not having a hole. In all embodiments having markers, flange ends 115 and 116 are more visible when imaged. In other embodiments, the markers 118 and 119 can be bonded with an adhesive agent such as cyanoacrylate or epoxy or a variety of other materials that are available and suitable for implant as are well known. The markers may be proud (as shown for example in FIG. 7) or flush with the end of the flange segment. The radiopaque marker 118 and 119 may be formed of tantalum, tungsten, platinum irridium, gold, alloys of these materials or other materials that are known to those skilled in the art. Also markers 118 and 119 comprising cobalt, fluorine or numerous other paramagnetic materials or other MR visible materials that are known to those skilled in the arts can be incorporated together with the radiopaque materials, or in alternating locations of the flange segments to enable both x-ray and MR imaging of the interatrial pressure vent. Alternatively, the ends of the flange elements 102a-102h and 103a-103h can be wrapped with a foil made of the same marker materials. In embodiments, the radiopaque material can be laminated to the flange segments and bonded through a welding process or using an adhesive such as cyanoacrylate or numerous other adhesives known to those skilled in the art.

Suture rings 117 can be formed in the body element to locate and fix the attachment site along the body element to the flow control element. The suture rings can be circular holes formed into the structure or they could also be some other shape such as rectangular or triangular and also can be formed as a secondary step, for example by standard machining techniques, using a secondary laser machining step, or with electro-chemical etching. Preferably the connection between a segment and any other segment of the body element are formed with as large a radius as possible to increase resistance to fatigue failure. Also, preferably, all edges of the formed device are rounded to improve biocompatibility and hemocompatibility.

The pattern of suture rings as well as which of the rings are selected during suturing may affect the properties of the flow control element. For example, in embodiments where it is desired to have the flow element loose and flappable, less suture rings may be utilized and, in such embodiments, RA-side end of the flow control element may contain relatively less sutures than the LA side. In other embodiments, it may be desirable to keep the flow control element affixed to the core segment for an increased length of the segment thereby reducing the amount of flow control element material that affecting flow. Still in other embodiments the top or bottom portion the flow element at the RA side may be sutured in such a way so as to allow the top or bottom portion of the flow control element to affect flow more than the other portion respectively. Embodiments discussed below where the flow is "aimed" may utilize suturing patterns effective to enable the desired flow control element configuration.

Returning to the flange segments, in an embodiment, the interatrial pressure vent 100 is comprised of an equal number of flange segments on each side of the interatrial septum. In embodiments, there are eight flange segments on each side of the core segment. In another aspect there are an equal number of suture rings and flange segments on one side of the interatrial pressure vent. In other embodiments, there are seven flange segments on each side of the core segment. In other embodiments, there are six flange segments on each side of the core segment. In other embodiments, there are five flange segments on each side of the core segment. In other embodiments there are four flange segments on each side of the core segment. In other embodiments there are three flanges on each side of the core segment. In other embodiments there are two flanges on each side of the core segment. In other embodiments, there is one flange on each side of the core segment. Still in other embodiments there are more flange segments as compared to flange segments. And in other embodiments, there are more flange segments as compared to flange segments. As can be seen there are a number of variations for the number of flange segments and the skilled artisan will appreciate that any number could be used while not deviating from the scope and spirit of the invention.

Referring now to FIG. 5, the body element of an embodiment of the present invention is displayed in side view. The flange segments can be formed to produce a gap G (also referred to as an annular gap) between the ends of flange segments on one side of the body and flange segments on the other side of the body, when the device is in its "native" or un-deployed state. When the device is deployed, it flexes to accommodate the tissue and as such the gap may expand when tissue is positioned therein. In embodiments, this gap is slightly smaller than the thickness of the interatrial septum. In other embodiments, the gap can be larger than the thickness of the interatrial septum. In other embodiments the gap can be zero. In another aspect the gap can be negative: in this case the flange segments on each side of the body can be formed to cross each other in order to exert more pressure between the deployed flange segments and the interatrial septum. Also shown in FIG. 5 are radiopaque markers 118 and 119, which in embodiments are shown to be located adjacent to the end of the flange segments.

Referring now to the embodiment shown in FIG. 6, the flange segments 102a-102h are oriented so they are not directly opposed to flange segments 103a-103h on the opposite side of the body element so that after placement there is no pinching points thereby reducing the chance for tissue injury. In embodiments, flange segments 102a-102h are arranged midway between adjacent ends of flange segments 103a-103h. In embodiments the length of flange segments 102a-102h are similar to the length of flange segments 103a-103h. However in other embodiments the length of flange segments 102a-102h are identical to the length of flange segments 103a-103h; the length of flange segments 102a-102h are longer than 103a-103h; and the length of flange segments 102a-102h are shorter than flange segments 103a-103h.

Referring now to FIG. 7, in embodiments having radiopaque markers it can be seen that the radiopaque markers 118 and 119 may be placed into the marker holes 109 and 110 (or placed on the ends of flange segments that do not have holes) to locate the ends of the flange segments 102a-102h and 103a-103h with a non-invasive imaging technique such as with x-ray or MRI during or after the procedure. In embodiments, the markers 118 and 119 can be formed to be flush in an axial direction with the outer surface and the inner surface of the flange segments 102a-102h and 103a-103h. In another aspect, the markers 118 and 119 can be formed to extend in an axial direction beyond the outer surface of the flange segments 102a-102h and 103a-103h, away from the interatrial septum. In embodiments, the markers 118 and 119 can be formed to extend in an axial direction beyond the inside of the flange segments 102a-102h and 103a-103h, toward the interatrial septum. In embodiments, the markers 118 and 119 can be formed to extend in an axial direction beyond the inside and the outside of the flange segments 102a-102h and 103a-103h. In embodiments, the markers 118 and 119 can be formed to be recessed in an axial direction within the surface of the inside of the flange segments 102a-102h and 103a-103h. In embodiments, the markers 118 and 119 can be formed to be recessed in an axial direction within the outside of the flange segments 102a-102h and 103a-103h. In embodiments, the markers 118 and 119 can be formed to be recessed in an axial direction within both the inside and the outside of the flange segments 102a-102h and 103a-103h. In embodiments, the markers 118 and 119 can be formed to extend in a radial direction within the width of the flange segments 102a-102h and 103a-103h. In embodiments, the markers 118 and 119 can be formed to extend in a radial direction flush with the width of the flange segments 102a-102h and 103a-103h.

Figure 8:
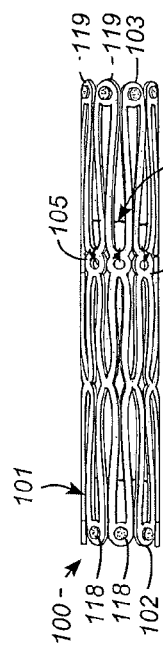
FIG. 8 is a side elevational view of the interatrial pressure vent of FIG. 1 in a collapsed configuration prior to loading in a placement catheter.

Referring now to FIG. 8, an interatrial pressure vent 100 of the present invention is shown in its stowed configuration. In embodiments, the interatrial pressure vent can be collapsed to a substantially cylindrical shape for stowing in a delivery catheter during placement. Flange segments 102*a*-102*h* and 103*a*-103*h* can be fabricated to be substantially equal in length. The "stowed position" is not meant to apply only to devices having flange segments of equal length but rather to all embodiments of the venting device disclosed herein. Devices having flange segments of varying length and orientation such as those described herein are also designed to stow in substantially the same manner as shown in FIG. 8. In an embodiment 200 seen in FIG. 20, flange segments 202*a*-202*h* and 203*a*-203*h* are formed on a slanted angle so that, when marker elements are secured to the ends of the flange segments, the flange segments can be stowed into a smaller volume. In embodiments 300 seen in FIG. 21, flange segments 302*a*-302*h* are formed of alternating length to allow stowage into a smaller volume.

Figure 9:
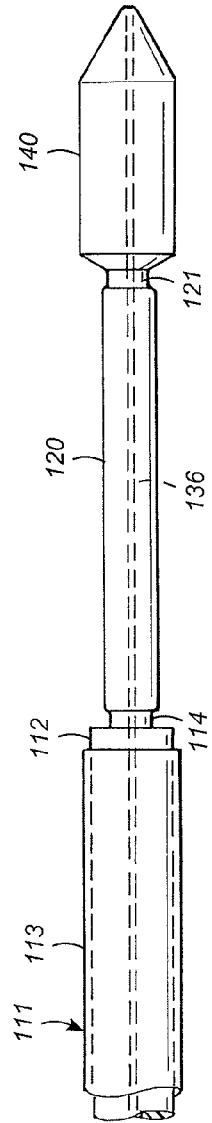
FIG. 9 is a side view of the distal end of a placement catheter in its open position.

Referring now to FIG. 9, an embodiment of the distal end of the placement catheter 111 of the present invention is shown in its open position. The inner shaft 112 is fabricated with a center lumen 136 of sufficient diameter to contain a guidewire 138 or also for use in injecting contrast or other liquid. Commonly, the lumen would be sized for a guidewire of 0.010", 0.011", 0.014", 0.018", 0.021", 0.028", 0.035", 0.038", 0.042" or 0.045". This lumen 136 can also be used to measure pressure at the distal end of the catheter using other equipment and techniques that are well known to those skilled in the art. The lumen 136 preferably extends through the entire length of the inner shaft 112. Alternatively, the guidewire lumen 136 can extend for a shorter length in the proximal direction and then through a side hole (not shown) of the inner sheath. A corresponding side hole (not shown) is placed on the outer shaft 113 adjacent to the side hole in the inner shaft 112 to create a pathway between the center lumen 136 of the inner shaft 112 and the outside of the outer shaft 113. In this way it is possible to pass a guidewire from this distal end of the inner lumen 136 through the side hole and exchange the catheter over a guidewire that is less than twice the length of the catheter 111 while securing the guidewire position during exchange.

In embodiments, the inner shaft 112 is configured with a waist section 120 to contain the folded interatrial pressure vent 100 between the gap formed in the space outside of this section of inner shaft 112 and the inside of the outer shaft 113. The inner shaft 112 is may be formed to contain at least one circumferential groove 114 at the proximal end of waist section 120 that forms a recess between the inside of the outer shaft 113 and the smallest diameter of the groove that is greater than the gap formed in the space between the waist section 120 and the inside of the outer shaft 113. Radiopaque markers 118 can extend in a radial direction past the outer surface of the flange segments 102*a*-102*h* and in embodiments, when interatrial pressure vents of the present invention are is folded into their stowed configuration and placed into position over inner shaft 112, radiopaque markers 118 are dimensioned to fit into groove 114. Other similarly dimensioned sections may be used; that is, that which fits into the groove need not necessarily be a radiopaque marker. In embodiments, when interatrial pressure vents of the present invention are stowed in this manner, the gap between waist section 120 and the inside of outer shaft 113 is not sufficient to allow radiopaque markers 118 beyond the distal end of groove 114 unless the outer sheath 113 is retracted beyond the proximal end of groove 114.

The inner shaft 112 may be formed with a groove 121 on the distal end of the waist section 120 adjacent to the location of the distal end of the interatrial pressure vents of the present invention are radiopaque markers 119 (or similar dimensioned members) can extend in a radial direction past the outer surface of the flange segments 102*a*-102*h* and in embodiments, when interatrial pressure vents of the present invention are folded into its stowed configuration and placed into position over inner shaft 112, radiopaque markers 119 are dimensioned to fit into groove 121. In another aspect, the inner shaft 112 may be formed with a circumferential groove 114 on the proximal end of waist section 120 and a circumferential groove 121 on the distal end of the waist section 120 The inner shaft can be formed of a variety of polymers or metals or combinations of polymers and metals that are suitable for use in a patient. The inner shaft can be fabricated from a single length of PTFE, UHMWPE, FEP, HDPE, LDPE, polypropylene, acetal, Delrin, nylon, Pebax, other thermoplastic rubber, aliphatic or aromatic polyurethane, or a variety of other engineering resins that are well known to those skilled in the art. In embodiments, the inner shaft can be fabricated using multiple layers of two or three of the above-mentioned polymers to combine desirable properties of each. For example, the outer surface could be composed of polyurethane to enable easier bonding of auxiliary components to the inner shaft. The inner layer could be PTFE to convey better lubricity to the inner shaft. In embodiments, the inner shaft and or the outer shaft could be coated on the inner and or outer surface with a coating material that conveys specific properties to the shaft like antithrombogenicity or lubricity. There are numerous available coating materials suitable for these purposes as are well known to those skilled in the art. The inner shaft can be compounded with a radiopacifier to increase the visibility of the inner shaft under fluoroscopy using bismuth salts such as bismuth subcarbonate, bismuth oxychloride, bismuth trioxide, tungsten powder, molybdenum powder or other radiopacifier such as are well known to those skilled in the arts. Similarly, the outer sheath can be fabricated from the same set of materials as the inner sheath, in the same manner and using the same coatings. Embodiments described below in connection with a flange rather than circumferential groove operate in substantially the same manner as described above and herein, except the device does not necessarily have projections that fit into and are retained by the grooves.

Figure 10:
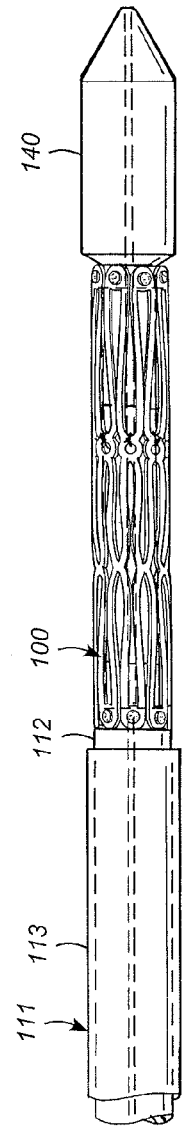
FIG. 10 is a side view of the distal end of a placement catheter in its open position and with an interatrial pressure vent in its stowed configuration and in position over the inner shaft of the catheter.
Figure 17:
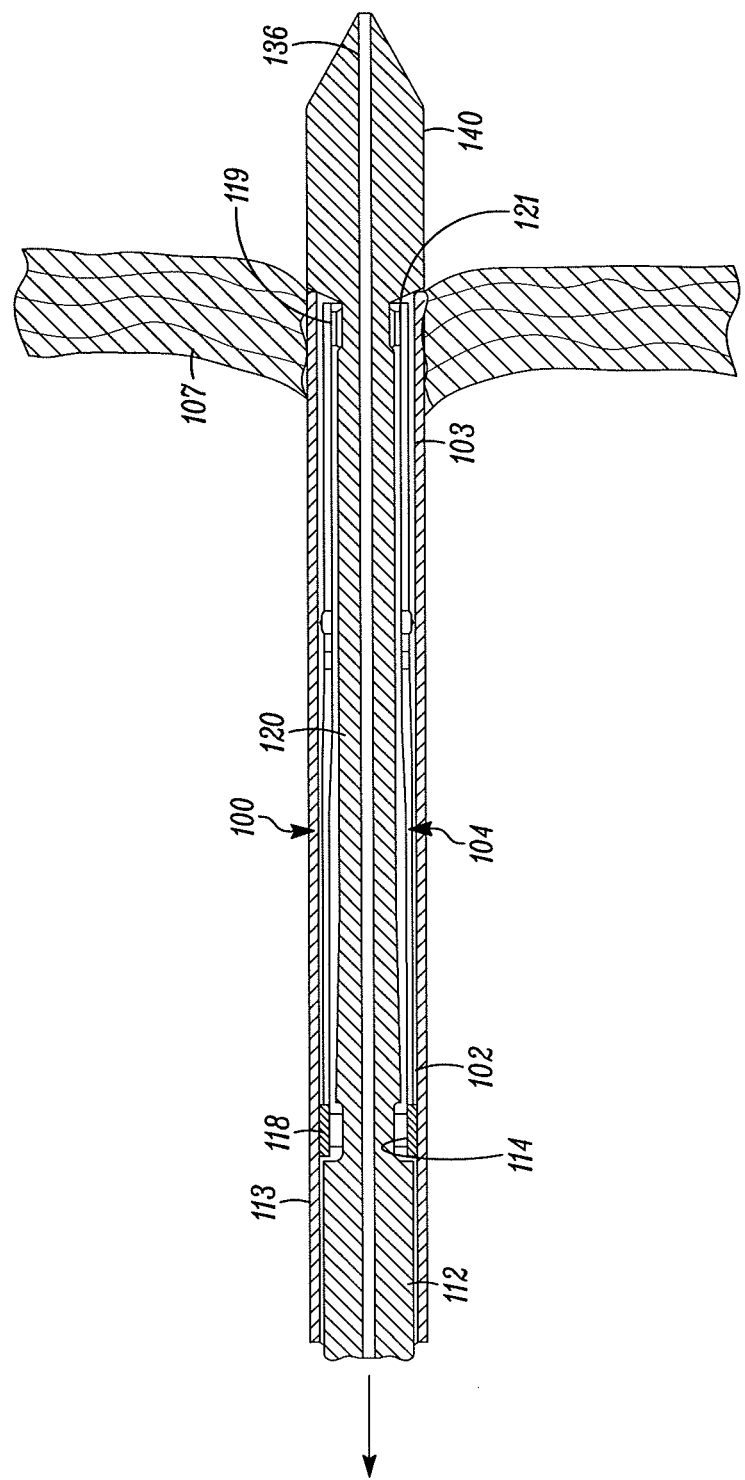
FIG. 17 is an enlarged cross-sectional detail view of the distal end of the placement catheter of FIG. 16 but showing the distal flange segments of the interatrial pressure vent being retracted from the interatrial septum as if it were determined to be in an undesirable position by imaging the radiopaque markers and going to be redeployed.

Referring now to FIG. 10, a folded representative interatrial pressure vent 100 of the present invention is shown in its stowed position with the placement catheter 111 of the present invention shown in its open position. In practice, if the body of the interatrial pressure vent is fabricated of nitinol or other elastic material, when the placement catheter is in its fully open position, the flange segments 102*a*-102*h* and 103*a*-103*h* would automatically recover into a shape like that shown in, for example, FIG. 4, hence this Figure is shown to illustrate the position of the interatrial pressure vent 100 relative to the waist section 120 and grooves 114 and 121. When radiopaque markers (or similarly dimensioned members) 118 extend beyond the thickness of the inside of body segment 101 of interatrial pressure vent 100, they form a projection within interatrial pressure vent 100 that can be captured within groove 114 to secure the position of the interatrial pressure vent 100 during placement. During deployment, the outer shaft 113 of placement catheter 111 is retracted a sufficient distance to reveal the distal portion of the interatrial pressure vent 100 allowing the flange segments 103*a*-103*h* to dilate radially away from the central longitudinal axis of body 101. By capturing the radiopaque 118 markers within the groove 114, the device can be repositioned easily without further deployment, or the device can be completely retracted and removed from the patient without deployment as indicated in FIG. 17.

Figure 11:
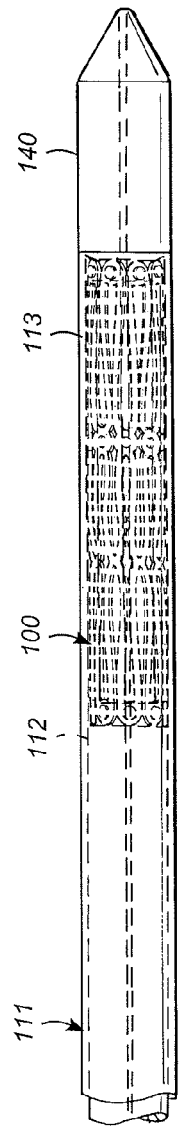
FIG. 11 is a side view of the distal end of a placement catheter in a closed configuration with an interatrial pressure vent in its stowed configuration loaded onto the placement catheter.

Referring now to FIG. 11, an interatrial pressure vent 100 of the present invention is shown completely stowed within the placement catheter 111 of the present invention.

Figure 11A:
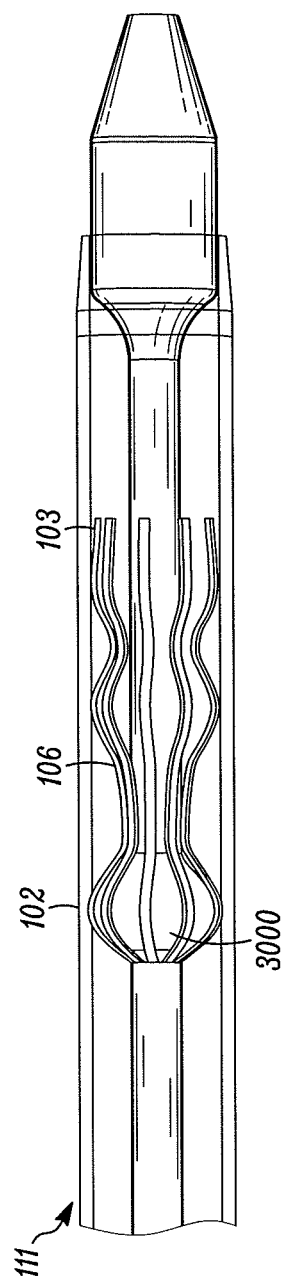
FIG. 11A is a side view of another embodiment of a placement catheter with an interatrial pressure vent stowed therein.

FIG. 11A shows an embodiment of the placement catheter similar in operation to those described herein but operative to engage an interatrial pressure vent by way of a slightly different mechanism than described above in connection with circumferential grooves. This figure shows a schematic depiction of a stowed interatrial vent. Rather than having the grooves as described above, this embodiment of a placement catheter comprises an inner shaft having a flange or member 3000 (rather than a groove) which has a diameter larger than that of the inner shaft to grip and hold an end of the interatrial vent device as shown. As shown in the figure, the flange and its segments (collectively referred to in the figure as 102) wrap around the ball-shaped flange 3000 and allow the interatrial pressure vent to be moved with the placement device in the manners described herein.

Figure 12:
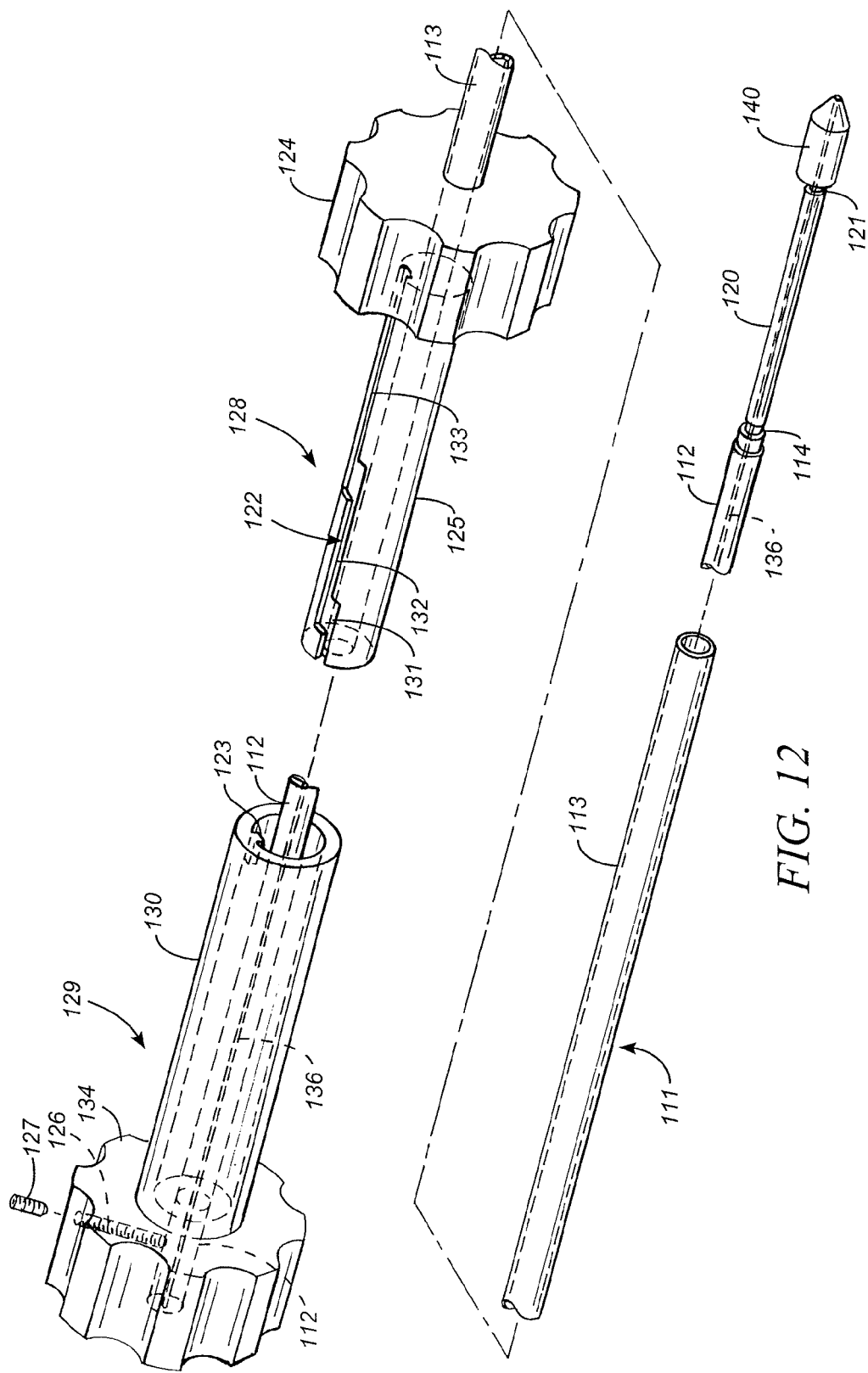
FIG. 12 is an exploded perspective view of the proximal and distal ends of a placement catheter.

Referring now to FIG. 12, a placement catheter 111 of the current invention is shown. It should be noted that while the inner shaft is depicted as having grooves in FIG. 12, the inner shaft may comprise the flange 3000 as described above in connection with FIG. 11A. The skilled artisan will appreciate that the operation of the device is substantially similar whether grooves or flanges are utilized. The placement catheter 111 comprises a first handle component 128 that can be attached to outer shaft 113. The first handle component can be attached to the outer shaft 113 using a variety of adhesive methods such as solvent bonding using a solvent for both the handle and outer shaft material; an organosol consisting of a solvent and polymer in solution that is compatible with both the outer shaft and the first handle component; a polymerizable adhesive, such as polyurethane, cyanocrylate, epoxy or a variety of other adhesives as are well known to those skilled in the art. The first handle component can be fabricated from a variety of metals such as aluminum, stainless steel, titanium or a number of other metals and alloys as are well known to those skilled in the art. In embodiments, the first handle component 128 is fabricated from a polymer such as polycarbonate, or a variety of engineering resins, such as Lexan, or others as are well known to those skilled in the art. The first handle component comprises hand grip section 124 and tubular shaft section 125. The tubular shaft section 125 can contain keyway 122 that is formed or machined into the shaft section. The keyway is preferably formed with three linear sections; a first linear section 131, a second linear section 132 and a third linear section 133. Each of these sections is formed to traverse along a path primarily parallel with the center axis along the length of the first handle component but each is displaced radially from one another by at least about half of the width of the keyway. The placement catheter 111 also can comprise a second handle component 129 that can be attached to inner sheath 112. The second handle component can be fabricated from the same variety of metals and polymers as the first handle component. The two handles can be fabricated from the same materials or from different materials. The second handle component can be attached to the inner sheath in the same manner and using the same materials as the first handle component attaches to the outer sheath. In embodiments, the second handle component can contain threaded hole 126 for containing set screw 127. The set screw can be twisted to capture the inner shaft against the second handle component. The second handle component 129 also can comprise a second hand grip section 134 and second tubular shaft section 130. The second tubular shaft section can contain key 123 that is formed or machined of suitable dimension to adapt to keyway 122 of first handle component 128. When assembled, second handle component 129 can be slideably moved relative to first handle component 128 in a manner controlled by the shape and length of the key way 122. As the second handle 129 is advanced relative to the first handle 128, it can be appreciated that he inner sheath 112 will slide in a distal direction out from the outer sheath 113. It can be appreciated that when the second handle component 129 is assembled, the key 123 is slid into the first linear section 131 and advanced until it hits the edge of the keyway formed between the first linear section 131 and the second linear section 132. In order for the second handle component 129 to advance further, it must be rotated and, once rotated, it can be advanced further but will stop when the key 123 hits the edge of the keyway formed between the second linear section 132 and the third linear section 133. The keyway dimensions are preferably selected with consideration for the combination of lengths of other components in the placement device. A first position, defined as the position when the key 123 is in contact with the proximal edge formed between the first linear section 131 and the second linear section 132, is preferably determined so, when fully assembled and with the interatrial vent in its stowed position within the placement catheter, the outer shaft 113 will completely cover the length of the interatrial pressure vent 100 as is desired during catheter placement. The keyway dimensions can also be selected to result in a second position, defined as the position when the key 123 is in contact with the distal edge formed between the second linear section 132 and third linear section 133. The second position would preferably be selected to reveal the full length of flange segments 103a-103h but retain flange segments 102a-102h within the outer shaft 113 of the catheter. The length of the third linear section 133 would preferably be selected so that, when the second handle component 129 was advanced completely against the first handle component 128, the full length of the interatrial vent 100 would be uncovered by the outer shaft 113 and the device would be deployed. A variety of other configurations of the first and second handle components could be used for this same purpose. The first handle component tubular shaft section 125 and the second handle component tubular shaft section 130 could be threaded (not shown) so the first handle component 128 could be screwed into the second handle component 129. Alternatively, gear teeth (not shown) could be formed in the first tubular shaft section 125 of the first handle component 128 and a gear wheel (not shown) could be incorporated into the second shaft tubular section 130 of the second handle component 129. The gear wheel would preferably be chosen to mesh with the gear teeth and the second handle component 129 could be advanced toward the first handle component 128 by rotating the gear wheel. A variety of other design configurations could be utilized to control the relative location between the first handle component and the second handle component as are well known to those skilled in the art.

FIGS. 13 through 17 show embodiments of a system for treating heart failure of the present invention. More specifically FIGS. 12 through 19 show how the placement catheter is introduced and positioned in a patient and methods for placing the interatrial valve in a patient. The interatrial pressure vent 100 is presterilized and packaged separately from the placement catheter 111. Sterilization can be performed by exposing the device to a sterilizing gas, such as ethylene oxide, by exposing the device to elevated temperature for an adequate period of time, by using ionizing radiation, such as gamma rays or electron beam or by immersing the device in a fluid that chemically crosslinks organic molecules, such as formaldehyde or gluteraldehyde and then rinsed in sterile water or sterile saline. For each of these sterilization methods, consideration must be given to compatibility of the materials so device performance is not adversely affected as a result of the sterilization process. Also, the packaging design and materials must be carefully considered with the sterilization procedure, post sterilization handling and storage, environmental exposure during storage and shipment, and ease of handling, opening, presentation and use during the procedure.

In embodiments, interatrial pressure vent 100 can be assembled using components that have been pre-sterilized using one of the above methods or others that are well known and the final assembly may be accomplished in an aseptic manner to avoid contamination.

In embodiments, the interatrial pressure vent 100 can be supplied non-sterile and be sterilized around the time of use using one of the above methods or by other methods well known by those skilled in the art.

Similarly, the placement catheter 111 may be pre-sterilized and packaged separately from the interatrial pressure vent 100. Sterilization can be performed using a similar method to the interatrial pressure vent 100 or using a different method from the same choices or using some other method as is well known by those skilled in the art.

In embodiments, an interatrial pressure vent 100 and the placement catheter 111 can be supplied pre-sterile and in the same package. In another aspect, the interatrial pressure vent 100 and the placement catheter 111 can be preloaded and supplied pre-sterile.

Prior to insertion, the interatrial pressure vent 100 is preferably folded and stowed onto the placement catheter 111. This can be accomplished in a sterile field and using aseptic techniques in the following steps. First the interatrial pressure vent 100 is presented to the sterile field and the placement catheter 111 is presented to the sterile field. Second, the interatrial pressure vent 100 and placement catheter 111 are inspected for visible signs of damage, deterioration or contamination. Third, the second handle component 129 of the placement catheter 111 is retracted fully so the outer shaft 113 exposes the inner shaft 112 to the maximum extent allowed. Fourth, the interatrial pressure vent 100 is positioned in the correct orientation over the inner shaft 113 of the placement catheter 111 with the inner shaft 113 oriented through the center of the flow control element 104. Fifth, the flange segments 102*a-h* and 103*a-h* are folded away from each other and the flange segments 102*a-h* and 103*a-h* and the core segment 106 are compressed radially to fold the interatrial pressure vent 100 into a size and shape that will fit over and onto the waist section 120 of the inner shaft 112 with the distal ends 115 of flange segments 102*a-h* aligning with the proximal groove 114 of inner shaft 112. In embodiments comprising a flange as described in FIG. 11A the flange segments 102*a-h* and 103*a-h* are folded away from each other and the flange segments 102*a-h* and 103*a-h* and the core segment 106 are compressed radially to fold the interatrial pressure vent 100 into a size and shape that will fit over the flange 3000 described on FIG. 11A. This folding may be accomplished with the aid of an insertion tool (not shown) that retains the interatrial pressure vent 100 in a stowed position on inner shaft 112 and then advancing outer shaft 113 over the stowed interatrial pressure vent 100 and displacing the insertion tool, thereby leaving the outer shaft 113 completely covering the interatrial pressure vent 100 and mating with the distal tapered tip 140 of the inner shaft 112. In other embodiments, this can be accomplished by hand using the fingers of one hand to hold the distal ends 115 of the flange segments 102*a*-102*h* in position at groove 114 of the inner shaft 112 and advancing the outer shaft 113 over the inner shaft 112 enough to hold the flange segments 102*a*-102*h* in place. Completion of the loading procedure is accomplished by progressively advancing the outer shaft 113 until it completely covers the interatrial pressure vent 100 as shown in FIGS. 11 and 11A. While the below discussion regarding placement of the interatrial pressure vent uses the placement device shown in FIGS. 9-11 as an example, the description on placement and the procedure therefore is also meant to apply to embodiments where the inner shaft comprises a flange rather than grooves.

Figure 13:
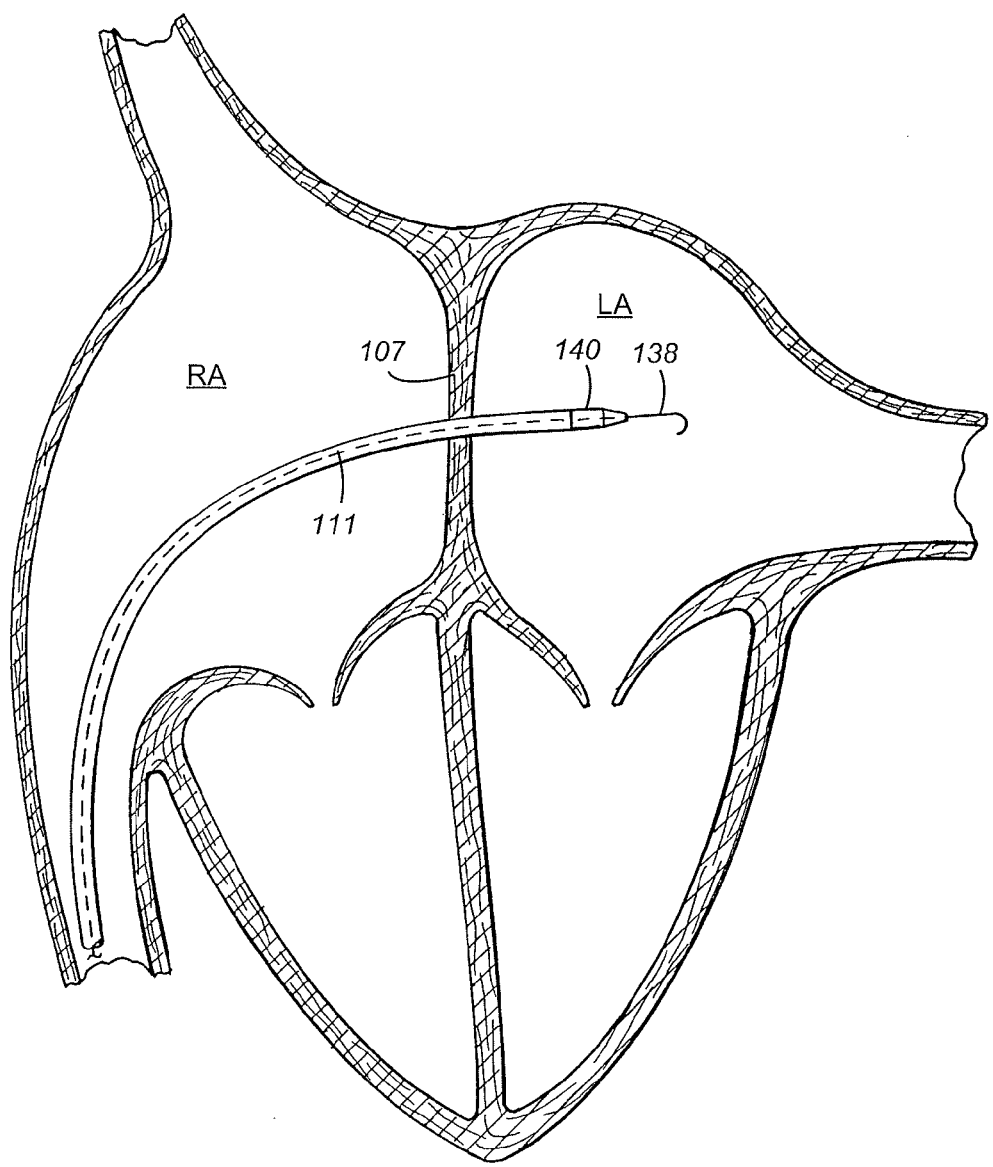
FIG. 13 is a cutaway view of a heart of a patient and the distal end of a placement catheter in position across the interatrial septum.

Positioning of the loaded interatrial valve 100 and placement catheter 111 in preparation for implanting the interatrial valve 100 in the patient can be accomplished by: first gaining vascular access; second, positioning a guidewire 121 in the right atrium of the patient; third, positioning an introducer (not shown) into the patients right atrium; fourth, locating the interatrial septum; fifth, advancing the introducer through the interatrial septum and into the patient's left atrium; sixth, advancing the guidewire 138 into the left atrium; seventh, retracting the introducer; eighth, advancing the loaded placement catheter 111 and interatrial pressure vent 100 into position so the distal end and approximately half of the stowed length of the interatrial pressure vent 100 is protruding through the interatrial septum and into the patient's left atrium as shown in FIG. 13.

In embodiments, positioning of the loaded interatrial valve 100 and placement catheter 111 in preparation for implanting the interatrial valve 100 in the patient can be accomplished by: first gaining vascular access; second, positioning a guidewire 138 in the right atrium of the patient; third, advancing the loaded interatrial valve 100 and placement catheter 111 over guidewire 138 by inserting the guidewire into and through lumen 136 and advancing placement catheter 111 into the patient's right atrium; fourth, locating the interatrial septum; fifth, advancing the placement catheter 111 through the interatrial septum and into the patient's left atrium so the distal end and approximately half of the stowed length of the interatrial pressure vent 100 is protruding through the interatrial septum and into the patient's left atrium as shown in FIG. 13.

Figure 14:
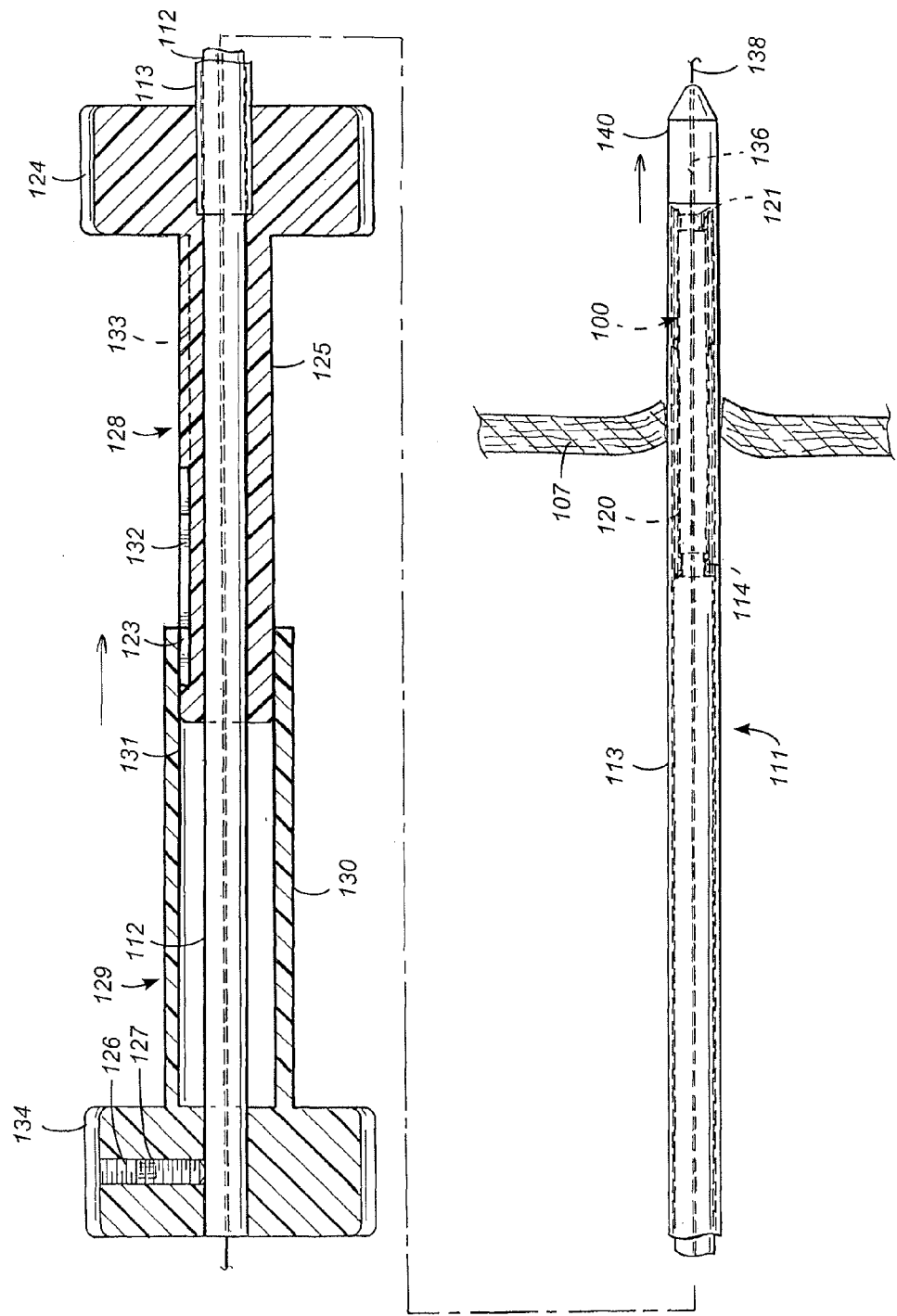
FIG. 14 is a schematic cross sectional side view of the proximal and distal end of a placement catheter in a closed position and positioned across the interatrial septum of the heart of a patient.
Figure 15:
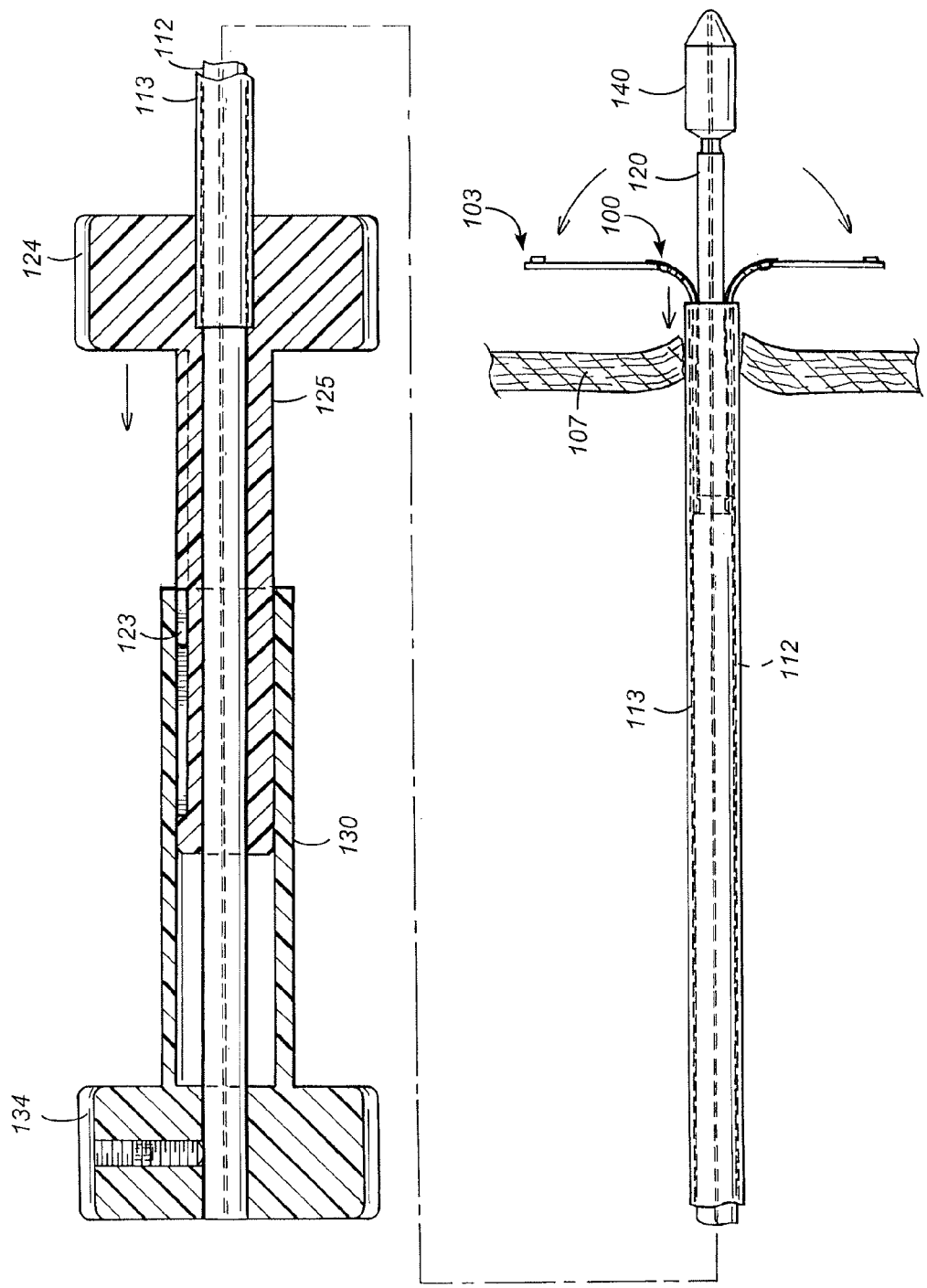
FIG. 15 is a view similar to FIG. 14 but showing the distal end of the placement catheter in a partially open position and the distal flange segments of the interatrial pressure vent deployed.
Figure 16:
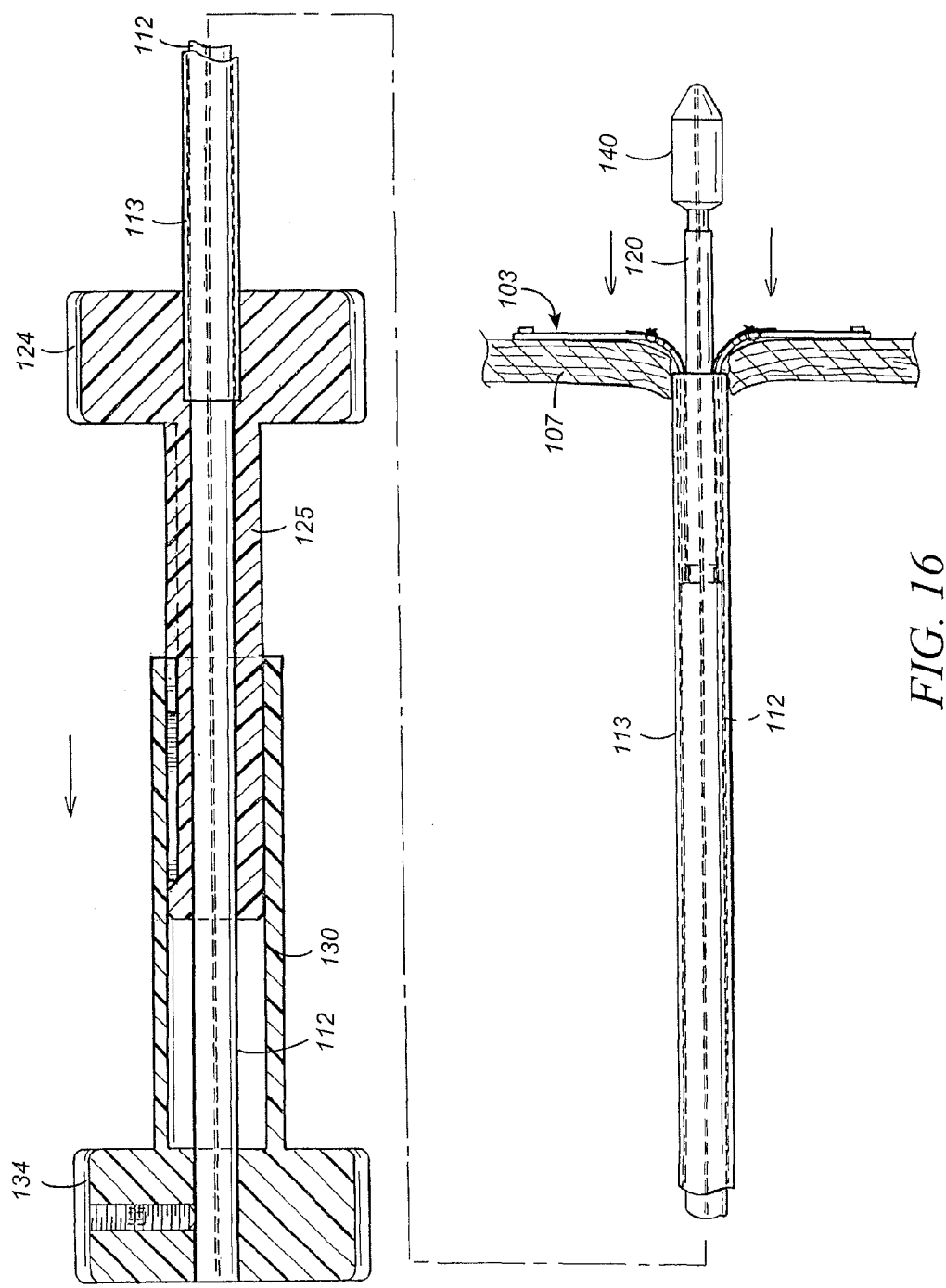
FIG. 16 is a view similar to FIG. 15 but showing the distal flange segments of the interatrial pressure vent in position against the wall of the interatrial septum.
Figure 18:
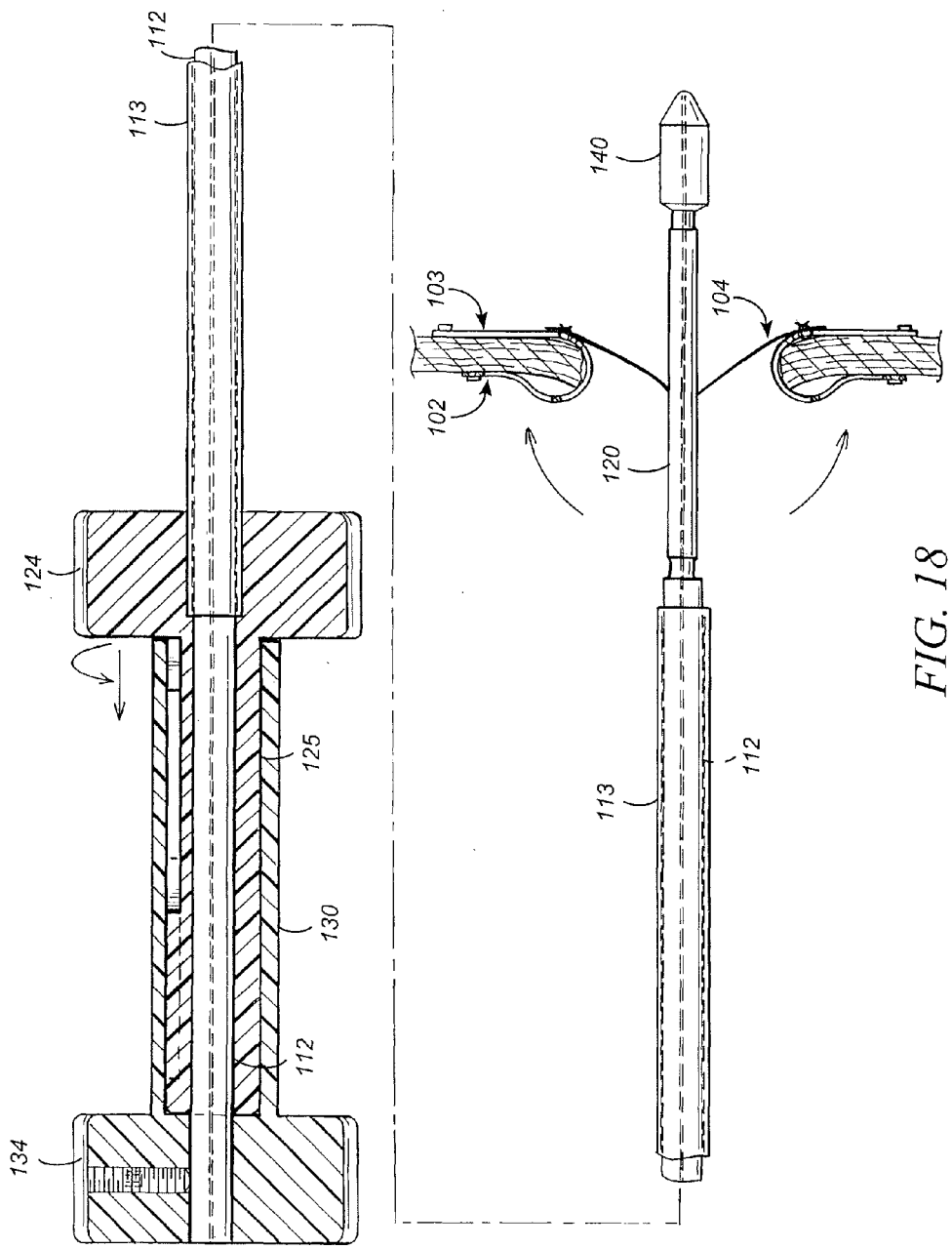
FIG. 18 is a view similar to FIG. 16 but showing further deployment of the interatrial pressure vent by releasing the proximal flange segments if imaging determines a correct positioning of the distal flange segments.
Figure 19:
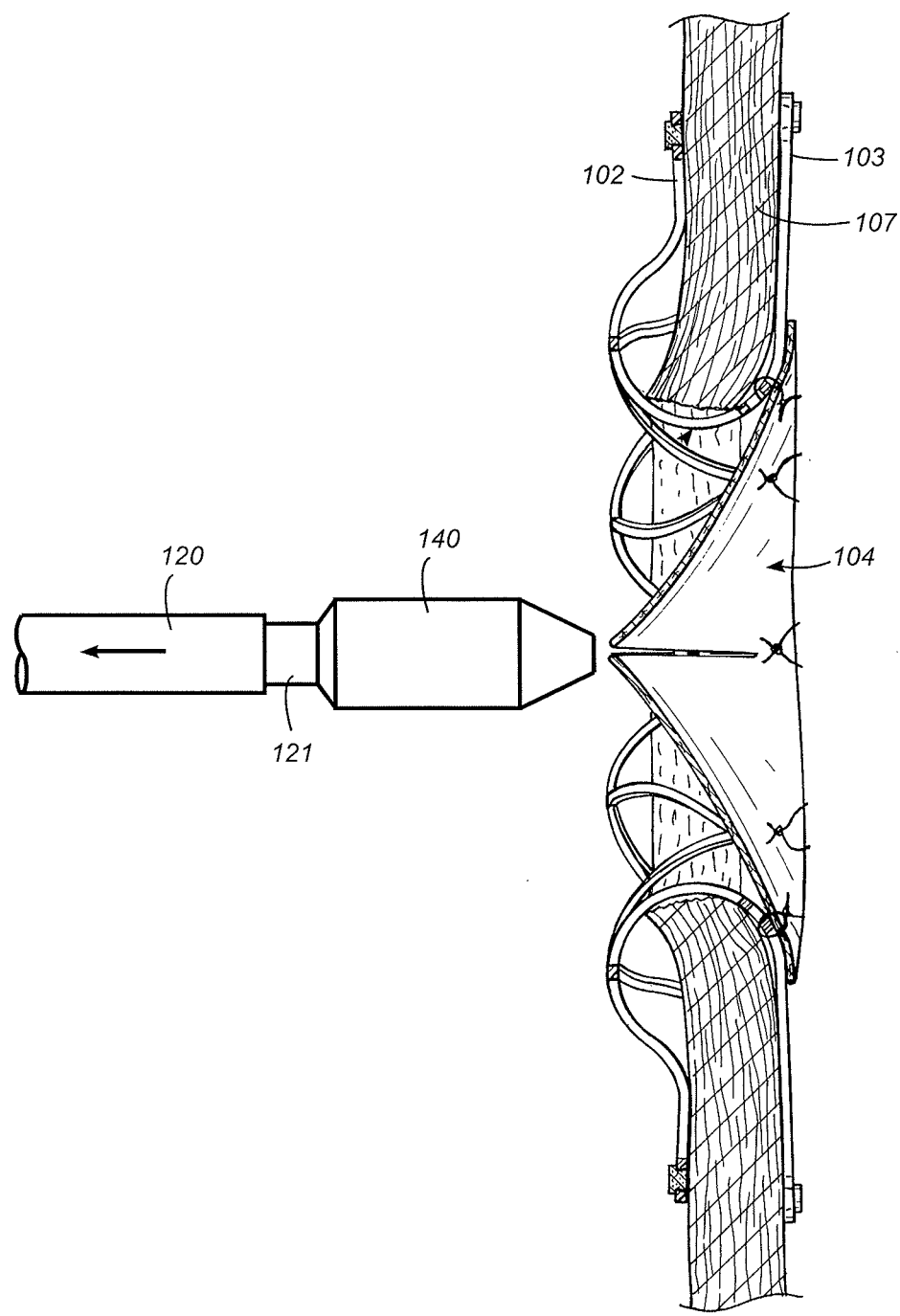
FIG. 19 is an enlarged cross-sectional detail view of the placement; catheter of FIG. 18 but showing the interatrial pressure vent fully released in position and the placement catheter being removed.

Implanting interatrial pressure vent 100 into a patient can be accomplished, once the loaded interatrial pressure vent 100 and placement catheter 111 are in position as shown in FIG. 14, by first, retracting first handle component 128 toward second handle component 129 while holding second handle component 129 until flange segments 103*a-h* are fully uncovered as shown in FIG. 15, and as can be verified by visualizing the markers 119 using fluoroscopy or MRI or using echocardiography; second, retracting the placement catheter 111 with partially deployed interatrial pressure vent 100 toward the patient's right atrium until the flange segments 103*a-h* are in contact with the left atrial side of the interatrial septum, as shown in FIG. 16, and as can be verified using the same techniques mentioned or as can be perceived by the user based on the resistance felt against further proximal movement of the placement catheter 111; fourth, continuing to retract the outer sheath 113 by retracting second handle 129 until the outer sheath 113 is retracted beyond the proximal end of groove 114 of inner shaft 112 and also uncovers flange segments 102*a-h*, at which time the flange segments 102*a-h* of interatrial pressure vent 100 will deploy returning to the preloaded geometry and capture the interatrial septum between the flange segments 103*a-h* and flange segments 102*a-h* as shown in shown in FIG. 18; fifth, the inner sheath is retracted through the flow control element 104 of interatrial pressure vent 100, into the patients right atrium as shown in FIG. 19; fifth the second handle component 129 is advanced toward the first handle component 128 to reposition inner shaft 112 into the position relative to outer shaft 113 it was in during placement and the placement catheter is removed from the patient and the procedure is completed.

In other embodiments, implanting interatrial pressure vent 100 into a patient can be accomplished, once the loaded interatrial pressure vent 100 and placement catheter 111 are in position as shown in FIG. 14, by first, advancing second handle component 129 toward first handle component 130 while holding first handle component 128 until flange segments 103*a-h* are fully uncovered as shown in FIG. 15, and as can be verified by visualizing the markers 119 using fluoroscopy or MRI or using echocardiography; second, retracting the placement catheter 111 with partially deployed interatrial pressure vent 100 toward the patient's right atrium until the flange segments 103*a-h* are in contact with the left atrial side of the interatrial septum, as shown in FIG. 16, and as can be verified using the same techniques mentioned or as can be perceived by the user based on the resistance felt against further proximal movement of the placement catheter 111; fourth, continuing to retract the outer sheath 113 by retracting second handle 129 until the outer sheath 113 is retracted beyond the proximal end of groove 114 of inner shaft 112 and also uncovers flange segments 102*a-h*, at which time the flange segments 102*a-h* of interatrial pressure vent 100 will deploy returning to the preloaded geometry and capture the interatrial septum between the flange segments 103*a-h* and flange segments 102*a-h* as shown in shown in FIG. 18; fifth, the inner sheath is retracted through the flow control element 104 of interatrial pressure vent 100, into the patients right atrium as shown in FIG. 19; fifth the second handle component 129 is advanced toward the first handle component 128 to reposition inner shaft 112 into the position relative to outer shaft 113 it was in during placement and the placement catheter is removed from the patient and the procedure is completed.

For a variety of reasons, it may be necessary or desirable to remove interatrial pressure vent 100 and placement catheter 111 during any part of the procedure without further risk or injury to the patient. This is possible as follows: if, for any reason, it is desired for the device to be removed before outer shaft 113 is retracted and flange segments 103*a-h* are deployed, then the placement catheter 111 with interatrial valve 100 can simply be refracted out through the same pathway as introduced.

If, following deployment of flange segments 103*a-h* it is necessary or desirable to remove the device, then the interatrial valve 100 can be retracted into the placement catheter 111 by advancing first handle 128 away from second handle 129, while holding second handle 129 stationary, thereby advancing outer sheath 113 distally through the interatrial septum and over the flange segments 103*a-h*. In embodiments, radiopaque markers 118 placed in marker holes 109 are captured in groove 114 (see FIG. 17) and cannot fit in the gap between waist 120 of inner shaft 112 and inner surface of outer shaft 113, so as outer sheath 113 is advanced, flange segments 103*a-h* are forced to fold inward toward their stowed position and are retracted back onto inner shaft 112 and within outer sheath 113. Once outer shaft 113 is fully advanced, catheter 111 can be retracted as shown in FIG. 17 to be removed out through the interatrial septum and out through the same pathway as introduced.

Figure 19A:
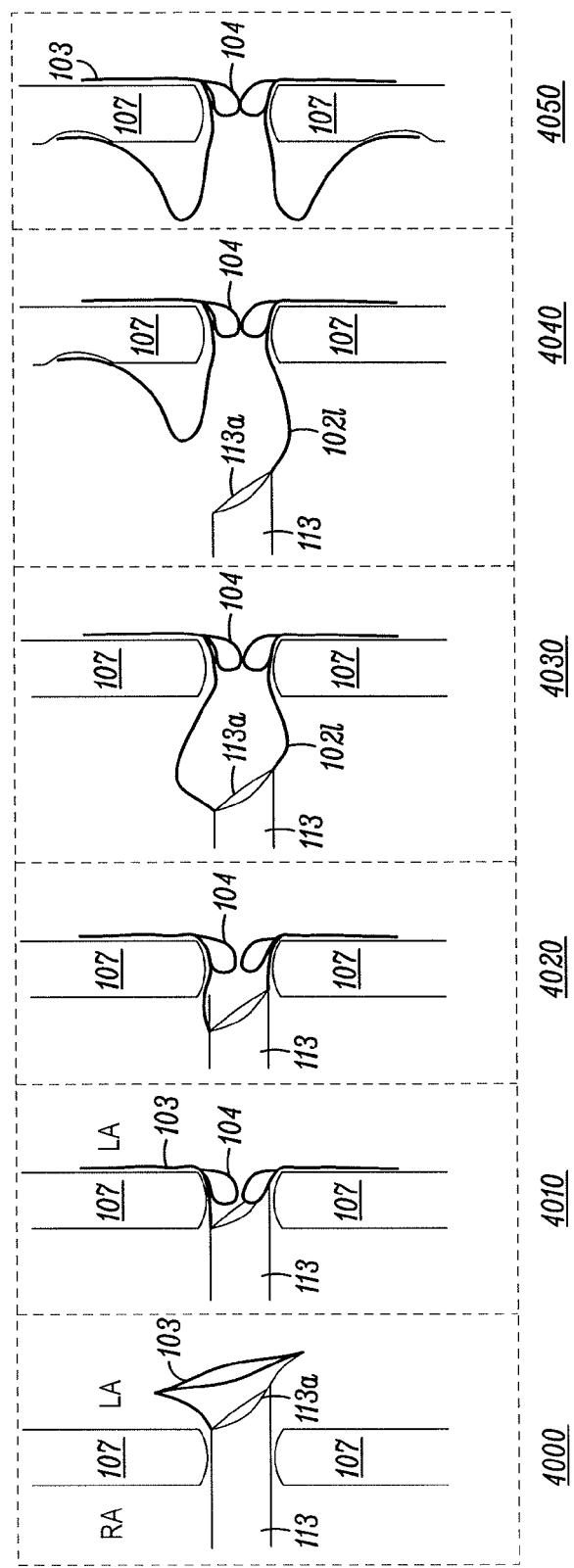
FIG. 19A is schematic depiction of another embodiment of a placement catheter system and interatrial pressure device along with the deployment process therefor.

FIG. 19A is embodiment of the invention designed to enhance the retrievability of the device. The procedure for implanting the device is substantially similar to that which is described above; however, there are variations to the placement catheter and the device, which will be described below. As discussed in connection with FIGS. 7A through 7C, embodiments of the interatrial venting device comprise at least one flange segment being longer than the other flange segments. The embodiment schematically shown in FIG. 19A preferably works with such embodiments having at least one flange segment that are longer in relation to the other flange segments; thus the segments shown in the RA have the same reference number as the longer segments in FIGS. 7A through 7C, i.e., 102 L. In embodiments utilizing the techniques shown in FIG. 19A, the opening 113*a* of outer sheath 113 of placement catheter is angled or has a more surface area on one side relative to the other. The placement catheter is oriented during the procedure such that the angled opening (or the plane of the opening itself) is at an angle more normal to the septal wall 107. In the embodiment shown in FIG. 19A, that angle appears to be around 45 degrees with respect to the septal wall 107, but any angle which provides an more normal angle with respect to the septal wall may be used, and any opening which provides more surface area of the outer sheath 113 on one side with respect to the other side may be used. Reference numerals 4000 through 4050 refer to steps in the process described below. The process is largely similar to that described above or with respect to any well-known placement catheter system and process, therefore only the applicable differences will be described. As can be seen at steps 4000 through 4020, the placement catheter is positioned and the device is in the beginning stages of deployment. At steps 4030 and 4040, the as the outer sheath 113 is retracted and on the RA side (or when the inner shaft is advanced while the outer sheath is on the RA side, which is not shown), the opening allows one of the longer flange segments 102L to be deployed after other flange segments have been deployed and are thus in contact with the septum 107. The at least one longer flange segment 102L is retained in the placement catheter system by way of the outer sheath 113, the length of which extends further on one side than the other due to the opening and thus covers the longer segment 102L while the other shorter segments have been deployed. In this way, the operator of the placement catheter can determine if the interatrial device is in the proper position. If not, the operator can still retrieve the device up until the last point prior to full deployment, i.e., when at least one of the longer flange segments (102L for example) is still retained in the placement catheter by the outer sheath 113. If it is in proper position, the deployment may commence.

Figure 19B:
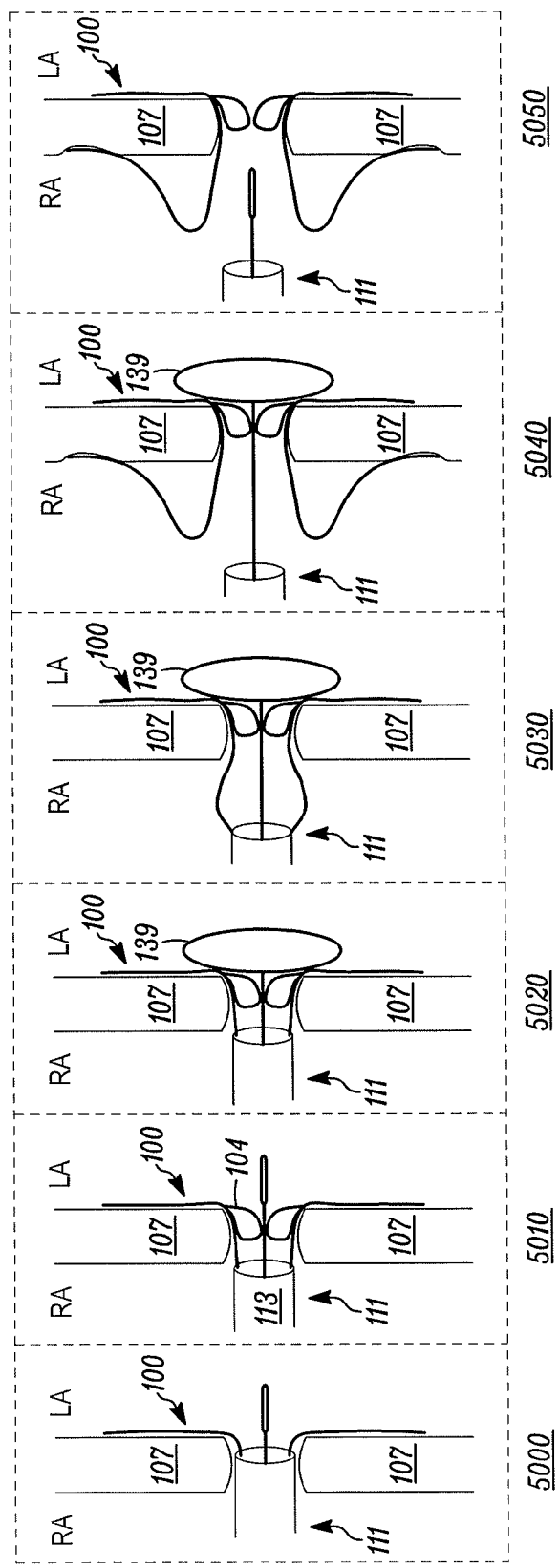
FIG. 19B is schematic depiction of another embodiment of a placement catheter system and deployment process therefor.

Another deployment embodiment is now described in connection with FIG. 19B. This deployment embodiment may be used with any embodiment of the interatrial vent described herein. Reference numerals 5000 through 5050 refer to steps in the process described below. At step 5000, the LA side of the device (generally referred to in this figure as 100) is deployed on the LA side of the heart. Further deployment is shown at step 5010 and the outer sheath is retracted into the RA side of the heart, which allows flow control element 104 to exit the placement catheter. Placement catheter is equipped with a balloon, which is in fluid communication, for example, with lumen 136 described above or guide wire 138. The skilled artisan will appreciate other configurations in which a balloon catheter may be provided in the placement catheter system. Upon deployment of the LA side flange or shortly thereafter, balloon 139 is inflated (shown in step 5020). The inflation of the balloon optionally coupled with a pulling-back motion of the placement catheter 111 holds the device 100 against the LA side of the septal wall 107 and thereby prevents the device 100 from dislodging during deployment and/or moving in a direction away from the septal wall. Step 5040 shows the full deployment of the device 100 while the balloon 139 is inflated. When satisfactory deployment is achieved, the balloon 139 is deflated and the placement catheter system is removed (shown at step 5050).

Figure 20:
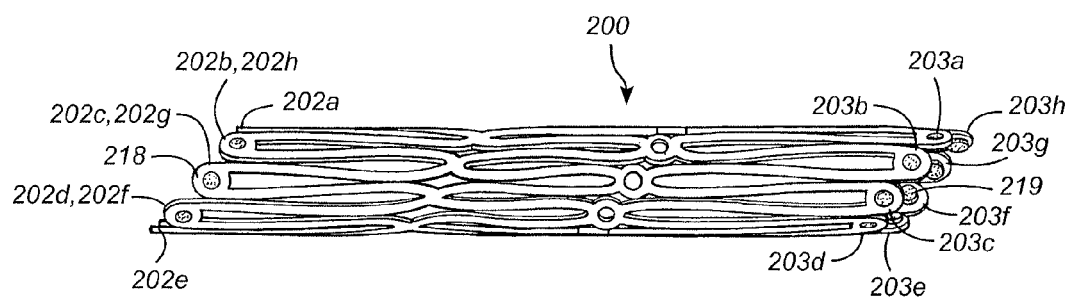
FIG. 20 is a side elevational view of an alternate embodiment of an interatrial pressure vent body with slanted flange segment ends.

Now referring to FIG. 20, an interatrial pressure vent 200 of the present invention is shown. In embodiments, flange segments 202*a-h* and 203*a-h* can be formed with graduating length to reduce interference between flange segments 202*a-h* and 203*a-h* during handling, folding and loading. In embodiments, radiopaque markers 218 and 219 protrude into the inner cylindrical shape of the stowed position of the interatrial pressure vent and each flange segment 202*a-h* and 203*a-h* differ in length by at least the width of the radiopaque markers 218 and 219. In embodiments, each flange segment 202*a-h* and 203*a-h* differ in length by at least at least 1 mm. In embodiments, each flange segment 202*a-h* and 203*a-h* differ in length by at least 2% of the overall length of interatrial pressure vent 200 in the position shown in FIG. 20.

Figure 21:
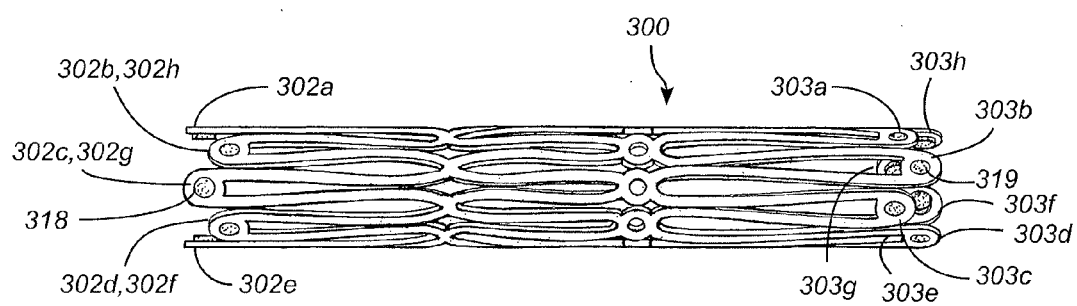
FIG. 21 is a side elevational view of an alternate embodiment of an interatrial pressure vent body with staggered flange segment ends.

Now referring to FIG. 21, an interatrial pressure vent 300 of the present invention is shown. In embodiments, flange segments 302*a-h* and 303*a-h* can be formed with alternating length to reduce interference between flange segments 202*a-h* and 203*a-h* during handling, folding and loading. In embodiments radiopaque markers 318 and 319 protrude into the inner cylindrical shape of the stowed position of the interatrial pressure vent 300 and alternating flange segments 302*a, c, e,* and *g* are longer than flange segments 302*b, d, f* and *h*, and correspondingly, flange segments 303*b, d, f* and *h* are longer than flange segments 303*a, c, e* and *g* by at least the width of the radiopaque marker. In embodiments, alternating flange segments 302*a, c, e* and *g* are longer than flange segments 302*b, d, f* and *h* and, correspondingly, flange segments 303*b, d, f* and *h* are longer than flange segments 303*a, c, e* and *g* by at least 1 mm. In one aspect the alternating flange segments 302*a, c, e* and *g* are longer than flange segments 302*b, d, f* and *h* and, correspondingly, flange segments 303*b, d, f* and *g* are longer than flange segments 303*a, c, e* and *g* by at least 2% of the overall length of interatrial pressure vent 300 in the position shown in FIG. 21.

Figure 22:
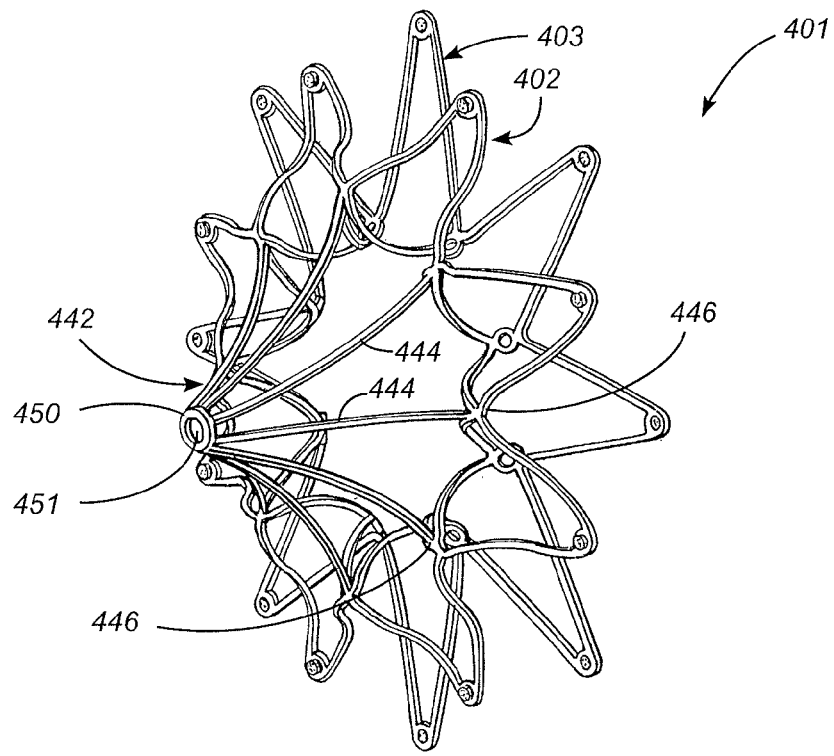
FIG. 22 is a perspective view of an alternate embodiment of an interatrial pressure vent body with an integrated retrieval means and thrombus clot strainer.
Figure 23:
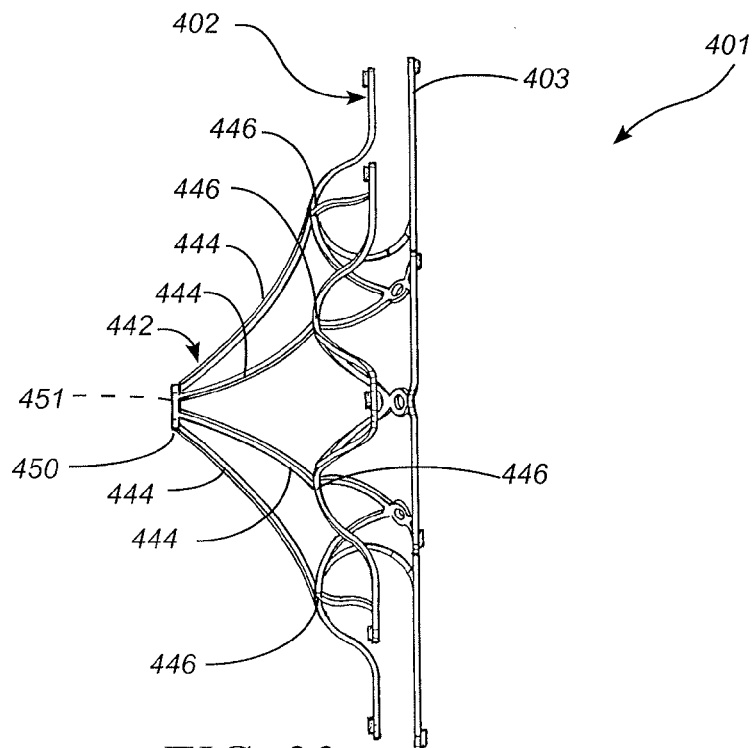
FIG. 23 is a right side view of the body assembly of FIG. 22.

Referring now to FIG. 22 and FIG. 23, the body element 401 of an interatrial pressure vent with integral thrombus filter and retrieval cone 442 of the present invention is shown. In embodiments, conical struts 444 are affixed to body element 401 at attachment points 446 and converge at apex 450. In embodiments, conical struts 444 comprise single beams of similar material to flange segments 402 and 403 and can be attached to the body element or formed at the same time as the body element using techniques described in this specification, and are thus integral with the remainder of the device. In embodiments the space between adjacent struts 444 is about 2 mm. In embodiments, the space between adjacent struts 444 is about 4 mm. As can be appreciated, conical struts 444 will protrude into the right atrium of the patient after implant and spaces between conical struts will function to block the passage of solid material larger than the space between adjacent struts 444. This will provide the function of preventing emboli that are larger than the space between the adjacent struts 444 from passing from the right atrium to the left atrium.

Referring again to FIG. 22 and FIG. 23, in embodiments the shape of the conical struts 444 is not straight. In embodiments the shape of the conical struts 444 can be concave when viewed on end as depicted in FIG. 22. In embodiments the conical struts can be curved in a direction away from the chord formed between the apex 450 and the attachment points 446. In embodiments there can be a hole 451 through apex 450 large enough to receive a retrieval snare (not shown). It can be appreciated that conical struts 444 and apex 450 can be used to aid retrieval of the interatrial pressure vent from a patient at some time after the implant procedure using a method as follows: A catheter tube with an internal lumen at least as large as apex 450 can be placed into the patients right atrium using standard techniques and imaging equipment. A retrieval snare can be fabricated from the proximal end of a guidewire bent sharply by about 180 degrees and this snare can be inserted through the catheter tube and advanced into the patient's right atrium and with the assistance of fluoroscopy advanced through hole 451 or around conical struts 444. Once the retrieval snare is engaged in this manner, it will be possible to retract the interatrial pressure vent by advancing a catheter tube while holding slight tension on the snare and thereby guide the catheter tube over apex 450 and onto conical struts 444. As the catheter tube continues to advance, with some tension on the snare it will be possible to force the conical struts inward, thereby forcing the flange segments 402 to begin folding inwards. When the conical struts are nearly completely in the catheter tube, the catheter tube can be held in a stationary position and the snare wire retracted against it, thereby causing the attachment points 446 between the conical struts 444 and the flange segment 402 to be retracted into the catheter. Flange segments 402 can begin to be retracted into the catheter at this point and the distal ends of flange segments 402 can be diverted toward the patients left atrium but will also fold inward and into the catheter. Once the flange segments 402 are inside of the catheter tube, the snare can be held stationary and the catheter tube can be advanced further, through the interatrial septum and over flange segments 403. Once the flange segments 403 are retracted into the catheter, the catheter and snare can be moved together to retract the interatrial pressure vent into the patient's right atrium and out through the pathway through which it was introduced.

Figure 24:
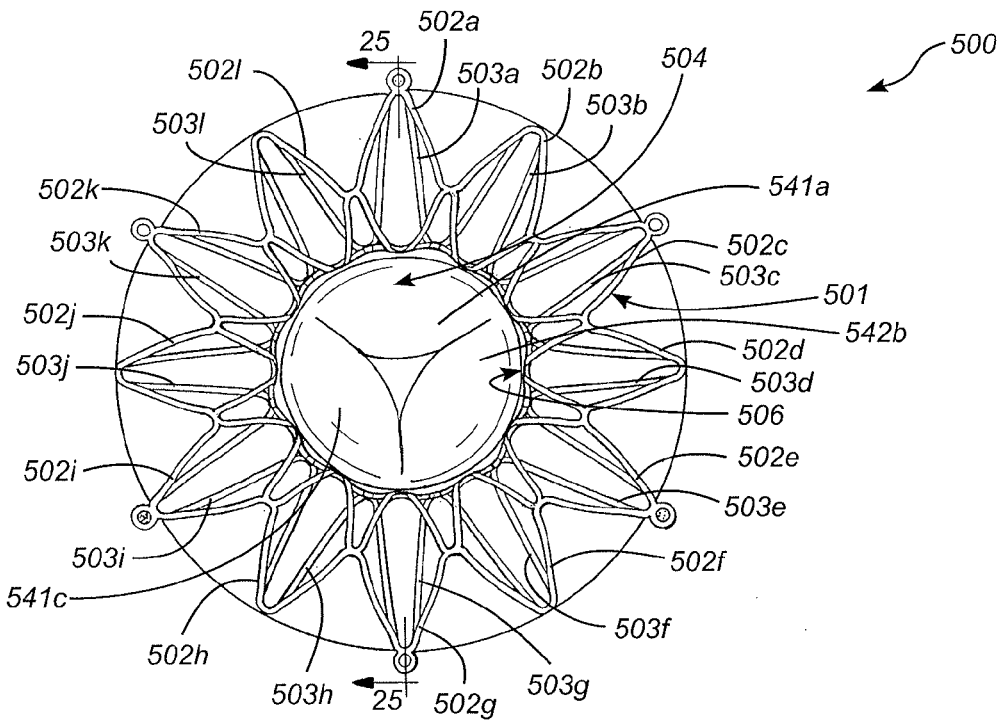
FIG. 24 is an end view of an alternate embodiment of interatrial pressure vent.
Figure 25:
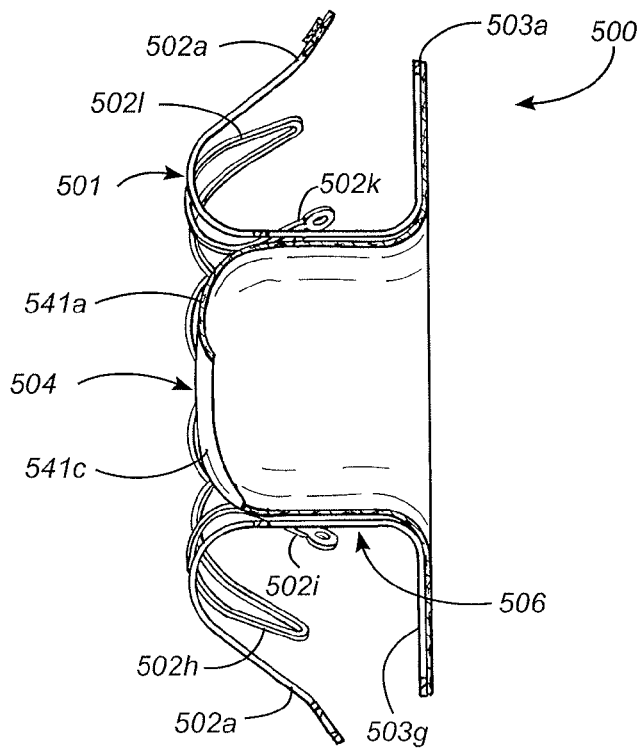
FIG. 25 is a cross-sectional side view taken along line 25-25 of FIG. 24.

Referring now to FIGS. 24 and 25 an alternate embodiment of interatrial pressure vent 500 is shown. In embodiments, flow control element 504 is comprised of leaflets 541*a-c*. Body element 501 is comprised of core segment 506 and flange segments 502*a*-1 and 503*a*-1 (not fully visible in FIG. 25); the number of flange segments being a multiple of the number of leaflets. This configuration improves the symmetry of strain against the flow control leaflets and also improves the uniformity of motion by the flow control element to changes in blood flow.

In embodiments the number of leaflets comprising the flow control element is three and the number of flange segments on each side of the core segment is twelve. In embodiments, the number of leaflets comprising the flow control element is three and the number of flange segments on each side of the core segment is nine. In embodiments, the number of leaflets comprising the flow control element is three and the number of flange segments on each side is six.

In embodiments, the number of leaflets comprising the flow control element is three and the number of flange segments on each side is three. In embodiments, the number of leaflets comprising the flow control element is three, the number of flange segments on one side of the core segment is twelve and the number of flange segments on the other side of the core segment is nine. In embodiments, the number of leaflets comprising the flow control element is three, the number of flange segments on one side of the core segment is twelve and the number of flange segments on the other side of the core segment is six.

In embodiments, the number of leaflets comprising the flow control element is three, the number of flange segments on one side of the core segment is twelve and the number of flange segments on the other side of the core segment is three. In embodiments, the number of leaflets comprising the flow control element is three, the number of flange segments on one side of the core segment is nine and the number of flange segments on the other side of the core segment is six. In embodiments, the number of leaflets comprising the flow control element is three, the number of flange segments on one side of the core segment is nine and the number of flange segments on the other side of the core segment is three.

In embodiments, the number of leaflets comprising the flow control element is three, the number of flange segments on one side of the core segment is six and the number of flange segments on the other side of the core segment is three. In embodiments, the number of leaflets comprising the flow control element is two and the number of flange segments on each side of the core segment is twelve. In embodiments, the number of leaflets comprising the flow control element is two and the number of flange segments on each side of the core segment is ten. In embodiments, the number of leaflets comprising the flow control element is two and the number of flange segments on each side of the core segment is eight.

In embodiments, the number of leaflets comprising the flow control element is two and the number of flange segments on each side of the core segment is six. In embodiments, the number of leaflets comprising the flow control element is two and the number of flange segments on each side of the core segment is four. In embodiments, the number of leaflets comprising the flow control element is two and the number of flange segments on each side of the core segment is two.

In embodiments, the number of leaflets comprising the flow control element is two, the number of flange segments on one side of the core segment is twelve and the number of flange segments on the other side of the core segment is ten. In embodiments, the number of leaflets comprising the flow control element is two, the number of flange segments on one side of the core segment is twelve and the number of flange segments on the other side of the core segment is eight. In embodiments, the number of leaflets comprising the flow control element is two, the number of flange segments on one side of the core segment is twelve and the number of flange segments on the other side of the core segment is six. In embodiments, the number of leaflets comprising the flow control element is two, the number of flange segments on one side of the core segment is twelve and the number of flange segments on the other side of the core segment is four. In embodiments, the number of leaflets comprising the flow control element is two, the number of flange segments on one side of the core segment is twelve and the number of flange segments on the other side of the core segment is two. In embodiments, the number of leaflets comprising the flow control element is two, the number of flange segments on one side of the core segment is ten and the number of flange segments on the other side of the core segment is eight.

In embodiments, the number of leaflets comprising the flow control element is two, the number of flange segments on one side of the core segment is ten and the number of flange segments on the other side of the core segment is six. In embodiments, the number of leaflets comprising the flow control element is two, the number of flange segments on one side of the core segment is ten and the number of flange segments on the other side of the core segment is four. In embodiments, the number of leaflets comprising the flow control element is two, the number of flange segments on one side of the core segment is ten and the number of flange segments on the other side of the core segment is two.

In embodiments, the number of leaflets comprising the flow control element is two, the number of flange segments on one side of the core segment is ten and the number of flange segments on the other side of the core segment is two. In embodiments, the number of leaflets comprising the flow control element is two, the number of flange segments on one side of the core segment is eight and the number of flange segments on the other side of the core segment is six. In embodiments, the number of leaflets comprising the flow control element is two, the number of flange segments on one side of the core segment is eight and the number of flange segments on the other side of the core segment is four.

In embodiments, the number of leaflets comprising the flow control element is two, the number of flange segments on one side of the core segment is eight and the number of flange segments on the other side of the core segment is two. In embodiments, the number of leaflets comprising the flow control element is two, the number of flange segments on one side of the core segment is six and the number of flange segments on the other side of the core segment is four. In embodiments, the number of leaflets comprising the flow control element is two, the number of flange segments on one side of the core segment is six and the number of flange segments on the other side of the core segment is two.

In embodiments, the number of leaflets comprising the flow control element is two, the number of flange segments on one side of the core segment is four and the number of flange segments on the other side of the core segment is two.

Figure 26:
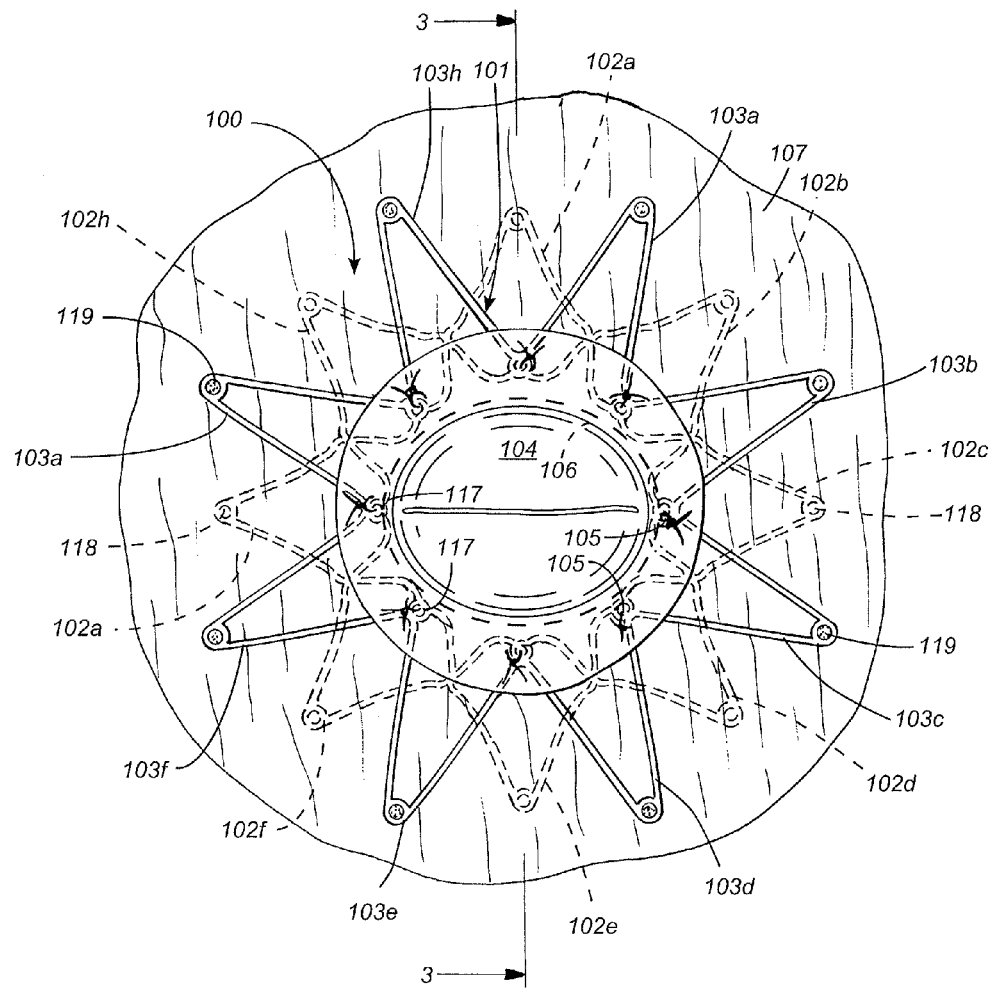
FIG. 26 shows and alternate embodiment wherein the core segment 106 is ovular rather than circular and thus the core segment is a cylindroid or elliptic cylinder rather than a simple cylinder.

FIG. 26 shows and alternate embodiment wherein the core segment 106 is ovular rather than circular and thus the core segment is a cylindroid or elliptic cylinder rather than a simple cylinder. This embodiment is more conducive to a bicuspid (or "duckbill", bivalve, or two-leaflet) configuration for the flow control element. The duckbill configuration is generally referred to as flow control element 104 in this figure.

The inventors have found that the bi-valve configuration is able to open more fully when coupled with a core segment in the shape of a cylindroid.

Figure 27:
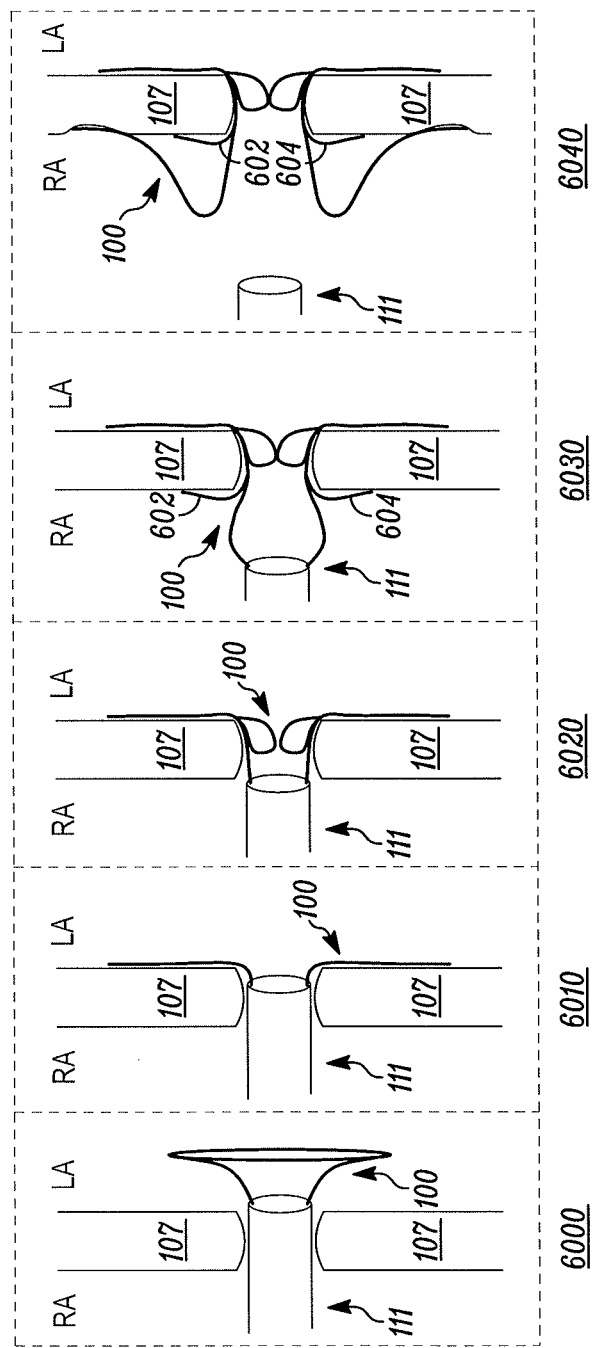
FIG. 27 is schematic depiction of another embodiment of a placement catheter system and interatrial pressure device along with the deployment process therefor.
Figure 27A:
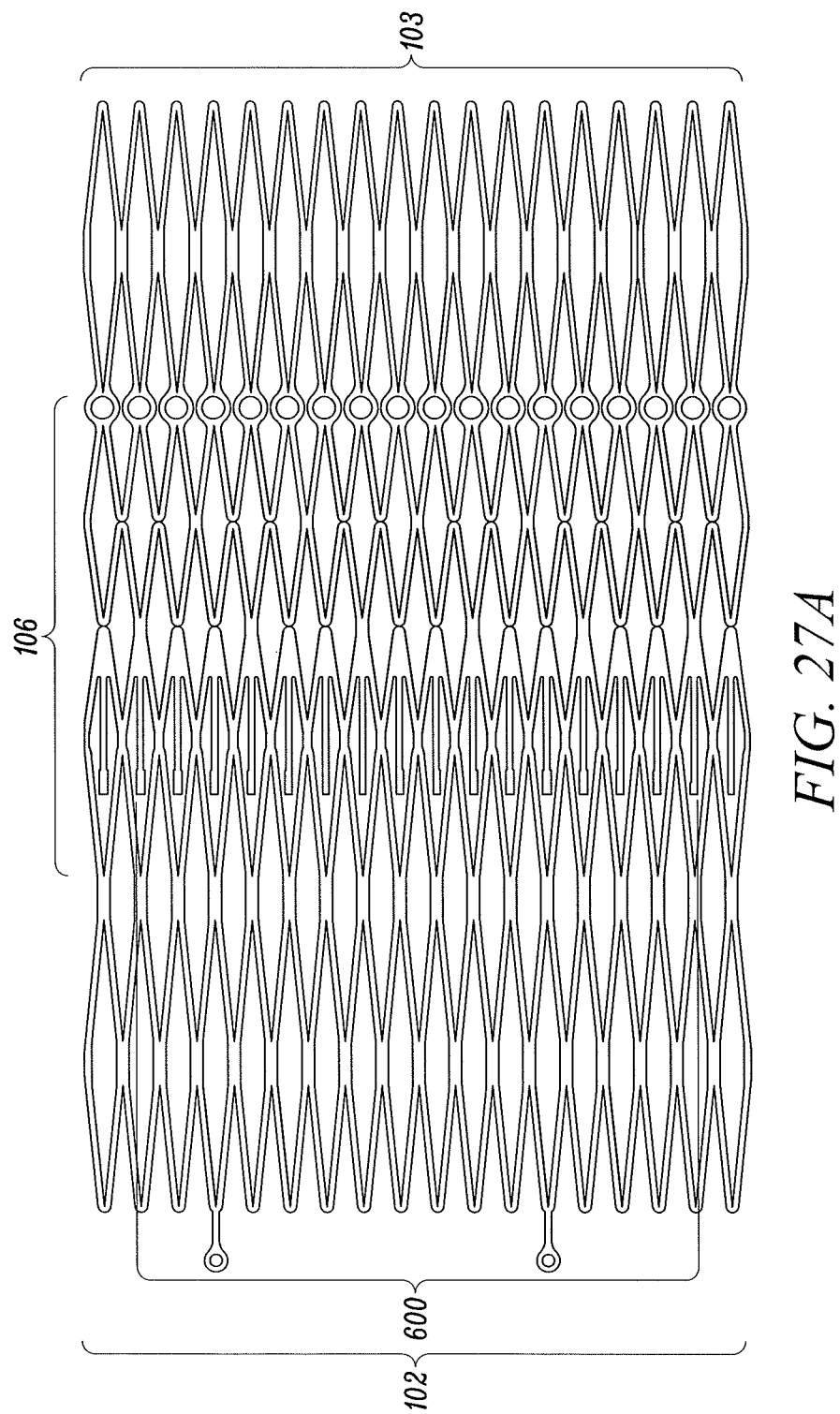
FIG. 27A is a side elevational view of the embodiment described in connection with FIG. 27 in the stowed position.

FIGS. 27 and 27A show another embodiment of an interatrial device having intermediate flange segments for a more secured fit against the septal wall. In embodiments, the intermediate flange segments are part of another a third annular flange situated on the same side of the septal wall as one of the other flanges. Reference numerals 6000 through 6040 refer to steps in the deployment of such an embodiment and will be discussed in connection with the structural features of the embodiment to illustrate this embodiment's utility and operation. The deployment process is similar to those described above, and to any commonly-known catheter based delivery process and as such the details of the process will not be discussed herein. Steps 6000 to 6020 show the deployment process steps proceeding in much the same manner as described herein. At step 6030, intermediate flange segments 602 and 604 of intermediate (or third) annular flange are deployed on the RA side. In this embodiment, intermediate flange segments 602 and 604 are shorter than the majority of the flange segments of the RA-side flange. As such, segments 602 and 604 are deployed prior to other longer segments and contact the septal wall 107 at points closer to the septal opening than the contact points of the longer segments. In this manner, the intermediate segments 602 and 604 (and the flange which they comprise) provide increased stability of the device. Any number of intermediate segments may be used although it is preferable to have at least two. As with other embodiments, the stiffness of the intermediate segments may be altered so as to differ from other flange segments of the device to avoid damage to the septal wall, i.e., lesser stiffness/greater flexibility, or to provide increased stability, i.e., greater stiffness/lesser flexibility. The choice of stiffness/flexibility variations must be balanced against the desired goals.

FIG. 27A is a side elevational view of embodiment discussed in connection with FIG. 27. In FIG. 27A the pressure venting device in its stowed configuration. Flanges 102 and 103 are shown with the flange segments that comprise them (flange segments not individually labeled). Core segment is again shown as 106. At a point between the end of the core segment 106 and proximal end of the RA side flange segment 102, the intermediate segments (collectively referred to as 600) emerge. Intermediate segments may be integral with the venting device or attached thereto in the manners described above.

Figure 28A:
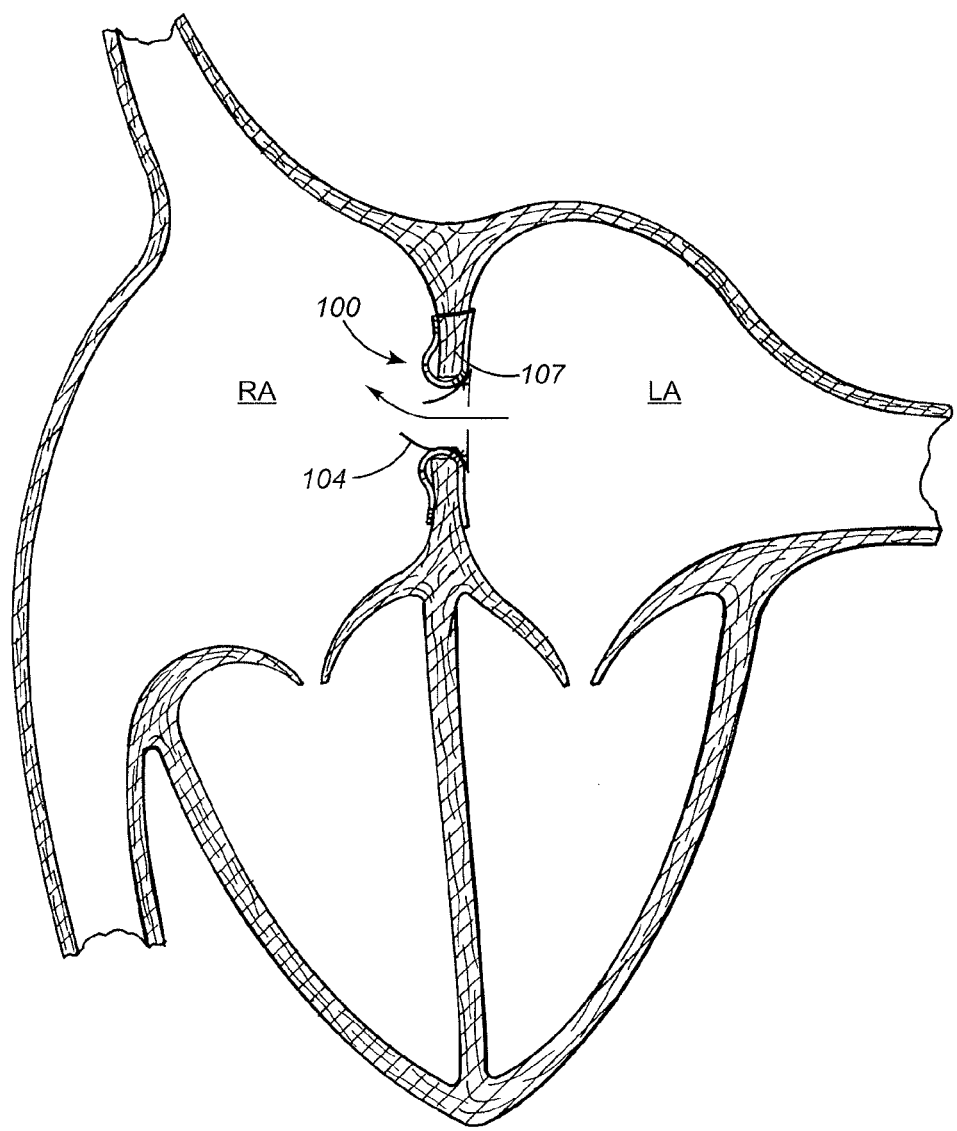
FIGS. 28A through 28C depict other embodiments of the device that direct the flow of blood in a desired direction.
Figure 28C:
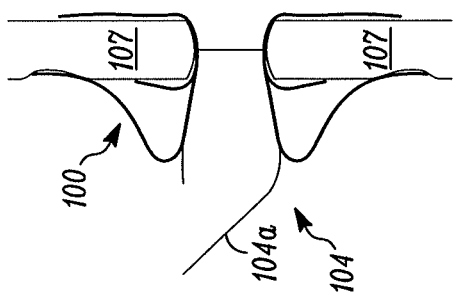
Figure 28B:
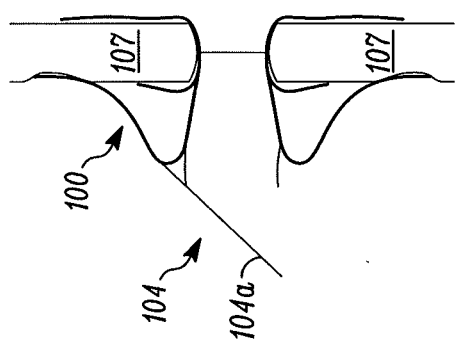

In other embodiments, the flow control element is configured to direct the blood flow in a desired direction. FIGS. 28A through 28C show such embodiments. In FIG. 28A interatrial device 100 is shown implanted in the atrial septum 107 of the heart in the same manner as shown in FIG. 1. Flow control element 104 is configured to aim the, shown in this figure as in the direction toward the superior vena cava. FIGS. 28B and 28C show a more detailed view of embodiments that enable the flow to be directed in a desired direction. As shown in FIG. 28B, flow control element comprises a baffle-like flange 104a that extends at a downward angle and in the corresponding direction. In use, such embodiment directs the flow downward. FIG. 28C shows an embodiment where the flow is directed upward. The valve material (e.g. material for leaflets) of the present invention can be sized and secured to the 100 in manner to direct the flow. For example, the flow control element may contain a curved tubular member whose opening points toward the direction of flow, or the flow control element may otherwise comprise an opening directed at the area of interest. In embodiments with baffles, the stiffness of the baffle 104a may be varied, for example, made stiffer. The length of the baffle can also be varied depending on the desired flow direction. The baffle can be a separate member attached to the flow control element or it may be made of the material and/or integral with the remainder of the flow control element.

Figure 29C:
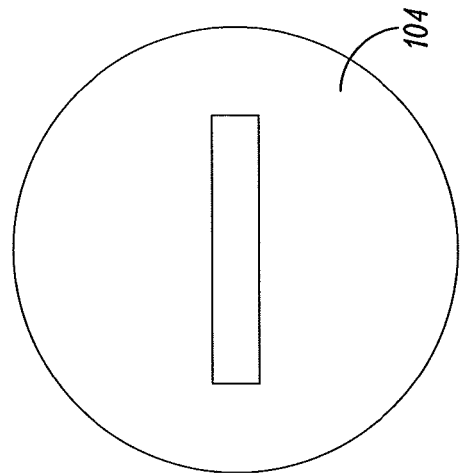
FIGS. 29A through 29C are an end-on view from the RA side of embodiments of exit profiles of the flow control element.
Figure 29B:
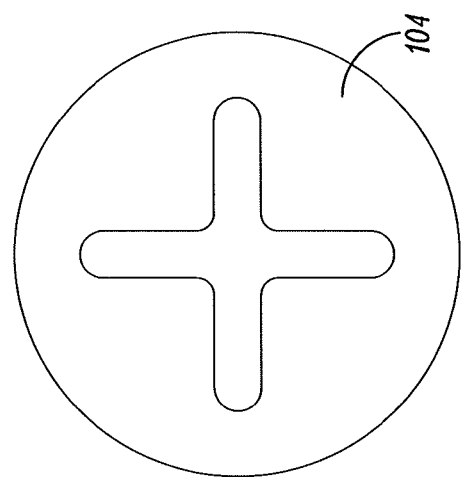
Figure 29A:
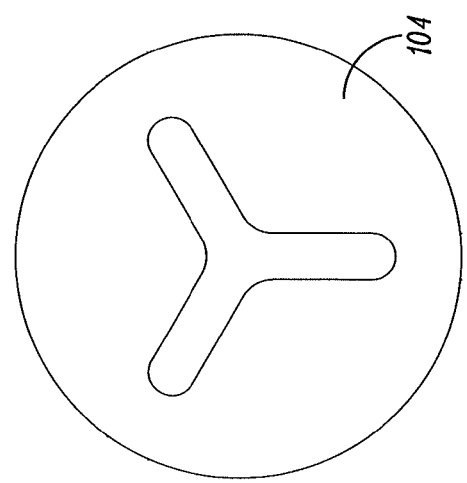

FIG. 29A through C show exit profile shapes of the flow control element 104. In these figures, the flow control element 104 is being viewed from the RA side and thus the direction of flow is understood to coming out of the page at an angle substantially normal to the page. If the flow control element is a valve as described herein, folding and suturing patterns may be employed to achieved these exit profile shapes. In other embodiments, the end of the flow control element may be provided with a plate, or a partially frustoconical end piece, having an opening defining the two-dimensional shape shown in the Figure. The skilled artisan will appreciate that other exit profile shapes may be fashioned. The selection of an exit profile shape may provide advantages such as directing flow, preventing thrombi from moving across the septal divide, and/or reducing injury to surrounding tissue.

Figure 30:
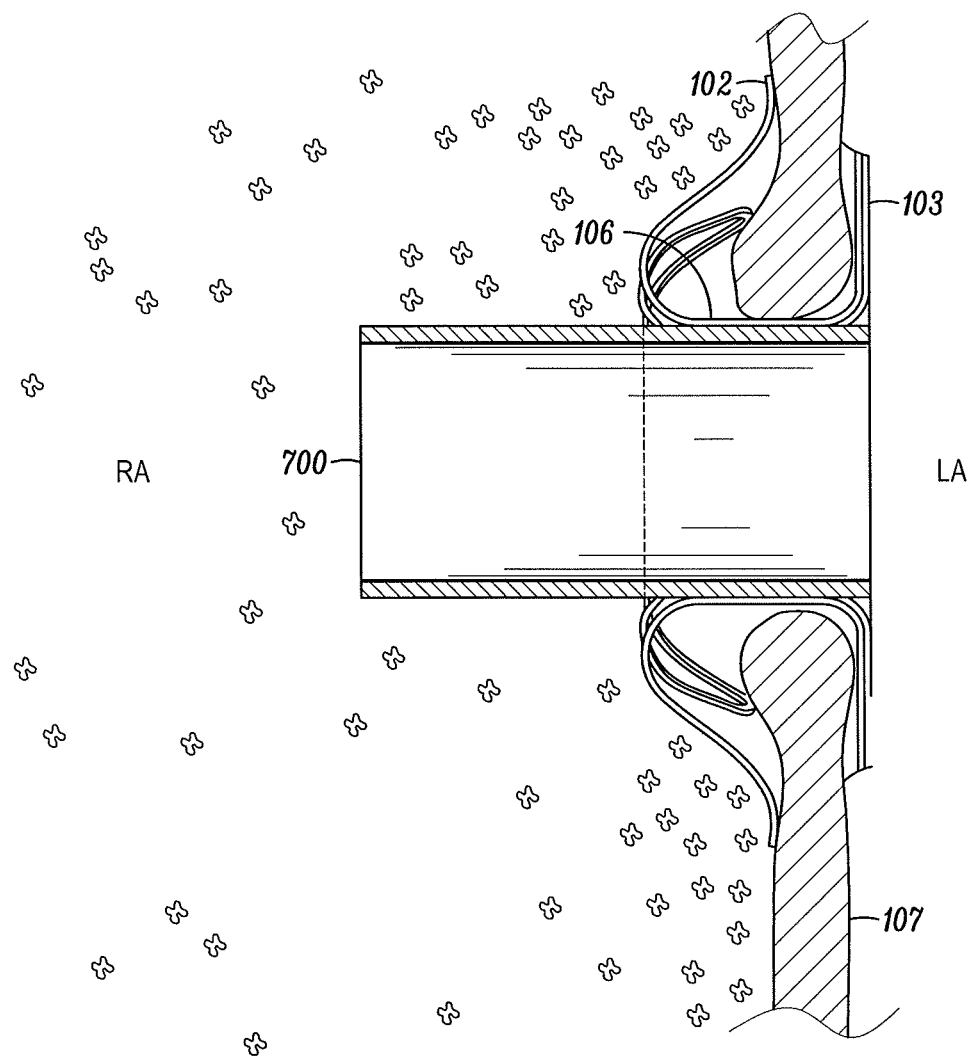
FIG. 30 is a side view of an embodiment of the device having a tube-like extension into the RA side of the heart.

Another embodiment of the invention is shown in FIG. 30. In this embodiment, the core segment 106 and flanges 102 and 103 of the device are substantially similar those described herein. Instead of the flow control elements described above (or in addition thereto) a tube-like member 700 is secured to the core segment 106. The tube member 700 is attached to the core segment 700 in a manner to allow the RA end of tube to extend into the RA in an axial direction, thus the tube's length must be sufficient to extend a distance into the RA. It has been found that the tube 700 configured in this manner prevents embolic particles from entering the tube and crossing over the septal divide into the LA. The distance that the tube 700 extends into the RA and beyond the plane of the RA-side flange opening (indicated by dotted line) should be at least a 1 mm but may be up to 2 cm in preferable embodiments. Even at relatively short lengths (such as where the tube extends only a few millimeters into the RA), the inventors have noted the surprisingly unexpected result of a reduction of embolic particles passing through. This is due to, in part, the tendency of embolic particles to collect along the surface of the septal wall and move toward the septal opening (or opening of an implanted device) with each cycle of the heart. By extending away from the septal wall 107, the tube provides an effective barrier to the embolic particles that would otherwise travel toward and possibly through the septal opening.

The present invention may include a percutaneously deliverable device. In some embodiments, the device has a straightened, elongated, low-profile delivery configuration suitable for delivery via a delivery system. The device may have a generally radially expanded and sometimes shortened deployed profile. For example, it can have a distal anchoring portion positioned on the left atrial side of the septum, a right anchoring portion positioned on the right atrial side of the septum, and/or a shunt portion, sometimes referred to as a "core segment", positioned through an aperture in the septum. The anchoring portions are sometimes referred to herein as "flanges". A flange may be annular flanges. An annular flange may comprise a plurality of segments. It is to be understood that in some embodiments having right and left anchors that the anchors may be connected and in some embodiments they are integrally connected.

In some embodiments, when a device according to the present invention is deployed across a patient's atrial septum, the distal and proximal flanges are located left and right to the septum respectively. The core segment of the device creates a shunt or passageway allowing blood flow across the aperture. Generally, the left atrium has a higher pressure than the right atrium and the blood tends to flow from the left atrium across the shunt to the right atrium. The greater the cross-sectional size of the core segment at any point in time, i.e., its shunting size, the greater amount of blood flows from the left to right atria. The greater the amount of blood flows to the right atrium, the greater the left heart decompresses. The left atrial pressure can be measured directly with a catheter in the left atrium or indirectly by measuring the pulmonary capillary wedge pressure (PCWP) during a right heart catheterization. The normal values of the mean left atrial pressure are typically in the range of 6-12 mmHg. The shunting size of the core segment of devices of the present invention may be tailored so that, during and post implantation, the left atrial pressure would reach the normal range of 6-12 mmHg. Thus for a DHF patient having a significantly elevated left atrial pressure, a device with a bigger shunting size should be used to restore the left atrial pressure to the normal range. For a DHF patient with a moderately elevated left atrial pressure, a device with a smaller shunting size should be used to restore the left atrial pressure.

The left atrial v-wave is the left atrial pressure at the end of an atrial diastole but immediately before the opening of the mitral valve. The left atrial v-wave represents the peak of the left atrial pressure. The size of the left atrial v-wave is determined partially by the amount of blood entering the left atrium. The normal range of left atrial v-wave is 6-21 mmHg. The shunting size of the core segment of the devices of the present invention may be tailored so that the left atrial v-wave would reach the normal range of 6-21 mmHg. Thus, for a DHF patient with significantly elevated left atrial v-waves, a device with a bigger shunting size can be used to restore the v-wave to the normal range. For a DHF patient with moderately elevated left atrial v-waves, a device with a smaller shunting size should be used to restore the v-wave to the normal range.

Systematic oxygen saturation is routinely monitored during a percutaneous implantation procedure. With the decompression of the left heart, the shunting size of the core segment of devices of the present invention may be tailored so that the systemic oxygen saturation level during and/or after an implantation procedure is maintained in the range of 75-100%. For a DHF patient with an elevated left atrial pressure, the higher the left atrial pressure elevation is prior to a treatment, the greater the shunting size should be used to maintain the systemic oxygen saturation level at a safe range; and the lower is the left atrial pressure elevation is prior to a treatment, the smaller the shunting size should be used to maintain the systemic oxygen saturation level at its safe range.

The ratio of pulmonary blood flow to systematic blood flow is defined as a Qp:Qs ratio. In a healthy heart, the Qp:Qs ratio is 1:1. In a DHF patient, Qp:Qs ratio is generally greater than 1:1. Some go beyond 2.5:1. The devices of the present invention be used to restore the Qp:Qs ratio to or close to the normal range. Thus, the left-to-right flow produced by the device may be tailored so that the Qp:Qs ratio would at some time reach the acceptable range of 1:1 to 1.5:1.

The greater the left-to-right shunting flow which is generated by the device, the lesser amount of blood remains inside the left atrium and, later, enters the left ventricle. The smaller is the shunting flow, the greater amount of blood remains inside the left atrium and, later, enters the left ventricle. The normal values of mean left ventricle pressure are typically in the range of 40-80 mmHg. Thus, the shunting size of the core segment of the device may be tailored so that the left ventricle pressure would reach the normal range of 40-80 mmHg. For a DHF patient with a significantly elevated left ventricle pressure, a device with a bigger shunting size may be used to restore the left ventricle pressure to the normal range. For a DHF patient with a moderately elevated left ventricle pressure, a device with a smaller shunting size may be used to restore the left ventricle pressure to the normal range.

With the left-to-right shunting flow created by the device, the amount of blood inside the right atrium increases, which results in an elevated right atrium pressure. The greater the left-to-right shunting flow is, the greater is the amount of the blood that remains inside the right atrium, and in turn, the greater is the elevation in the right atrial pressure. The smaller the left-to-right shunting flow is, the lesser is the amount of the blood that remains inside the right atrium, and in turn, the lesser is the elevation in the right atrial pressure. The normal values of the mean right atrial pressure are typically in the range of 4-12 mmHg. Thus, the shunting size of the core segment of the device may be tailored so that the right atrial pressure would remain the range of 4-12 mmHg. Thus for a DHF patient with the right atrial pressure in the lower range, such as in the range of 4-6 mmHg, a device with a bigger shunting size can be used, and for a DHF patient with the right atrial pressure within the higher range, such as in the range of 10-12 mmHg, a device with a smaller shunting size should be used to prevent right atrium overload.

With the left-to-right blood flow created by the device, the amount of blood inside the right atrium increases, and the amount of blood entering into the right ventricle increases, which results in an elevated right ventricle peak systolic pressure. The greater is the left-to-right shunt, the greater is the amount of blood remains inside the right atrium, and in turn the greater is the amount of blood enters into the right ventricle, and the greater is the elevation in the right ventricle peak systolic pressure. The lesser the left-to-right shunt, the lesser is the amount of blood remains inside the right atrium, and in turn the lesser is the amount of blood enters the right ventricle, the lesser is the elevation in the right ventricle peak systolic pressure. The normal values of the mean right ventricle peak systolic pressure are typically in the range of 20-40 mmHg. Thus, the core segment of the device may be tailored so that the right ventricle peak systolic pressure would not exceed the normal range of 20-40 mmHg. Thus for a DHF patient with the right ventricle peak systolic pressure within the lower range, such as in the range of 20-30 mmHg, a device with a bigger shunting size could be used; and for a DHF patient with the right ventricle peak systolic pressure within the higher range, such as in the range of 30-40 mmHg, a device with a bigger shunting size should be used in order to prevent right ventricle overload.

With the left-to-right blood flow created by the shunt device, the amount of blood remaining inside the right atrium increases, and in turn, the pressure difference between the right and left atrium decreases. The greater is the left-to-right shunt, the greater is the amount of blood remains insider the right atrium and the greater reduction in the pressure difference between the left and right atria. The smaller is the left-to-right shunting flow, the lesser amount of blood remains inside the right atrium and the lesser reduction is in the pressure difference between the left and right atria. The normal values for the pressure difference between the left and right atria are typically in the range of 2-10 mmHg. Thus, the shunting size of the core segment of the device may be tailored so that the pressure difference between the left and right atria would not exceed the range of 2-10 mmHg. Thus for a DHF patient with a pressure difference between the left and right within the lower range, such as in the range of 2-5 mmHg, a device with a bigger shunting size can be used. For a DHF patient with a pressure difference between the left and right atria within the higher range, such as in the range of 5-10 mmHg, a device with a smaller shunting size should be used in order to prevent right atrium overload.

Figure 31:
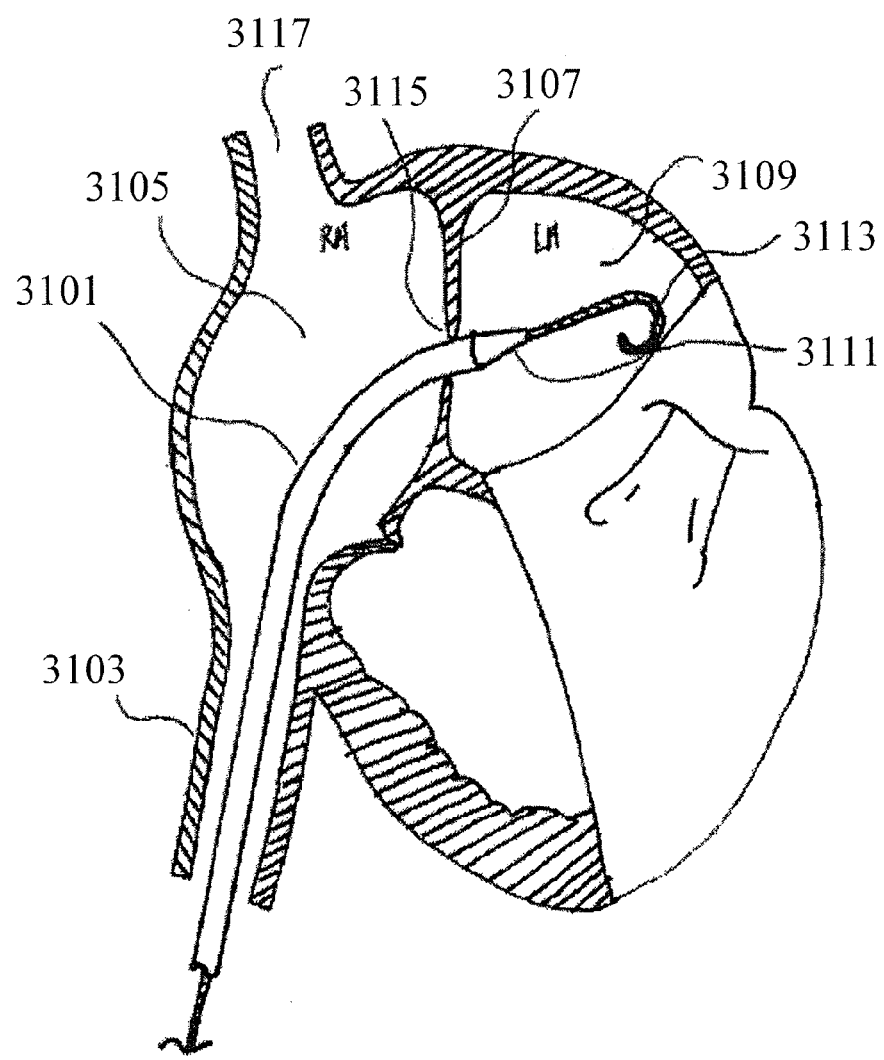
FIG. 31 is a partially cross-sectional view of a patient's heart in which a catheter is extending through the atrial septum.

FIG. 31 depicts a schematic view of a patient's heart and shows an example of a delivery catheter. An implant delivery catheter sheath 3101 is shown extending from the inferior vena cava (IVC) 3103, through the right atrium 3105, across the atrial septum 3107, and finally into the left atrium 3109. By convention the left atrium is depicted on the right side of FIG. 1, and the right atrium is depicted on the left side of FIG. 31. This convention will be used throughout this document. In essence, the heart of FIG. 31 represents a simplified view of a patient's heart. A conical dilating catheter 3111 extends from the distal end of the delivery sheath while a crossing wire 3113 further extends out of the dilating catheter. The implant delivery catheter is shown having crossed the atrial septum at the region of the fossa ovalis 3115, where the atrial septum is very thin.

The implant delivery catheter of FIG. 31 is configured to house an inventive device implant. The conical dilating catheter of FIG. 31 is configured to move axially within the implant delivery catheter, such that the conical surface may be initially used to dilate a small hole in the atrial septum and then may later be advanced or retracted in order to facilitate the deployment of the inventive device implant. The transition 3117 between the dilator and the sheath is carefully designed such that a very minimal step exists between the two components.

The crossing wire of FIG. 31 may be any suitably stiff wire currently available for catheter procedures, or it may be custom made for the procedure. The wire may include a sharpened tip in order to more easily perforate the septum. The wire may be made of stainless steel, Nitinol, or any other suitable material. After crossing the septum the wire may be withdrawn from the body, or may be left behind in order to facility the advancement of further devices and catheters into the body. In addition the wire may feature a curved distal section (as shown) in order to prevent the user from accidentally puncturing the wall of the left atrium. In embodiments of the present invention, the guide wire is a 0.9 mm (0.035") J-curve Nitinol wire. In other embodiments of the present invention the guide wire may be similar to the wires used in the treatment of total coronary occlusions. The design, manufacture, and use of guide wires for penetrating tissue are well known in the art.

The dilation catheter of FIG. 31 may be manufactured in a number of ways, and may be made of any suitable biocompatible material. A simple dilation catheter might be made from LDPE, HDPE, or FEP, and may feature a heat formed or over-molded conical tip. Another suitable dilation catheter construction might include a PEBAX or nylon braided shaft with a specially designed conical cap. The dilation catheter features a generally circular cross-section, however ridges or texturing may be employed in order to more efficiently dilate the septum by creating localized stress-concentration in the tissue near the ridges. In addition, the distal conical section of the dilator may incorporate a number of cutting features, such as a small metallic blades, or sharpened plastic protrusions, in order to more effectively dilate the atrial septum. In some embodiments of the present invention, the OD of the dilator is roughly between 3 mm and 5 mm.

Still referring to FIG. 31, the dilation catheter extends from an access point (not shown) in the lower veins, and extends into the right atrium through the inferior vena cava. In alternative embodiments of the present invention the dilation catheter may access the atrial septum by other means, including from the jugular vein (not shown) and through the superior vena cava 3119. In addition, access to the atrial septum may be provided by other means, including through minimally invasive surgery, and through other major vessels in the body.

Continuing to refer to FIG. 31, the delivery catheter may be configured such that in order to deploy an inventive device implant (not shown) the user may simply advance the catheter to the approximate position shown in the FIG. 31 and then retract the sheath relative to the dilator, thereby exposing the implant to the tissue. The dilator and guide wire may then be withdrawn from the atrial septum, leaving behind the therapeutic implant. Alternatively, the dilator may be withdrawn from the sheath and the sheath may then be used as a conduit for advancing a simple delivery catheter. The inventive device delivery catheter may be configured to carefully expand the left atrial side of the shunt in the left atrium with the sheath in place in the atrial septum. The sheath may then be withdrawn and the delivery catheter may be further configured to allow the right atrial side of the implant to expand in order to fully deploy the interatrial inventive device. The implant may be configured such that it is collapsed into a delivery configuration featuring a small delivery diameter and then naturally expands into the implanted configuration featuring a larger implanted diameter.

It is to be understood that the delivery catheter described with regard to FIG. 31 is only an example of a delivery catheter that can be used with the inventive devices. After extraction, the inventive device would be drawn into the catheter for removal. The inventive devices may also be used with other delivery catheters known in the art. Examples of delivery catheters are disclosed in U.S. Published Patent Application No. 2011/0295366 A1.

Figure 32:
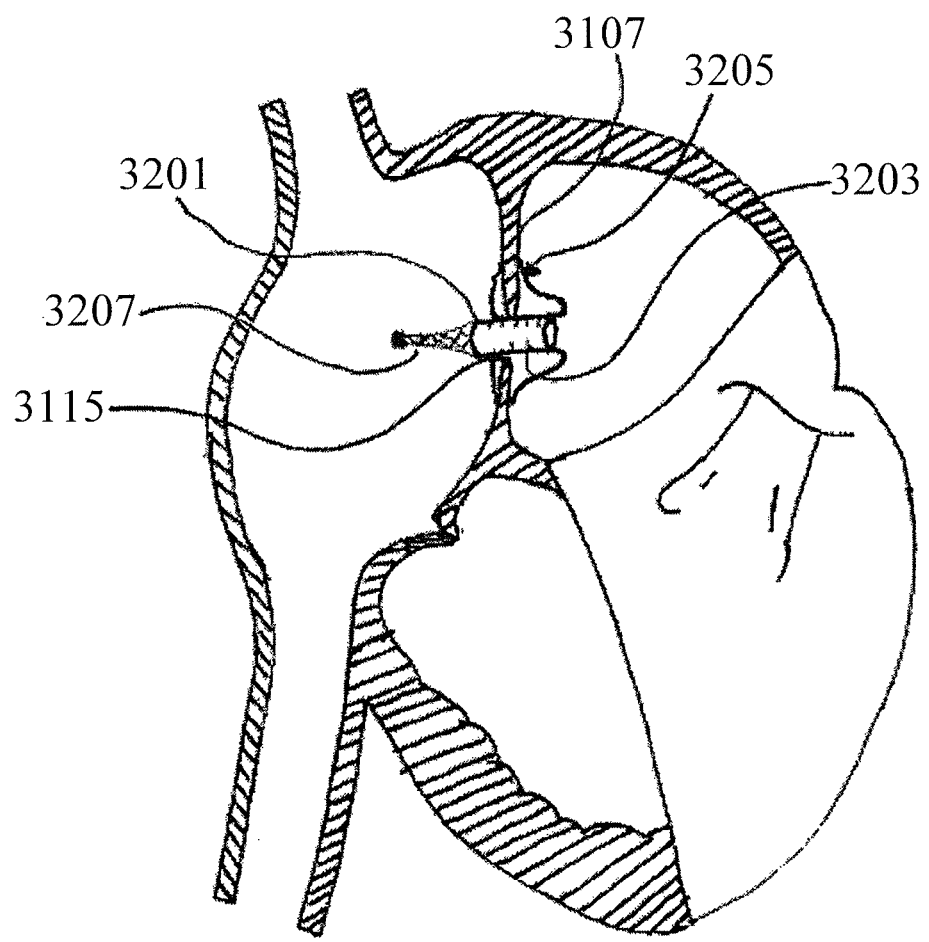
FIG. 32 is a partially cross-sectional view of a patient's heart in which an embodiment of an implantable device has been implanted within an aperture in the atrial septum.

Referring now to FIG. 32, an inter-atrial inventive device 3201 is depicted as implanted into the atrial septum 3107. The inventive device includes a tubular body 3203 and a series of anchoring elements 3205. The anchoring elements are designed to extend from the tubular body and engage the tissue of the atrial septum near the fossa ovalis 3115. A conical tail 3207 extends from one end of the shunt out into the right atrium. The conical tail has a very open mesh-like structure such that it does not impede blood flow through the shunt even though it connects to the tubular body circumferentially. The tubular shunt is configured to allow blood to flow through the internal diameter of the tubular body, thereby acting as a means to limit the pressure differential across the atrial septum.

Still referring to FIG. 32, the tubular body of the inventive device may be made of any suitable biocompatible implant material. The tubular body may include a stent-like skeleton, which may be collapsible to facilitate delivery of the device. The tubular body may further include an internal or external sheath in order prevent blood from flowing around the device instead of through the internal diameter of the shunt. The stent-like skeleton of the tubular body may be made of a laser-cut Nitinol tube, or may instead be made of woven Nitinol wire. The stent member may instead be made of stainless steel, MP35N, Cobalt-chromium, other shape-memory type alloys, other materials referred to as super-elastic alloys, or a plastic or polymeric material. Methods of manufacture of stents and stent-like implants are well established in the relevant prior art.

The conical tail of the interatrial shunt of FIG. 32 is configured such that it extends into the right atrium and therefore represents a feature which could be engaged by an appropriate retrieval catheter. The retrieval of the interatrial shunt is depicted in FIG. 33.

Figure 33:
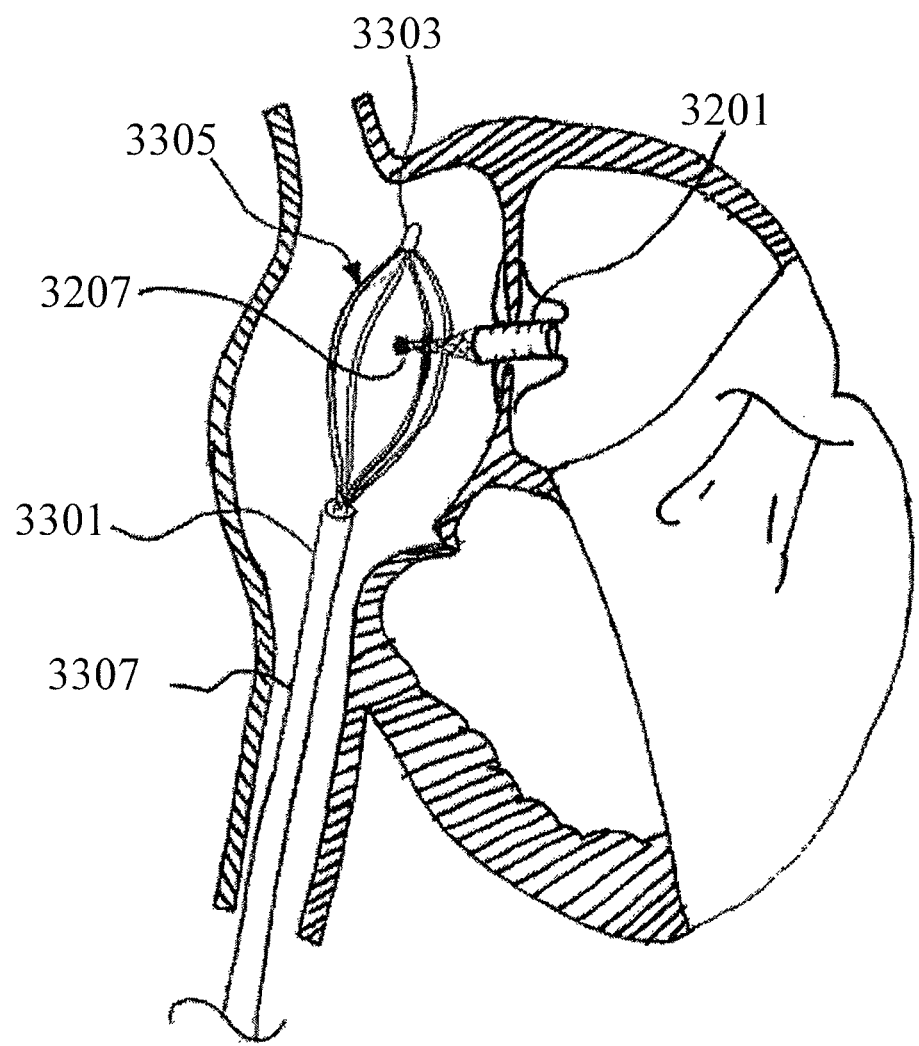
FIG. 33 is a partially cross-sectional view of a patient's heart as in FIG. 32 in which a catheter with a retrieval device is poised to engage the conical tail of the implantable device.

Referring now to FIG. 33 a snaring catheter 3301 is shown having been positioned near the conical tail 3207 of the interatrial inventive device 3201. The catheter consists of a radio-opaque tip 3303, a series of basket-wires 3305, and a delivery sheath 3307. The snare may be opened or closed by respectively retracting or advancing the delivery sheath. Advancing the delivery sheath over the basket-wires causes them to collapse into the sheath, while retracting the delivery sheath away from the basket-wires allows the wires to return to their open configuration. In this way a user is able to snare the conical tail of the inventive device by advancing the snaring catheter into the right atrium near the inventive device and retracting the delivery sheath exposing the basket-wires. The basket-wires would then expand in a way that makes entanglement with the conical tail very likely. The user may then re-advance the delivery sheath and capture the conical tail. The user may then withdraw the catheter from the body, in turn pulling the interatrial shunt out of the atrial septum. In this way the snaring catheter represents a retrieval catheter and may be used to remove an implanted interatrial shunt. Once this step is completed the user may then implant a new shunt of a larger or smaller internal diameter, or may instead replace the shunt with an occluding device, or may otherwise seal the hole in the septum. In this way the implant of FIG. 32 and the retrieval device of FIG. 33 represent a system for adjusting the inventive device in order to allow for the treatment of a progressing or otherwise changing disease state.

Figure 34:
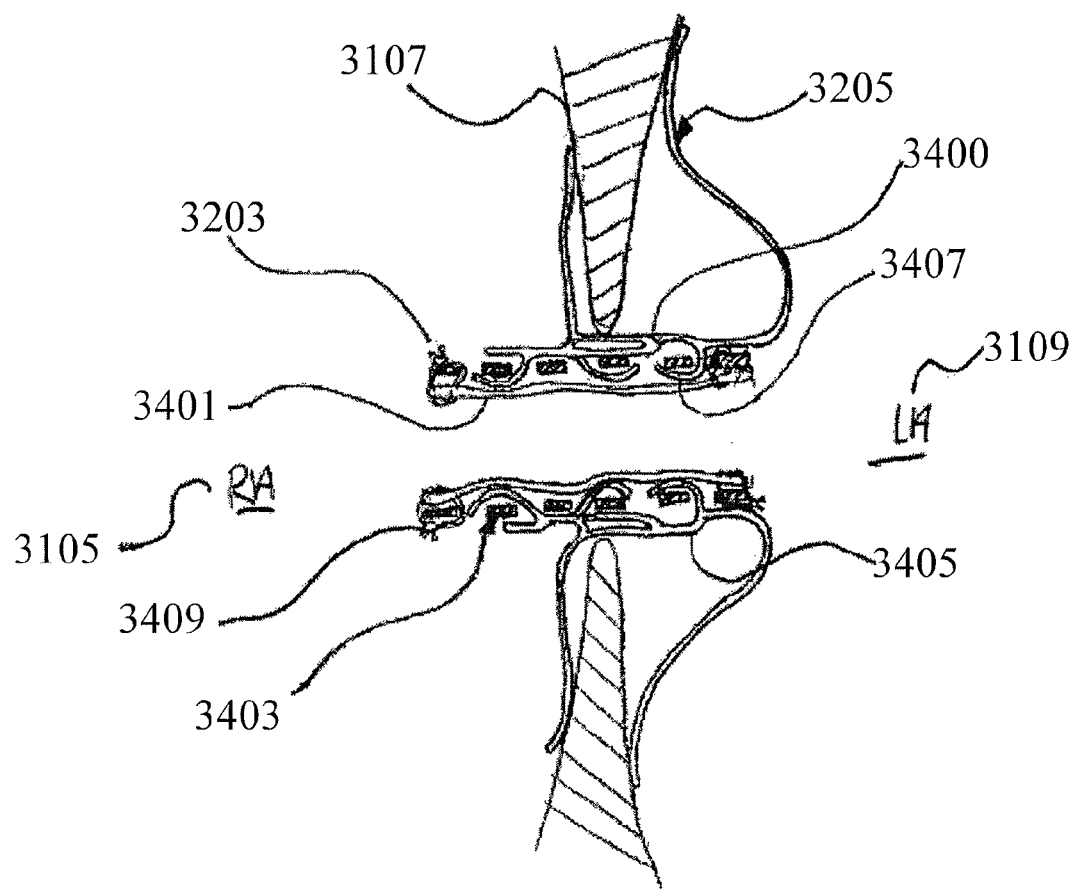
FIG. 34 is cross-sectional view of an embodiment of an implantable device which has been implanted within an aperture in the atrial septum.

FIG. 34 depicts a sectioned view of an embodiment of the present invention featuring an adjustable inventive device 3400 as implanted into an interatrial septum 3107. The inventive device of FIG. 34 includes an elongate tubular body 3203 and a series of anchoring members 3205. The elongate tubular body is constructed in roughly concentric layers. The inner most layer is an optional internal liner 3401 which directs the blood flow through the device from the left atrium 3109 into the right atrium 3105. The next layer is a stent like body 3403 which is manufactured of a plastically deformable material. This layer is represented in cross-section as a series of rectangular cross-hatched regions. The plastically deformable stent like member is constructed from a material such as stainless steel, and is designed such that when expanded, contracted, or otherwise deformed to a desired diameter it will naturally remain in the deformed state. The outer most layer of the tubular body of FIG. 34 is a super-elastic layer 3405 from which the anchoring members extend. The super-elastic layer has a number of hook features 3407 which couple the elastic layer to the plastically deformable layer. The super-elastic layer may be manufactured by laser-cutting a nitinol hypotube and then shape-setting the hooks and anchoring members into the desired shape. A series of knotted sutures 3409 are shown connecting the innermost layer, i.e., the internal liner 3401, and the plastically deformable layer, i.e., stent like body 3403; however the individual layers may be connected by any suitable means in order to form a cohesive tubular shunt body. It is to be understood that although for the sake of clarity the internal liner 3401 is shown as being attached only at its ends to the stent like body 3403, the internal liner 3401 may be attached at any and all points along its length to either the stent like body or the super-elastic layer 3405.

The layered construction of the tubular body of FIG. 34 allows for a user-adjustable shunt to be created. The user may adjust the size of the shunt by first engaging the shunt and then by deforming the plastically deformable layer as desired. The deformation is frozen in place by the plastically deformable layer. This deformation is then transferred to the super-elastic layer and the internal layer because the layers are interconnected and because the plastically deformable layer is stiffer than the other two layers. An example of such a manipulation is shown in FIG. 35.

Figure 35:
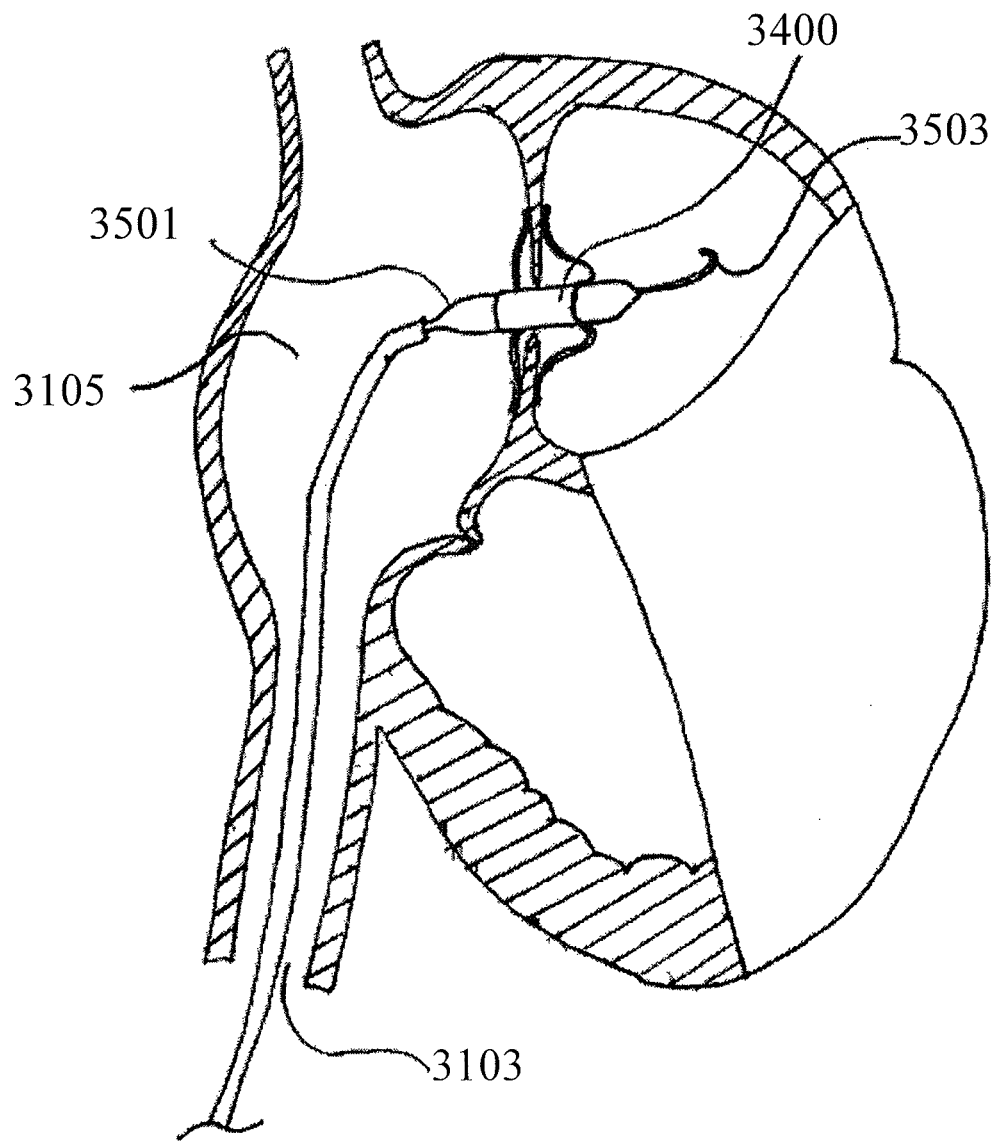
FIG. 35 is a partially cross-sectional view of a patient's heart as in FIG. 34 in which a catheter having a balloon extends through the implantable device.

Referring to FIG. 35, an adjustable pressure-relief shunt 3400 similar to that which is described above is shown. The pressure-relief shunt is being expanded by a balloon catheter 3501. The balloon catheter extends from the inferior vena cava 3103 into the right atrium 3105 and through the shunt. A guide wire 3503 extends from the balloon catheter and may be used to initially cross the shunt and then provide a rail for the dilation catheter placement. The balloon catheter may be inflated with a radio-opaque die in order to allow for precise control of the deformed diameter of the interatrial shunt. The dilation balloon may be a carefully sized non-complaint balloon. Alternatively, the dilation balloon may be a complaint balloon and the inflation pressure may be carefully controlled in order to achieve the desired shunt diameter. In some embodiments the adjustable inventive device is configured with an initial diameter around 3 to 4 mm and may be safely expanded up to 10 mm.

In embodiments the adjustment of the inventive device of FIG. 35 might begin with an echocardiography analysis of the blood flow through the shunt and an analysis of the patient's diastolic pressure, total cardiac output, pulmonary arterial pressure, and pulmonary venous pressures. If it is determined that the shunt should be adjusted the user might then carefully select the appropriately sized balloon. After gaining access to the vascular anatomy by conventional techniques a user may advance a guide wire into the right atrium and carefully direct the wire through the inventive device. The guide wire may then be used as a rail and the selected balloon may then be positioned inside the interatrial shunt. The balloon would then be carefully inflated until the desired diameter is achieved. The balloon is then deflated and withdrawn. The user may then repeat the analysis steps and further adjust the diameter of the shunt with additional balloon dilations if desired. In some embodiments of the present invention the initial diameter of the inventive device is configured to be very small such that the initial amount of blood flow through the valve is unlikely to cause rebound stress or shock. The user would then increase the diameter of the shunt as part of a routine follow-on procedure or as a delayed part of the initial implantation procedure.

The deformable and adjustable inventive devices of FIGS. 34 and 35 may be configured to be elastically adjusted by means other than a balloon catheter. For example, a inventive device may be designed such that the internal diameter of the shunt is adjusted by an axial compression or expansion. In other embodiments the shunt may be adjusted by a winding or unwinding action, or by a puckering, folding, or unfolding action.

Figure 36:
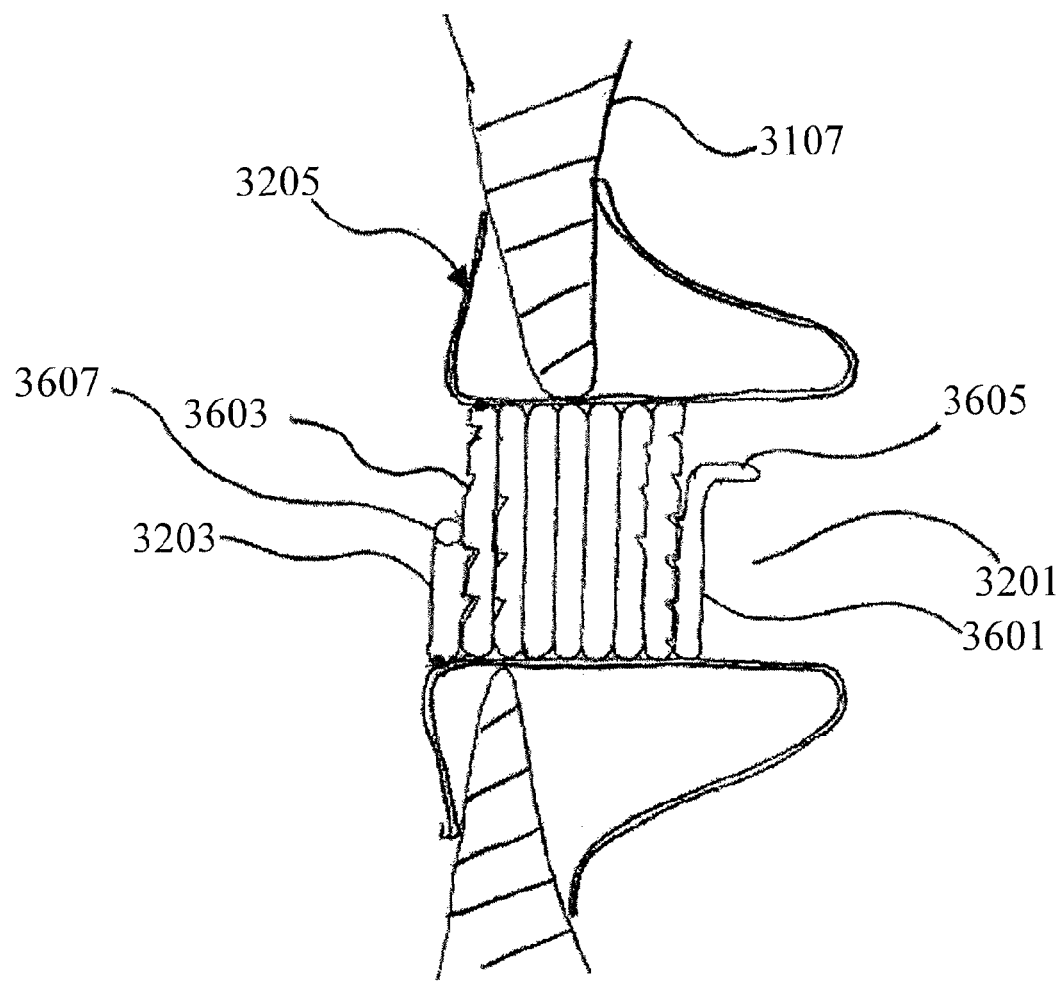
FIG. 36 is partially cross-sectional view of an embodiment of an implantable device which has been implanted within an aperture in the atrial septum.

Turning now to FIG. 36, a further embodiment of the present invention is depicted which may be adjusted in vivo from providing a first flow rate across a membrane of the patient's heart, e.g., the atrial septum, to having a second flow rate. The second flow rate may be selected as the result of evaluating the patient's heart condition at a time after the implantation of the device An interatrial shunt 3201 is shown as implanted into an atrial septum 3107. The interatrial shunt is comprised of a tubular body 3203 and a series of fastening members 3205. The tubular body of FIG. 36 is formed by a tightly wound coil 3601. The interface between the coils at either end of the tubular body features a series of one directional ramps 3603. On the left atrial side of the tightly wound coil is a left side adjustment tang 3605 and on the right atrial side of the tightly wound coil is a right side adjustment tang 3607. The adjustment tangs encroach into the internal diameter of the shunt in order to allow for the user to engage the adjustment tangs with an appropriate adjustment catheter.

The tightly wound coil 3601 of FIG. 36 may be made of any of the materials mentioned above, including nitinol, stainless steel, or a polymeric material. The fastening members 3205 may be connected to the coil at one end of the device such that the majority of the coils are able to be manipulated and repositioned relative to the tissue fastening members. Alternatively, the adjustment coil 3601 may be configured to rotate independently of the fastening members while simultaneously being axially constrained relative to the fastening members 3205. Finally, the fastening members 3205 may be connected to a separate tubular body which lies within and is constrained by the tightly wound coil 3601.

The tightly wound coil 3601 of FIG. 36 together with the one directional ramp features and the adjustment tangs 3605, 3607 allow the user to adjust the internal diameter of the shunt 3201 by winding or unwinding the coil. For example, the user may use an appropriate adjustment catheter to engage the adjustment tangs 3605, 3607 of the interatrial shunt 3201, and then apply torque to the right adjustment tang 3607 relative to the left adjustment tang 3605. The effect of this rotational adjustment would be to unwind the coil, 3601 which in turn opens the internal diameter of the interatrial shunt. The ramp features 3603 allow for the unwinding motion of the coils, but lock this motion in place, preventing the coils to return to their normal state. If the user wishes to reverse this operation the ramps 3603 may be circumvented by separating or stretching the coils axially, thereby over-riding the ramp features 3603. The number of turns of the coil 3601 is carefully configured such that the coil represents enough length such that it is longer than septum's thickness in order to shunt the blood from the left atrium to the right atrium. The number of coils is further configured such that a reasonable number of rotations are required to effect a preselected diametrical change in the shunt 3201. For example, the number of coils and the initial diameter of the shunt may be configured such that one 360 degree unwinding of the coils increases the diameter by 2 mm. The coil 3601 may be configured to create an adjustable inventive device with an internal diameter ranging from roughly 4 mm to 10 mm.

The interatrial shunt 3201 of FIG. 36 is configured to be implanted by an appropriate delivery catheter. The interatrial shunt is configured to collapse into the catheter either by increasing the number of winds and thereby decreasing the diameter, or by unwinding the coil 3601 and straightening the wire. The exact configuration of the interatrial shunt in its collapsed configuration depends on the material and design of the coil. For example, if the tightly wound coil is made of a super-elastic nitinol wire then the coil may be completely unwound and advanced through a catheter with a very small internal diameter. The super-elastic properties of the nitinol coil would allow the user to then advance the wire through the catheter, which would recover its initial coiled configuration upon exiting the catheter tip. For a stainless steel coil it would be more appropriate for the coil to be delivered in a first collapsed diameter. The user would then deliver the interatrial shunt by implanting it into the tissue and then deforming the stainless steel coil with an unwinding motion until the implant reaches a larger second diameter.

The adjustment tangs 3605, 3607 of FIG. 36 are configured to be engaged or disengaged in vivo in a repeatable manner by an adjustment catheter. The adjustment catheter includes an inner and an outer shaft, each of which is configured to transmit torque relative to the other. For example, the adjustment catheter may include a braided outer catheter shaft and a tri-filar inner catheter torque transmitting shaft. Alternatively the adjustment catheter may include a laser cut hypotube which is designed to transmit torque. The engagement of the catheter with the adjustment tangs may be assisted by the use of radio-opaque markers incorporated within the shunt near the adjustment tangs. The adjustment catheter inner and outer shaft may each feature a slot for engaging with the adjustment tangs. The slots include a generous lead-in in order to help position the catheter. The slots may be tapered to lock the tangs into the adjustment catheter. The adjustment catheter may include an expandable basket or expandable support wires in order to center the catheter within the interatrial shunt. Alternatively the adjustment catheter may incorporate a snaring mechanism to ensnare the adjustment tangs. The inner and outer adjustment catheter shafts may then interact with the snaring features in order to engage the adjustment tangs. Finally, a series of adjustment tangs may be used to create a shape that can be keyed off of by a catheter. For example, the left side of the coil may feature three adjustment tangs which create a clover shaped internal profile in the inventive device. This profile may then be easily engaged by an appropriately shaped adjustment catheter.

In use a physician would advance the adjustment catheter into the internal diameter of the interatrial shunt. The adjustment catheter may be tracked over a wire which has been placed through the shunt and into the left atrium. The left side and right side adjustment tangs 3605, 3607 would then be engaged by the adjustment catheter using any of the above described engagement methods, including simply keying the tangs into a pair of slots. The left side adjustment tang 3605 would be keyed into the inner shaft of the adjustment catheter while the right side adjustment tang 3607 would be keyed into the outer shaft of the adjustment catheter. The left side adjustment tang 3605 may be held stationary by the inner adjustment catheter shaft, while the outer adjustment catheter shaft would then be rotated by the user in the appropriate direction to unwind the coil 3601 and increase the inner diameter of the shunt. Alternatively, the right side adjustment tang 3607 may be held stationary by the outer adjustment catheter shaft while the left side adjustment tang 3605 is rotated by the inner adjustment catheter shaft. In either case, the fastening features of the inventive device would be connected to the side of the shunt that is held stationary relative to the body. In this way the shunt is not simply rotated within the interatrial septum. In some embodiments the user may be able to reset the coil back to its initial configuration by axially stretching the tightly wound coil and thereby disengaging the one-directional ramps 3603 and allowing the coil to wind or unwind as needed.

The adjustable interatrial inventive device of FIG. 36 may be modified to allow for reducing the internal diameter of the inventive device with the adjustment catheter. This may be accomplished by simply reversing the directions of the one-direction ramps 3603, such that a winding motion instead of an unwinding motion may be locked in by the one-directional ramps. In this case the shunt may be deployed in a collapsed delivery diameter and then expanded to a first implanted diameter by the user. The user may then decrease the size of the interatrial shunt by winding the coil 3601 in a similar manner to that described above. Once again, the user may be able to reset the interatrial shunt to the initial deployed diameter by axially stretching the coils to over-ride the one-directional ramps.

Figure 37:
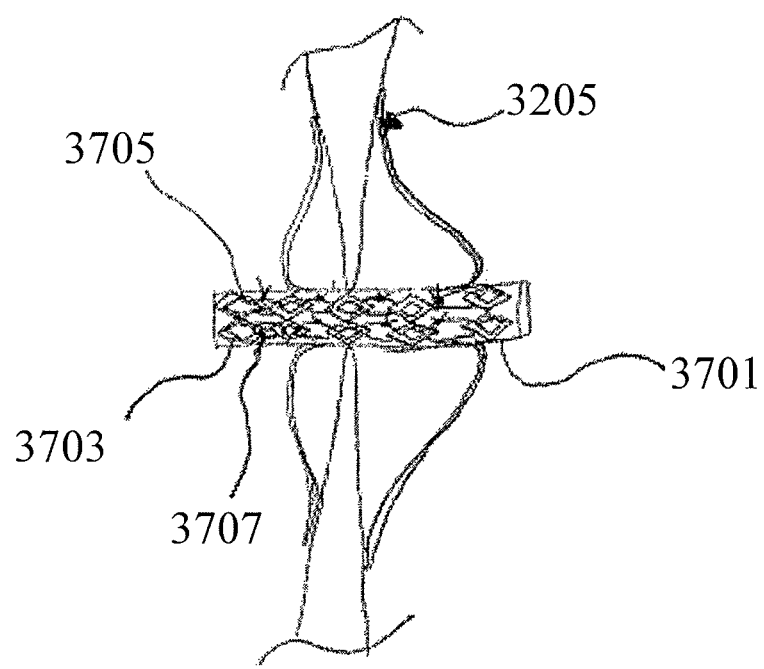
FIG. 37 is partially cross-sectional view of an embodiment of an implantable device which has been implanted within an aperture in the atrial septum.
Figure 38A:
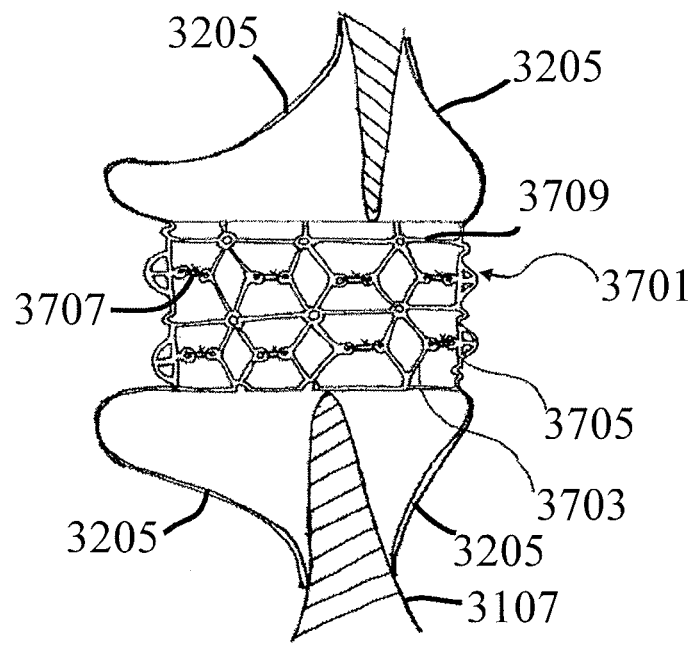
FIG. 38A is a partially cross-section view of an embodiment of an implantable device which is similar to that shown in FIG. 37, except for the alteration to its diamond shaped struts.
Figure 38B:
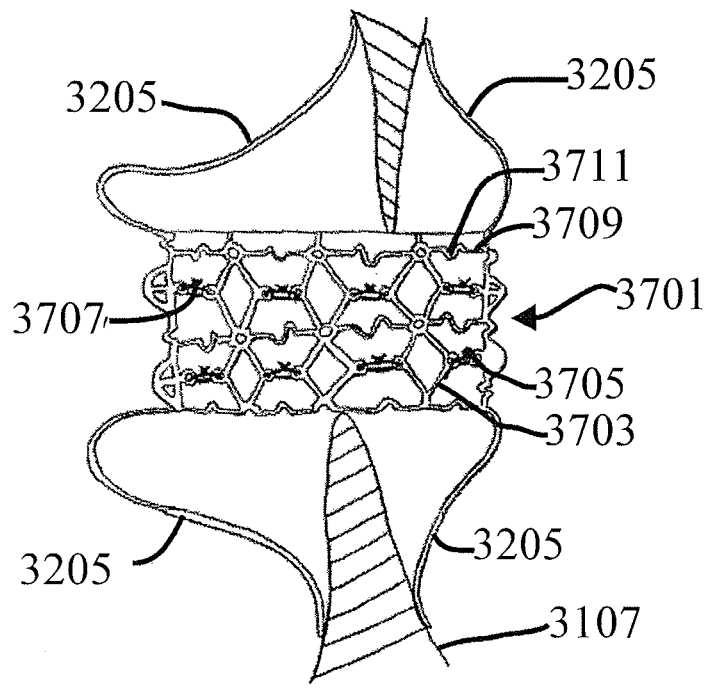
FIG. 38B is a partially cross-section view of an embodiment of an implantable device which is similar to that shown in FIG. 38A, except for the alteration to its axially stiff members.

Turning now to FIGS. 37-38B, alternative interatrial shunts are depicted. The inventive devices illustrated in these drawings are the same as each other except as noted below. The interatrial shunt of FIG. 37 includes a stent-like elongate tubular body 3701 and a series of anchoring members 3205. The stent-like frame of the tubular body includes a series of diamond shaped struts 3703. Each diamond shaped strut features a pair laser cut eye-holes 3705. The diamond shaped struts and eye-holes are spaced around the circumference and the length of the stent-like frame. Bio-resorbable suture material 3707 is shown tied between various pairs of eye-holes. The suture materials are tied such that the stent is held in an elongated state by the presence of the suture, as the diamond shaped struts are held stretched out axially. The stent frame is therefore shown in an elongated state in FIG. 37. The suture material is designed to be slowly absorbed by the body over time, which in turn allows the diamonds struts to return to their relaxed configuration. The relaxed diamond struts in turn exert a radially outward force, causing the stent member to expand radially as the suture material is absorbed into the body. In this way the inventive device of FIG. 37 represents a means for automatically and gradually changing the amount of blood flow through an inventive device in order to provide a non-static treatment for diastolic dysfunction.

The stent-like frame of may be made from a laser cut nitinol hypotube in a manner that is very similar to the manufacture of many stents. The laser cut nitinol hypotube may then be heat set to a predetermined final diameter. The heat set stent frame may then be stretch axially and then the suture knots tied around the eye-holes of the stent frame. The stent frame features sets off axially stiff members 3709 (identified in FIG. 38A) between the various diamond-shaped struts. The axially stiff members are configured to help maintain the integrity of the stent frame such that the force required to stretch the diamond struts axially does not simply collapse the stent frame between the struts. The initial diameter of the stent frame may be configured such that the inventive device allows only a small amount of blood to flow through the shunt. Furthermore, the number, size, and shape of the diamond struts may be carefully selected such that the final diameter of the shunt after the loss of the suture loops reaches a size that allows sufficient blood flow through the shunt to treat the majority of the patient population. Still further, the amount that the diamond shaped struts are stretched may be configured such that a predetermined amount of mechanical advantage is built into the expanding action of the stent frame.

The bio-resorbable sutures of the devices of FIGS. 37-38B may be made from any number of known absorbable suture fibers, including polyglycolic acid, polylactic acid, polydioxanone, or polycaprolactone. The manufacture of bio-resorbable sutures is well known in the art. Absorbable sutures of various sizes may be used to delay or stagger the effect of the expanding action of the inventive device. Bio-absorable sutures may have a diameter ranging from 0.1 mm to 0.7 mm (USP sizes 6-0 to #3 respectively). In addition, the bio-resorbable sutures may be a monofilament construction, or may be braided. The bio-resorbable substrate may instead include a suture-like structure of any cross-sectional geometry, including a film-like structure, a thin tape-like structure, or a rectangular or triangular cross-section. As an example, initially a rapid expansion may be desired and so very thin sutures are used at strategic locations to allow for the initial expansion of the shunt. Subsequently, a much slower expansion may be desired, and this secondary expansion phase may be accomplished by using a much thicker suture material on a second set of expansion struts. The inventive device may be configured to expand gradually from roughly 4 mm to roughly 10 mm over the course of a number of days, weeks, or months.

FIG. 38A shows a more detailed view of the inventive device described with regard to FIG. 37. The action of the eye-holes 3705 and the diamond shaped struts 3703 can be more clearly seen in FIG. 38A, although the mechanisms are the same as described above. The inventive device of FIG. 38A is shown with a lesser expansion ratio than that of FIG. 37, as the diamond struts are stretched less such that when the sutures are absorbed into the body the shunt will expand less. This may be desirable for patients with toughened septal tissue, as the lesser expansion allows for the use of stiffer diamond struts which are capable of exerting a larger outward radial force. The bio-resorbable suture material may be made from any of the above mentioned materials and may include any of the above mentioned configurations. In addition, the bio-resorbable sutures may be replaced by any other suitable bio-resorbable substrate, including a sheet of bio-resorbable material, a bio-resorbable mesh, or a bio-resorbable film.

Upon sufficient dissolution of the bio-resorbable restraints, the device shown in FIGS. 37 and 38A will bulge radially outward to assume a barrel shape thereby increasing the hydraulic diameter of the device so as to increase the flow rate therethrough. A variation of the device of FIGS. 37 and 38A is shown in FIG. 38B. The device of FIG. 38B is similar in all respects to that of FIGS. 37 and 38A except that it contains expandable sections 3711 along its axial stiff members 3709. Upon sufficient dissolution of the bio-resorbable restraints, the expandable sections 3711 cause an increase in the longitudinal length of the body 3701 and a corresponding contraction of its diameter, thus decreasing its hydraulic diameter and the flow rate therethrough.

Figure 39:
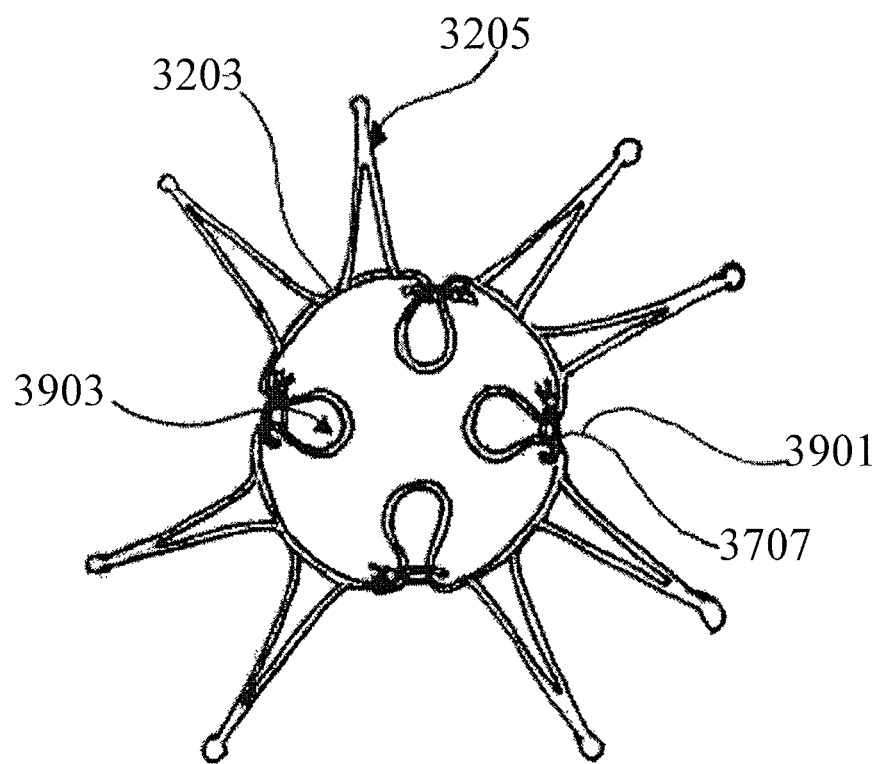
FIG. 39 is an end view of an embodiment of an implantable device.

Turning now to FIG. 39, an inventive device 3901 is shown as viewed from the central axis of the shunt. The inventive device consists of a tubular body 3203 and a series of anchoring members 3205 which extend radially outward from the shunt body. The anchoring members again are used to anchor the inventive device to the septum. The tubular body is made of a stent-like frame. An optional internal liner (not shown) may be used to ensure that blood flows through the shunt from the left atrium and into the right atrium instead of through the side wall of the tubular body. The tubular body of the shunt is periodically broken into by a series of inward folds 3903 of the tubular body. The inward folds are held in place by bio-resorbable sutures 3707 similar to those used in previous embodiments. The inward folds are configured to take up space inside the shunt, and thereby limit the amount of blood flow through the shunt. As the sutures are absorbed into the body the folds are configured to gradually straighten out, and the inventive device is thereby expanded. The expansion by loss of the inward folding is caused both by the direct expansion of the inventive device as well as by the fact that the folds impede blood flow and as they disappear the blood is able to flow through the shunt more efficiently.

Referring now to FIGS. 40A-40D an embodiment of the interatrial inventive device is depicted as it gradually transforms over time. The interatrial shunt of FIGS. 40A through 40D is designed to be implanted with a first effective internal diameter. The shunt is then configured to gradually expand over time to a second, substantially larger effective internal diameter. Finally, after a longer but still predetermined amount of time the inventive device of FIGS. 40A-40D is configured to contract to a third effective internal diameter which is substantially smaller than the second effective internal diameter. It is to be noted that the intra-atrial shunt may be configured to adjust to an multitude of progressively larger or smaller diameters, and thus is not limited to the three progressively larger diameters described in connection with FIGS. 40A-D.

Figure 40A:
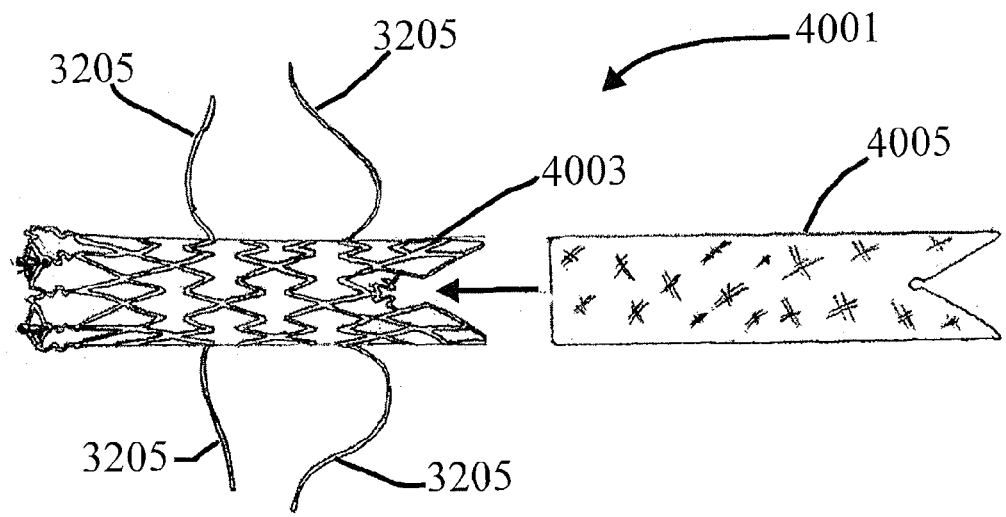
FIG. 40A is an exploded side view of an embodiment of an implantable device.
Figure 40B:
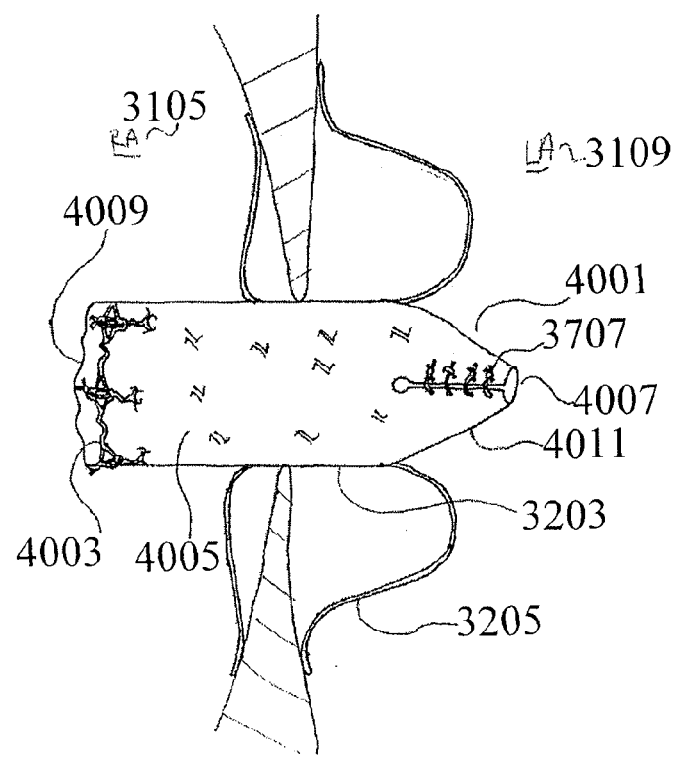
FIG. 40B is partially cross-sectional view of the embodiment of FIG. 40A which has been implanted within an aperture in the atrial septum showing the implantable device just after implantation. Only a small portion of the frame of the device is shown in this drawing.
Figure 40C:
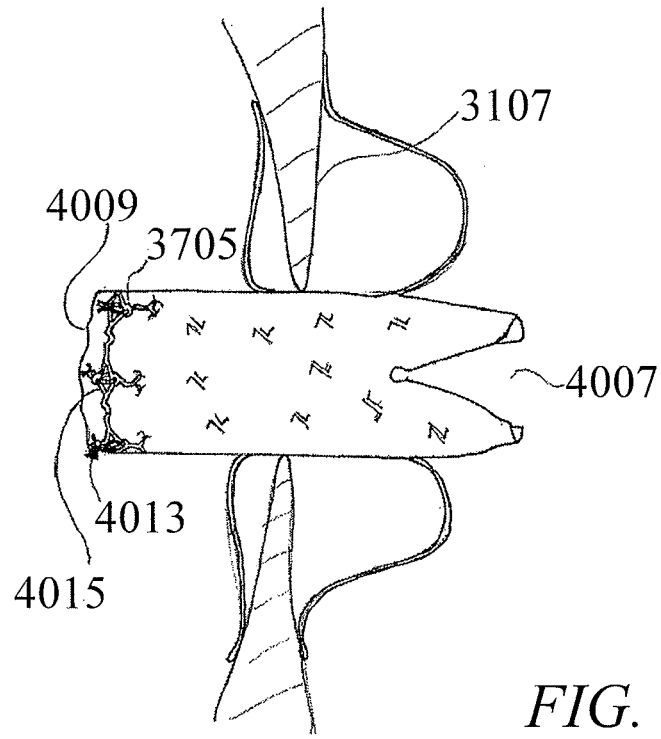
FIG. 40C is a partially cross-sectional view as in FIG. 40A but showing the implantable device at a later time after the absorption of the biosorbable material which at one end of the device. Only a small portion of the frame of the device is shown in this drawing.

FIGS. 40A-D depict another embodiment of inventive device. FIG. 40A shows an exploded side view of interatrial inventive device 4001. The stent-like frame 4003 is shown about to receive the internal sheath 4005 to which it will be subsequently attached. For clarity sake, only a small portion of the frame 4003 is shown in FIGS. 40B-40C.

Referring now to FIG. 40B, an interatrial inventive device 4001 is depicted. The inventive device includes an elongate tubular body 3203 and a series of anchoring members 3205. The elongate tubular body includes a stent-like frame 4003 and an internal sheath 4005. The stent-like frame is once again constructed from a super-elastic material, such as nitinol. The stent-like frame includes a left end 4007 and a right end 4009, the left end points into the left atrium 3109 and the right end protrudes into the right atrium 3105. The left end is designed with a conical opening 4011. The conical opening is manufactured by creating a wedge shaped cut out of the tubular frame and folding the frame such that the cut edges are adjacent to each other. The left end of the frame is cut such that the opening is fully open in the relaxed configuration, but has been compressed and sewed as pictured with bio-resorbable sutures 3707. The bio-resorbable sutures of the left end are configured to be absorbed by the body over a predetermined period of time. For example, in some embodiments the sutures are designed to be absorbed in 10 to 30 days' time. As the sutures dissolve into the body the left end opening is configured to gradually expand, such that the amount of blood flow through the device gradually increases. As the last suture is absorbed into the body the interatrial shunt reaches its maximum diameter. The maximum diameter of the interatrial shunt is carefully configured in order to allow for a therapeutic amount of blood to flow through the device. In some embodiments this maximum diameter may be between 6 mm and 10 mm.

Referring now to FIG. 40C, where the interatrial inventive device of FIG. 40B still with a left end 4007 and a right end 4009 is depicted as implanted into the atrial septum 3107. The left end bio-resorbable sutures have dispersed into the body and the internal diameter has reached its peak size. The inventive device is configured to remain at this configuration for a predetermined amount of time. The duration of the shunt remaining at its maximum effective internal diameter is controlled by the right end bio-resorbable substrate. The right end is cut or shape set in a normally closed configuration. The shunt is then expanded and the expansion is locked in place by the bio-resorbable substrate. As shown in FIG. 40C, the bio-resorbable substrate may be a series of bio-resorbable sutures 4013. The sutures are able to hold the right end of the interatrial shunt open due to the structure of the right end stent-like frame, which features a series of diamond shaped struts 4015, similar to those depicted in FIG. 37. The diamond shaped struts are designed such that the major axis of the diamond points along the axis of the device and is much longer than the minor axis of the diamond. On either end of the major axis of the diamond shaped struts are eye-holes 3705, through which sutures may be tied. A suture is tied between the two eye holes on the diamond shaped struts and the major axis of the diamond is compressed. This in turn causes the minor axis to expand, with the net result being the expansion of the circumference of the shunt which finally leads to the expansion of the overall diameter of the shunt. The amount of expansion may be controlled by the length of the suture knot, the shape of the struts, or the number of diamond struts that wrap around the circumference of the inventive device. The right sided bio-resorbable sutures are configured to take a much longer time to absorb into the body than the left side sutures. For example, the right side sutures may be made of a USP size #1 suture while the left side bio-resorbable suture may be a USP size 4-0 suture or smaller.

Figure 40D:
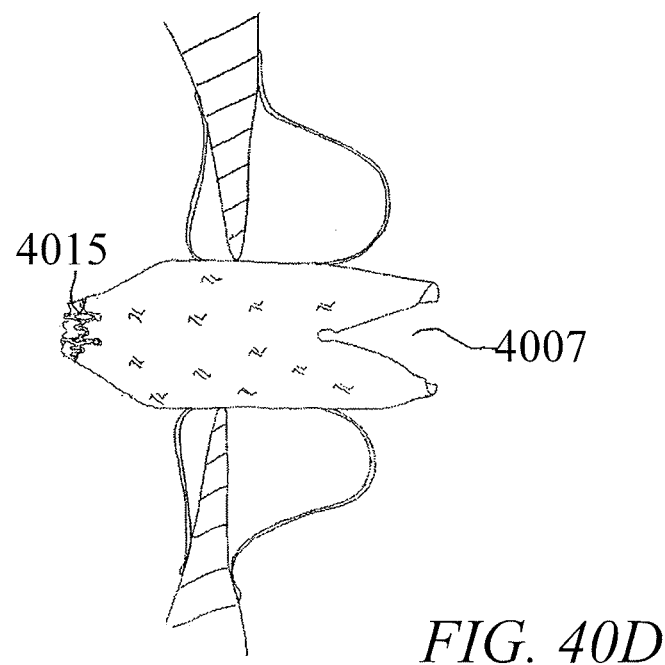
FIG. 40D is a partially cross-sectional view as in FIG. 40C but showing the implantable device at a still later time after the absorption of the biosorbable material at the other end of the device. Only a small portion of the frame of the device is shown in this drawing.

Turning now to FIG. 40D, the interatrial inventive device of FIGS. 40B and 40C is depicted in its final configuration, where the left side 4007 has opened up fully, and much later the right side 4009 has closed fully. The diamond shaped struts 4015 are shown in the relaxed configuration and the right side is overall at its lowest energy state. The size of the final right side orifice may be configured such that a minimum amount of blood is allowed to flow through the device such that some therapeutic treatment may be expected of the shunt without the risk of the adverse events of associated with significant long term left to right shunting of blood. In this way FIGS. 40A-D represent a means for treating diastolic heart failure dynamically.

Figure 41:
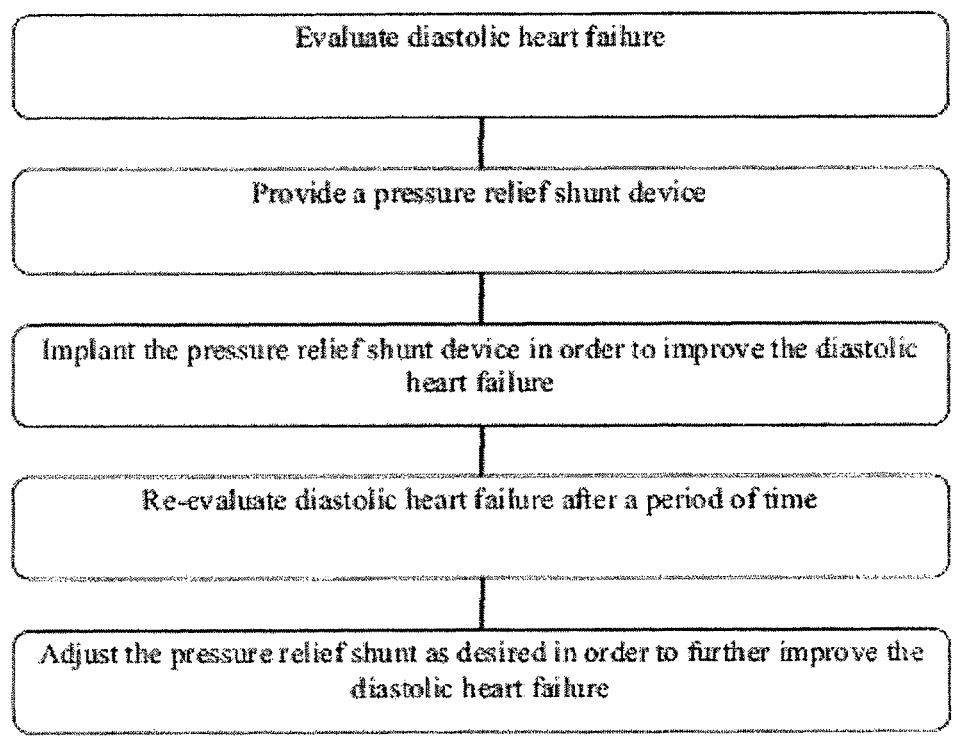
FIG. 41 is a flow diagram of a method embodiment.

Turning now to FIG. 41, a method for treating diastolic heart failure is outlined. The method includes first analyzing or characterizing the patient's diastolic dysfunction through means that are well described in the art, including trans-esophageal echocardiography, trans-thoracic echocardiography, MRI, CT, or catheterization. The method further includes using the data gained from the analysis to select a inventive device to be implanted into the interatrial septum with a preselected internal diameter. The inventive device may be any of the adjustable inventive devices described herein or any of their equivalents. The inventive device is configured to allow an amount of blood flow through the shunt that is determined by the analysis to be unlikely to cause any short term shock or pressure spikes for the patient. The method then includes a waiting period where the patient's heart is given time to gradually adjust to the newly improved hemodynamic conditions. Next a second series of analysis is then carried out, using similar methodologies to those described above. The second analysis is used to determine whether additional adjustment of the shunt would be beneficial for the patient. If the adjustment is thought to be beneficial based on the analysis then the method includes using an appropriate adjustment catheter or adjustment balloon catheter to adjust the inventive device and thereby change the amount of blood flow through the shunt in order to benefit the patient. The adjustment may include increasing the internal diameter of the inventive device in order to allow additional blood flow through the device or it may instead include decreasing the diameter of the shunt in order to prevent complications such as the development of hypertrophic pulmonary arteries. In this way the method outlined in FIG. 41 represents a method for treating diastolic heart failure in a dynamic and adjustable manner.

While the foregoing description focused on embodiments that automatically adjust the flow rate through the shunt, the present invention also includes embodiments which the flow rate adjustment is made manually or a combination of manually and automatically. Some embodiments which may include automatic, manual, or a combination of automatic and manual rate adjustments are described below.

Figure 42:
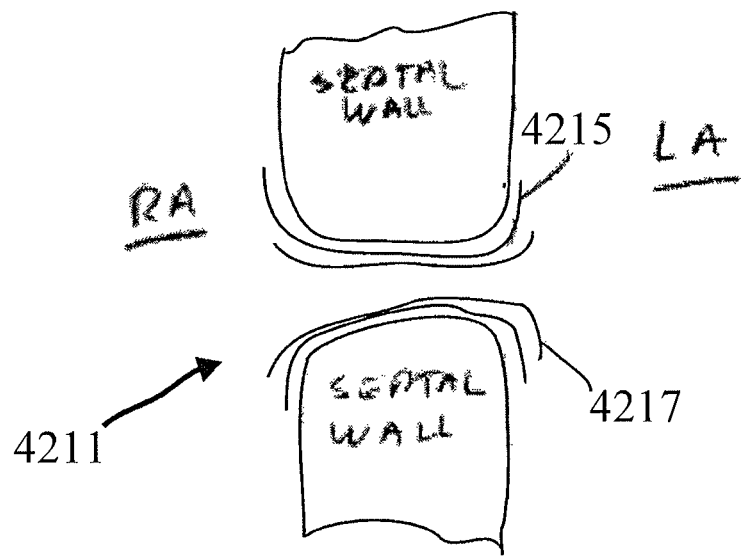
FIG. 42 is a cross-sectional view of an embodiment of an implantable device after implantation in an aperture of an atrial septum.

This disclosure concerns an adjustable shunt for allowing flow from an area of high pressure, such as a left atrium of a heart, to an area of lower pressure, such as a right atrium of a heart. As explained above, this device may help to relieve over-pressure and may aid in preventing hypertrophy in the affected blood vessels. FIG. 42 discloses a cross-section of a multi-part intra-atrial shunt 4211 placed into a septum and held in place by the septal wall of a person's heart. The shunt 4211 includes two parts, a retaining cage 4215 directly attached to the septal wall, and an insert 4217 attached to the cage 4215 and retained in place by the cage.

In this embodiment, the shunt 4211 may be relatively symmetrical, i.e., the portion of the shunt retained in the left atrium is substantially similar to the portion of the shunt retained in the right atrium. In addition, the tubular central portion may be relatively uniform along its length.

Figure 43:
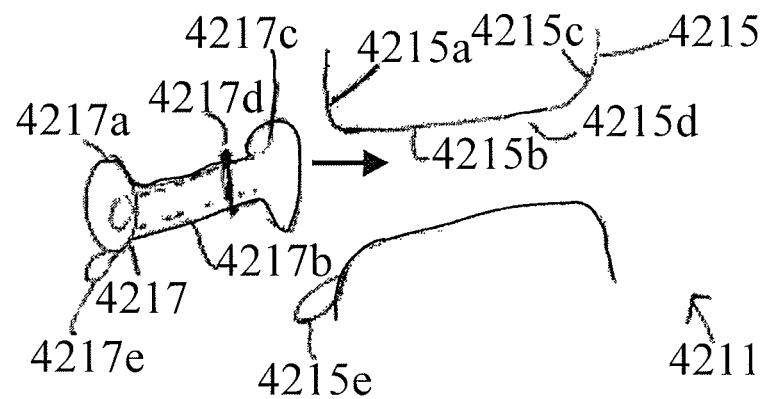
FIG. 43 is a partially exploded view of the inventive device of FIG. 31

A closer and more detailed view of a shunt embodiment is disclosed in FIG. 43. In this embodiment, the shunt 4211 includes cage 4215 and insert 4217, the cage and the insert also including retaining features that allow the insert to reversibly lock into the retaining cage. Cage 4215 includes a right atrium flange 4215a which is substantially similar to left atrium flange 4215c. The intermediate portion 4215b is substantially tubular, with a retention feature 4215d, which may be a void or a space, i.e., an indentation or some other receptacle, available on the outer surface of the cage. Cage 4215 may be made of struts and apices of nitinol, the nitinol having a martensite/austenite transition below 37° C., preferably in the neighbourhood of about 25° C., so that the cage remains in its superelastic, austenitic phase during use inside a body of a human or a mammal.

The other portion of the adjustable shunt is the insert 4217, which may be impermeable and may allow flow of blood or other fluid only through its central passage. Insert 4217 includes an outlet 4217a and an inlet 4217c that is substantially similar to the outlet. The central portion 4217b is generally tubular and not permeable to fluids, with an outer surface having a retention feature 4217d for matching with the retention feature 4215d of cage 4215. Insert 4217 may be formed from a polymer such as PTFE, UHMWPE, HDPE, polypropylene, polysulfone, or other biocompatible plastic.

Retention feature 4217d may be a tab or a button for placing into a void or space of cage 4215. It will be understood by those having skill in the art that the inner diameter or dimension of insert 4217 determines blood flow from the higher pressure left atrium to the lower pressure right atrium of the patient into whom the shunt is implanted. It will also be understood that the cage 4215 will be implanted first with the insert 4217 later implanted into the cage. Both the cage and the insert have a removal feature 4215e, 4217e, such as a loop of suture or of a radiopaque material included into the retrieval loop. Examples of radiopaque materials may include a gold or platinum thread. A retrieval device, such as a snare or grasper, may be used to grasp the retrieval loop for removal from the patient or re-placement within the patient.

The retention feature is important because the insert will only control the flow of blood from an area of higher pressure to an area of lower pressure in the heart if it is retained in place. The retention feature is also important because it is this feature that allows the purposeful or intentional removal of the insert, so that the insert can be replaced with an insert of a lesser or greater diameter, depending on whether a lesser or greater amount of pressure relief is required for the patient. As noted above, the amount of relief, that is, the radius or hydraulic radius of the opening, may vary among patients and may vary in time for a given patient. Thus, a multi-part shunt, with inserts of different effective hydraulic diameters, may be used to allow relief to a patient. To be clear, it is to be understood that a multi-part shunt may include a plurality of inserts and one insert may be replaced by another in vivo as need be to achieve the desired flow rate for the patient. It is clearly a less traumatic surgical procedure to replace the insert described here than to implant the entire shunt, and in particular, to implant the cage. Once the cage has been implanted, subsequent procedures are accomplished more quickly and with less trouble to the patient. The inserts, for example, may have inner diameters from 0 to 15 mm, including inserts having inner diameters from 3 to 5 mm. This is the diameter of the flow path from a higher pressure area to a lower pressure area.

Figure 44:
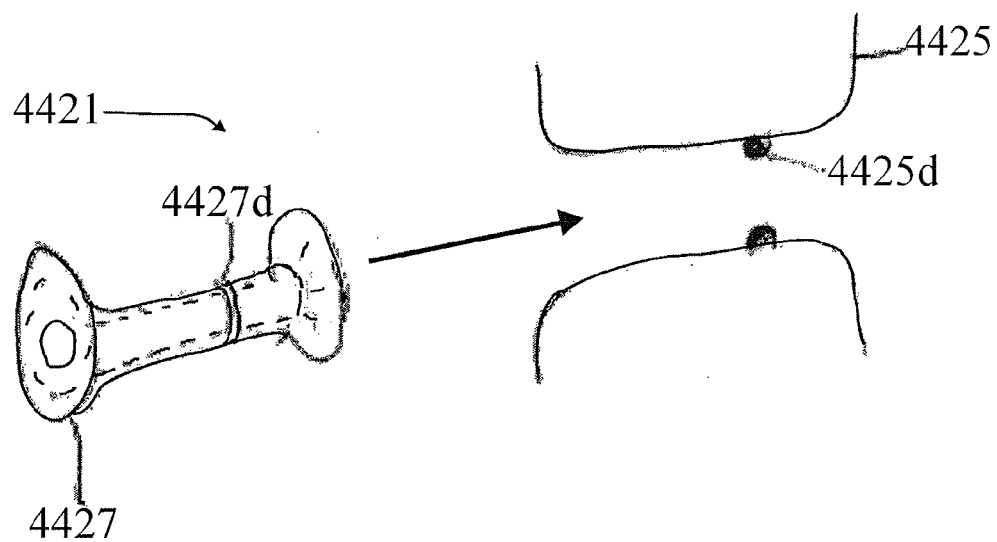
FIG. 44 is a partially exploded view of another embodiment of an implantable device.

Another embodiment is depicted in FIG. 44. In this embodiment, adjustable intra-atrial shunt 4421 includes a cage 4425 with a positive or protruding retention feature 4425d, such as protruding tab or ridge on its inner side. Insert 4427 includes a groove 4427d to receive the protruding rib or ridge from the cage 4425. Thus, the insert is retained within the cage.

Figure 45:
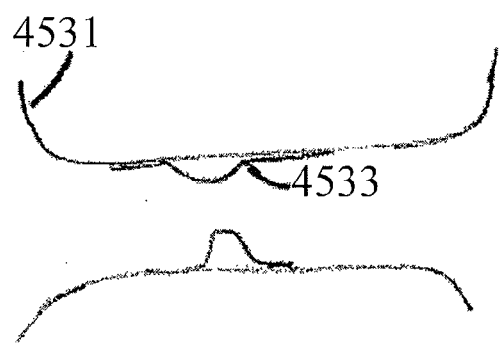
FIG. 45 is a cross-sectional view of the insert portion of an embodiment of an implantable device.

In another embodiment depicted in FIG. 45, insert 4531 includes an inner portion of reduced diameter 4533, the portion with reduced inner diameter molded to that shape or produced by one or more secondary operations. Using this technique, a single insert shell or form may be used and then adapted or adjusted to the desired shape. For example, an inner form with the reduced diameter may be bonded to the inside of a standard shell by solvent bonding, ultrasonic welding, or other technique. This allows producers to have one or more basic insert shapes that may then be individualized using a series of forms, or third parts. In one embodiment, the inner diameter is reduced to zero, so that an attending physician or medical professional may entirely close the shunt, preventing blood flow altogether between the left and right atria.

Figure 46:
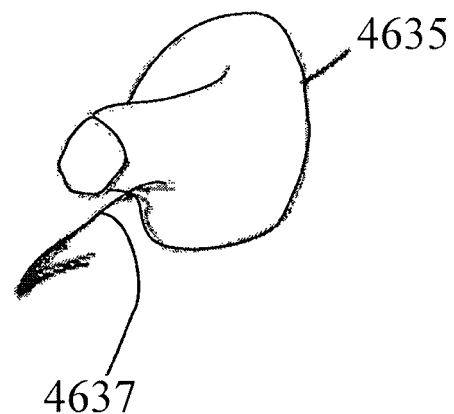
FIG. 46 is a perspective view of an insert portion of an embodiment of an implantable device.
Figure 47:
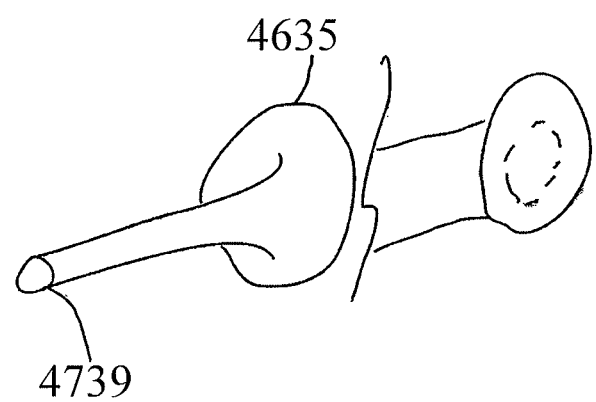
FIG. 47 is a perspective view of an insert portion of an embodiment of an implantable device.

It is desirable that the inserts and cages be retrievable, as noted above with respect to the retrieval loops shown in FIG. 43 for both the cage and the insert. A variety of other features besides loops may be used to retrieve the components of the adjustable intra-atrial shunt. Thus, insert 4635 is depicted with a snare leg 4637 in FIG. 46 and with a "wind sock" or lengthened end 4739 in FIG. 47. These features may also be added to the cage portions of the intra-atrial shunt for easy retrieval of the cage, and subsequent removal or re-positioning within the patient.

Figure 48:
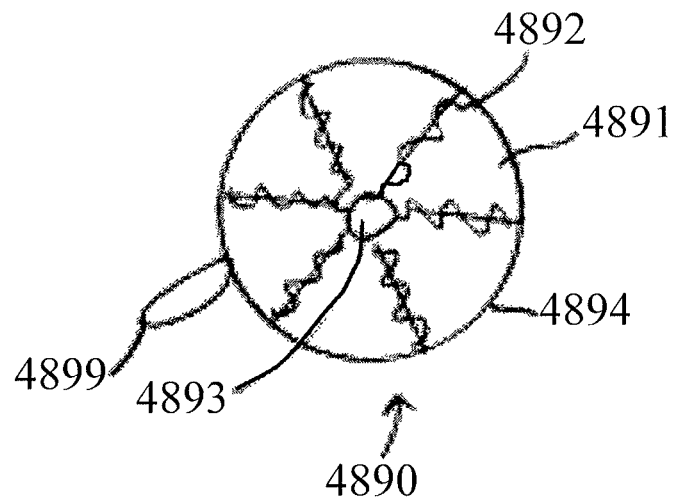
FIG. 48 is an end view of an insert portion of an embodiment of an implantable device.

The above embodiments are useful for adjusting the diameter of the shunt, but while useful, each adjustment is fixed. Other embodiments are constructed so that the openings or orifices gradually increase or decrease over time. In the embodiment of FIG. 48, flow control element or insert 4890 has an outward form of a thin cylinder. Insert 4890 includes a frame, which may include an outer circumference, and a plurality of flaps 4891. The flaps are made of a polymer such as PTFE, UHMWPE, HDPE, polypropylene, polysulfone, or other biocompatible plastic. Other embodiments may use extracellular materials or other suitable biologic materials. The flaps are sewn together with biosorbable sutures, such as polylactic acid, polyglycolic acid and polycaprolactone, other suitable biosorbable sutures, or combinations of these. There may also be an initial orifice 4893 in the center so that flow will occur upon placement of the insert 4890 into a cage. The sutures provide tension between the flaps and keep the flaps closed. As the sutures absorb, the tension is lost and the flaps open. Other embodiments may include no initial orifice.

When insert 4890 is first deployed, orifice 4893 allows limited flow. Over time, material from the sutures will be absorbed gradually into the bloodstream. The sutures will become thinner and weaker, and the joint between any two of the flaps will become looser, allowing more blood flow. Some of the suture joints may use more sutures and some may use less, so that the weakening of the sutures increases gradually over time, rather than all at once. Accordingly, insert 4890 will have an initially low flow of blood from an area of high pressure to low pressure, due to a small initial orifice. Later, as the sutures are biosorbed and the flap joints become looser, blood flow will increase. If more adjustment is needed, the insert 4890 may be removed via retrieval loop 4899 and replaced with another insert, such as one depicted in FIGS. 43-45 of the present application. Retrieval loop 4899 is desirably not biosorbable and may include a radiopaque member as discussed above.

Figures 49A, 49B:
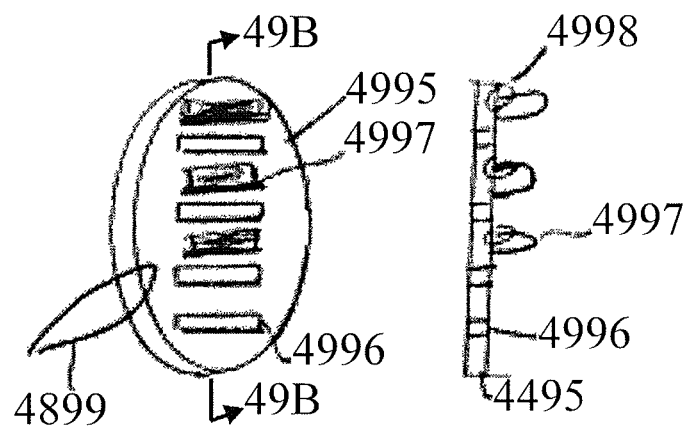
FIG. 49A is a perspective view of an insert portion of an embodiment of an implantable device.
FIG. 49B is a cross-sectional view taken along line 49B-49B of the insert portion of FIG. 49A.

The insert portion of another embodiment which utilizes an insert/cage combination is depicted in FIG. 49A. The insert portion of the inventive device of FIG. 49A is also shown in a cross-sectional view taken along line 49B-49B. In this embodiment, insert 4995 may be a plate may of biocompatible plastic, with a plurality of orifices 4996 and flaps 4997 above the orifices, the flaps sewn in place as shown with biosorbable sutures. One or more of the orifices may have no flap, the orifice intended to provide an initial opening that remains constantly open while the insert 4995 is deployed with a cage as shown above. When the insert is first deployed, the one or more orifices without flaps will provide flow. Over time, the sutures will be absorbed and will no longer be able to prevent the flaps 4997 from covering the orifices, thus decreasing the openings and the flow from the area of high pressure to the area of low pressure. In some cases, the sutures provide tension to retain the flaps in place, keeping the flaps in place and the flaps open; as the sutures absorb, the flaps deploy to close the orifices. Insert 4995 may be retrieved and removed via retrieval loop 4899.

Figure 50:
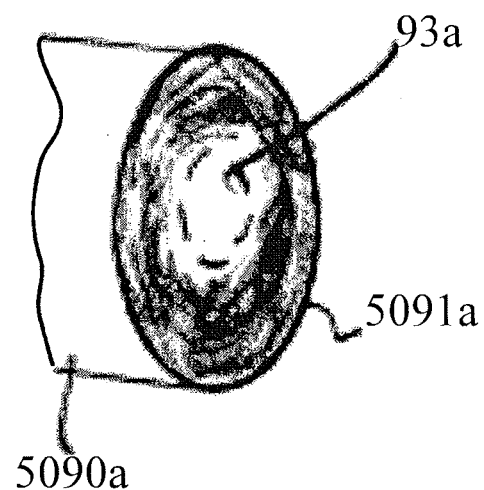
FIG. 50 is a partial perspective view of an end of an insert portion of an implantable device.
Figure 51:
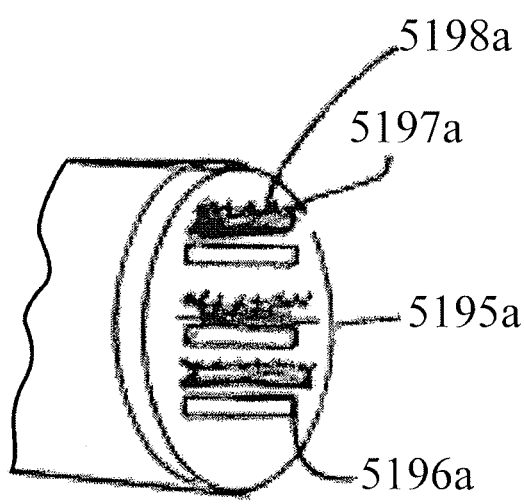
FIG. 51 is a partial perspective view of an end of an insert portion of an implantable device.

In some embodiments, the insert may be easier to fabricate if the flow control portions are placed near an end, i.e., an outside of the insert, as shown in FIGS. 50 and 51. For example, FIG. 50 depicts a tubular flow control element 5090*a*, in the form of a hollow tube intended for placement within one of the retainers discussed above. In this example, a flow control element 5091*a* is fabricated from a biosorbable polymer film, using biosorbable materials discussed above. The flow control element 5091*a* may be fabricated with an initial orifice 5093*a*, such as a central orifice, or it may be fabricated as a solid film, with no flow permitted through the device. Control of the absorption and loss of mass from the film may be easier to control with even a very small central orifice. After the flow control element in implanted into a patient, the film absorbs into the patient and becomes thinner and thinner, while the central orifice becomes larger and larger, allowing more blood flow as the orifice enlarges. In one embodiment, the thickness of the film may be graduated, with the thinnest portions at the center, with gradual thickening as the film approaches its circumference. The film may be bonded to the structure by ultrasonic bonding or other reliable method that prevents loosening or disassembly of the film from the structure during implantation. With this device, initial flow is low, but as the film absorbs into the patient, more and more flow is allowed as the orifice 5093*a* grows.

Although the descriptions given above for the embodiments having inserts that the inserts were described as being removable, it is to be understood that the present invention also includes embodiments wherein the inserts are not removable. In some such embodiments, the inserts are permanently attached to the cage, and in still other embodiments what are described above as inserts are not inserts at all but are integral portions of the cage. It is also to be understood that in some embodiments, the first anchor, the second anchor, and the shunt are integrally connected.

In another embodiment, depicted in FIG. 51, a hollow flow control cylinder 5195*a* includes one end with one or more orifices 5196*a*. In this embodiment, one or more orifices, such as each orifice, is open and is near a flap 5197*a* that is secured to the cylinder on one end. The other end of each flap is tethered to the cylinder with one or more biosorbable sutures 5198*a*. Upon implantation, all the orifices will be open and will allow flow of blood. As the suture or sutures biosorb, the top end of each flap, as shown in FIG. 51, will become loose and may drop down to block the orifice 5196*a* closest to that flap. Eventually, all the flaps will become loose and each flap will block the orifice closest to it, blocking flow of blood. However, the device of FIG. 51 may have one or more additional orifices without a flap, so that there is some blood flow even after all the sutures have absorbed. With this device, initial flow is relatively high, but as the sutures absorb into the patient, more and more of the orifices are blocked, cutting down flow, and if all orifices are blocked, flow is effectively stopped.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While embodiments have been disclosed and described in detail, it is understood that various modifications and improvements thereon will become readily apparent to those skilled in the art. Accordingly, the spirit and scope of the present invention is not limited by the foregoing examples, but is better understood by the claims below. All patents, published applications, and other documents identified herein are incorporated by reference herein in their entireties to the full extent permitted by law.

What is claimed is:

1. An expandable device adapted for percutaneous delivery into a membrane of a patient's heart, the device comprising:
   first and second anchors adapted to contact, respectively, first and second surfaces of the membrane; and
   a stent having a longitudinal axis and being connected to the first and second anchors, the stent comprising an outer cylindrical body comprising a superelastic material and a stent-like inner cylindrical body comprising a plastically deformable material and disposed within and connected to the outer cylindrical body, the stent being adapted to permit blood to flow across the membrane at a first rate;

wherein the stent-like inner cylindrical body comprises a first diameter and a second diameter which is expanded from the first diameter, wherein the stent-like inner cylindrical body will naturally remain in the expanded second diameter and permit blood to flow across the membrane at a second rate that is different from the first rate.

2. The device of claim 1, wherein the stent further comprises a cylindrical liner disposed within and attached to the inner cylindrical body.

3. The device of claim 1, wherein the outer cylindrical body has hooks and the hooks connect the outer cylindrical body to the inner cylindrical body.

4. The device of claim 1, wherein the plastically deformable material is stainless steel.

5. The device of claim 1, wherein the superelastic material is nitinol.

6. The device of claim 1 wherein each of the first and second anchors comprises a plurality of segments.

7. The device of claim 1 wherein the first anchor, the second anchor, and the stent are integrally connected.

* * * * *